US 12,208,135 B2

(12) United States Patent
Ryan et al.

(10) Patent No.: US 12,208,135 B2
(45) Date of Patent: *Jan. 28, 2025

(54) FORMULATIONS OF DENGUE VIRUS VACCINE COMPOSITIONS

(71) Applicant: Merck Sharp & Dohme LLC, Rahway, NJ (US)

(72) Inventors: Michael S. Ryan, Allentown, PA (US); Sherrie-Ann P. Martin, Paoli, PA (US); Morrisa Jones, Upper Darby, PA (US); Justin Stanbro, Sellersville, PA (US); Akhilesh Bhambhani, Doylestown, PA (US); Jeffrey Thomas Blue, Telford, PA (US); Heidi Joanne Pixley, Glenside, PA (US); Erin J. Green-Trexler, Green Lane, PA (US); Lynne Ann Isopi, Quakertown, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,421

(22) Filed: Dec. 6, 2023

(65) Prior Publication Data
US 2024/0131144 A1   Apr. 25, 2024

Related U.S. Application Data

(63) Continuation of application No. 17/815,037, filed on Jul. 26, 2022, now Pat. No. 11,883,480, which is a
(Continued)

(51) Int. Cl.
*A61K 39/12* (2006.01)
*A61K 9/19* (2006.01)
(Continued)

(52) U.S. Cl.
CPC ............... *A61K 39/12* (2013.01); *A61K 9/19* (2013.01); *A61K 39/39* (2013.01); *A61K 47/10* (2013.01);
(Continued)

(58) Field of Classification Search
None
See application file for complete search history.

(56) References Cited

U.S. PATENT DOCUMENTS 6,190,859 B1   2/2001   Putnak et al.
6,254,873 B1   7/2001   Putnak et al.
(Continued)

FOREIGN PATENT DOCUMENTS

CN     1119414 A       3/1996
CN     101115472 A     1/2008
(Continued)

OTHER PUBLICATIONS

Tlaxca, Jose L. et al., Live attenuated and inactivated viral vaccine formulation and nasal delivery: Potential and challenges, Advanced Drug Delivery Reviews, 93, 56-78, 2014.
(Continued)

*Primary Examiner* — Shanon A. Foley
(74) *Attorney, Agent, or Firm* — Jonathan B. Fitzgerald; Alysia A. Finnegan

(57) ABSTRACT

The present invention relates to formulations of dengue virus vaccine comprising at least one live, attenuated dengue virus or live, attenuated chimeric flavivirus, a buffer, a sugar, a cellulose derivative, a glycol or sugar alcohol, optionally an alkali or alkaline salt and an amino acid; and formulations of dengue virus vaccine comprising at least one live, attenuated dengue virus or live, attenuated chimeric flavivirus, a
(Continued)

buffer, a sugar of at least 150 mg/ml, a carrier, and optionally an alkali or alkaline salt and an amino acid.

5 Claims, 20 Drawing Sheets

Specification includes a Sequence Listing.

Related U.S. Application Data continuation of application No. 16/769,837, filed as application No. PCT/US2018/063541 on Dec. 3, 2018, now abandoned.

(60) Provisional application No. 62/595,842, filed on Dec. 7, 2017.

(51) Int. Cl.
  *A61K 39/39*    (2006.01)
  *A61K 47/10*    (2017.01)
  *A61K 47/26*    (2006.01)
  *A61K 47/32*    (2006.01)
  *A61K 47/36*    (2006.01)
  *A61K 47/42*    (2017.01)
  *A61K 39/00*    (2006.01)

(52) U.S. Cl.
  CPC ............ *A61K 47/26* (2013.01); *A61K 47/32* (2013.01); *A61K 47/36* (2013.01); *A61K 47/42* (2013.01); *A61K 2039/5254* (2013.01); *A61K 2039/55505* (2013.01); *A61K 2039/70* (2013.01)

(56) References Cited

U.S. PATENT DOCUMENTS

| | | | |
|---|---|---|---|
| 6,432,411 | B1 | 8/2002 | Ivy et al. |
| 11,883,480 | B2 * | 1/2024 | Ryan ................. A61K 9/19 |
| 2003/0180352 | A1 | 9/2003 | Patel |
| 2004/0022760 | A1 | 2/2004 | Mckenna et al. |
| 2012/0219588 | A1 | 8/2012 | Thompson et al. |
| 2015/0017191 | A1 * | 1/2015 | Fox ..................... A61K 9/113 |
| | | | 424/283.1 |
| 2015/0246114 | A1 | 9/2015 | Qiao et al. |
| 2016/0158248 | A1 | 6/2016 | Gizurarson |
| 2016/0199496 | A1 | 7/2016 | Jezek et al. |
| 2016/0296616 | A1 | 10/2016 | Croyle et al. |
| 2016/0310412 | A1 | 10/2016 | Tanoue et al. |
| 2016/0324783 | A1 | 11/2016 | Fox et al. |
| 2016/0354460 | A1 | 12/2016 | Poon et al. |
| 2023/0061673 | A1 | 3/2023 | Ryan et al. |

FOREIGN PATENT DOCUMENTS

| | | |
|---|---|---|
| CN | 101128216 A | 2/2008 |
| CN | 101296705 A | 10/2008 |
| CN | 101679954 A | 3/2010 |
| EP | 2143440 A1 | 1/2010 |
| EP | 2687229 A1 | 1/2014 |
| WO | 1993006214 A1 | 4/1993 |
| WO | 02/095075 | 11/2002 |
| WO | 03/092592 A2 | 11/2003 |
| WO | 2005016239 A2 | 2/2005 |
| WO | 2006074303 A2 | 7/2006 |
| WO | 2007002470 A2 | 1/2007 |
| WO | 2007038926 A1 | 4/2007 |
| WO | 2008/022196 | 2/2008 |
| WO | 2009014774 A1 | 1/2009 |
| WO | 2010037402 A1 | 4/2010 |
| WO | 2010105251 A2 | 9/2010 |
| WO | 2011098837 A1 | 8/2011 |
| WO | 2012154202 A1 | 11/2012 |
| WO | 2012160199 A1 | 11/2012 |
| WO | 2014204892 A1 | 12/2014 |
| WO | 2015057541 A1 | 4/2015 |
| WO | 2015059284 A1 | 4/2015 |
| WO | 2015093452 A1 | 6/2015 |
| WO | 2015130157 A1 | 9/2015 |
| WO | 2016106107 A2 | 6/2016 |
| WO | 2016203025 A1 | 12/2016 |
| WO | 2017041156 A2 | 3/2017 |
| WO | 2017056101 A1 | 4/2017 |
| WO | WO 2017056101 * | 4/2017 |
| WO | 2017109698 A1 | 6/2017 |
| WO | 2017165736 A1 | 9/2017 |
| WO | 2017179017 A1 | 10/2017 |
| WO | 2018027075 A1 | 2/2018 |
| WO | 2018053524 A1 | 3/2018 |
| WO | 2018183429 A1 | 10/2018 |
| WO | 2019077622 A1 | 4/2019 |
| WO | 2019112921 A1 | 6/2019 |

OTHER PUBLICATIONS

Duane J. Gubler, Dengue and Dengue Hemorrhagic Fever, Clinical Microbiology Reviews, 11-3, 480-496, Jul. 1998.

Erik A. Henchal, The Dengue Viruses, Clinical Microbiology Reviews, 3-4, 376-396, 1990.

Hansen, L.J.J. et al., Freeze-drying of live virus vaccines: A review, Vaccine, 33(42), 5507-5519, 2015.

Heinz, Franz et al., Flaviviruses and flavivirus vaccines, Vaccine;, 30, 4301-4306, 2012.

J. Robert Putnak et al., An evaluation of dengue type-2 inactivated, recombinant subunit, and live-attenuated vaccine candidates in the rhesus macaque model, Vaccine, 23, 4442-4452, 2005.

L.J. Braun et al., Characterization of a thermostable hepatitis B vaccine formulation, Vaccine, 27, 4609-4614, 2009.

Robert V. Gibbons, Dengue: an escalating problem, British Medical Journal, -, 1563-1566, 2002.

Tang, Roderick S. et al., Development of a PIV-vectored RSV vaccine: Preclinical evaluation of safety, toxicity, and enhanced disease and initial clinical testing in healthy adults, Vaccine, 26, 6373-6382, 2008.

Thomas J. Chambers, Flavivirus Genome Organization, Expression, and Replication Annu. Rev. Microbiol, Annu. Rev. Microbiol., 44, 649-88, 1990.

U.S. Appl. No. 17/815,037, filed Jul. 26, 2022.

* cited by examiner

Effect of CMC, PG, Amino Acids on DENV4 Stability

FIG. 2

Effect of Sugar Alcohol on DENV4 Lyophilization Yield

FIG.3

Effect of Sugar Alcohol on DENV4 Stability

FIG.4

Effect of pH on DENV4 Lyophilization Yield

FIG.5

Effect of NaCl Concentration on DENV4 Lyophilization Yield

FIG.9

Effect of propylene glycol and glycerol on Lyophilization Yields of Dengue Serotypes

FIG.11

Effect of propylene glycol and glycerol on Stability of Dengue Serotypes

FIG.12

FORMULATIONS OF DENGUE VIRUS VACCINE COMPOSITIONS

CROSS REFERENCE TO RELATED APPLICATIONS

The present application is a continuation application of U.S. patent application Ser. No. 17/815,037, filed Jul. 26, 2022, which is a continuation application of U.S. patent application Ser. No. 16/769,837, filed Jun. 4, 2020, which is a 371 national phase application of International Application No. PCT/US2018/063541, filed Dec. 3, 2018, which claims the benefit of U.S. Provisional Application No. 62/595,842, filed Dec. 7, 2017, hereby incorporated by reference in its entirety.

SEQUENCE LISTING

The instant application contains a Sequence Listing which has been submitted electronically in XML format and is hereby incorporated by reference in its entirety. Said XML copy, created on Sep. 26, 2022, is named 24547-US-CNT-_SL.xml and is 54,890 bytes in size.

FIELD OF THE INVENTION

The present invention relates to formulations of dengue virus vaccine comprising at least one live, attenuated dengue virus or live, attenuated chimeric flavivirus, a buffer, a sugar, a cellulose derivative and a sugar alcohol or glycol, and optionally an amino acid and an alkali or alkaline salt; and formulations of dengue virus vaccine comprising at least one live, attenuated dengue virus or live, attenuated chimeric flavivirus, a buffer, a sugar of at least 150 mg/ml, a carrier, and optionally an alkali or alkaline salt, or, alkali or alkaline salt and an amino acid.

BACKGROUND OF THE INVENTION

The family Flaviviridae includes the prototype yellow fever virus (YF), the four serotypes of dengue virus (DENV-1, DENV-2, DENV-3, and DENV-4), Japanese encephalitis virus (JE), tick-borne encephalitis virus (TBE), West Nile virus (WN), Saint Louis encephalitis virus (SLE), and about 70 other disease causing viruses. Flaviviruses are small, enveloped viruses containing a single, positive-strand RNA genome. Ten gene products are encoded by a single open reading frame and are translated as a polyprotein organized in the order: capsid (C), "preMembrane" (prM, which is processed to "Membrane" (M) just prior to virion release from the cell), "envelope" (E), followed by non-structural (NS) proteins NS1, NS2a, NS2b, NS3, NS4a, NS4b and NS5 (reviewed in Chambers, T. J. et al., *Annual Rev Microbiol* (1990) 44:649-688; Henchal, E. A. and Putnak, J. R., *Clin Microbiol Rev.* (1990) 3:376-396). Individual flaviviral proteins are then produced through precise processing events mediated by the host as well as virally encoded proteases.

The envelope of flaviviruses is derived from the host cell membrane and contains the virally-encoded membrane anchored membrane (M) and envelope (E) glycoproteins. The E glycoprotein is the largest viral structural protein and contains functional domains responsible for cell surface attachment and intra-endosomal fusion activities. It is also a major target of the host immune system, inducing the production of virus neutralizing antibodies, which are associated with protective immunity.

Dengue viruses are transmitted to man by mosquitoes of the genus *Aedes*, primarily *A. aegypti* and *A. albopictus*. Infection by dengue viruses leads to a diverse clinical picture ranging from an inapparent or mild febrile illness, through classical dengue fever (DF), to dengue hemorrhagic fever/dengue shock syndrome (DHF/DSS). Dengue fever is characterized by high fever, headache, joint and muscle pain, rash, lymphadenopathy and leucopenia (Gibbons, R. V. and D. W. Vaughn, *British Medical Journal* (2002) 324: 1563-1566). DHF/DSS is a more severe form of infection more common in children, marked by vascular permeability and/or severe hemorrhagic manifestations ranging from the presence of petechiae and ecchymosis to spontaneous severe hemorrhage and profound shock. Without diagnosis and prompt medical intervention, the sudden onset and rapid progression of DHF/DSS can be fatal if untreated.

Dengue viruses are the most significant group of arthropod-transmitted viruses in terms of global morbidity and mortality with an estimated one hundred million dengue infections occurring annually including at least 36 million cases of dengue fever and 250,000 to 500,000 cases of DHF/DSS (Gubler, D. J., *Clin. Microbiol. Rev.* (1998) 11:480-496; Gibbons, supra). With the global increase in population, urbanization of the population especially throughout the tropics, and the lack of sustained mosquito control measures, the mosquito vectors of dengue have expanded their distribution throughout the tropics, subtropics, and some temperate areas, bringing the risk of dengue infection to over half the world's population. Modern jet travel and human emigration have facilitated global distribution of dengue serotypes, such that multiple serotypes of dengue are now endemic in many regions. There has been an increase in the frequency of dengue epidemics and the incidence of DHF/DSS in the last 20 or more years. For example, in Southeast Asia, DHF/DSS is a leading cause of hospitalization and death among children (Gubler, supra; Gibbons and Vaughn, supra).

To date, the development of flavivirus vaccines has been met with mixed success. There are four basic approaches that have been implemented in an effort to produce vaccine candidates to protect against disease caused by flaviviruses: live-attenuated, inactivated whole virus, recombinant sub-unit protein, and DNA-based vaccines. A live-attenuated vaccine for yellow fever virus has been available for decades and more recently a live attenuated vaccine for Japanese encephalitis has been registered in various countries around the world. The use of inactivated whole virus vaccines has been demonstrated for TBE and JE viruses with several registered products available. Heinz et al. Flavivirus and flavivirus vaccines. *Vaccine* 30: 4301-06 (2012).

Despite the successes of the YF, JE, and TBE vaccines highlighted above, the use of live-attenuated virus and inactivated virus methods to develop vaccines for dengue virus has been met with significant challenges. There are four serotypes of dengue virus (DENV1, DENV2, DENV3, and DENV4) and strains of each serotype are found circulating throughout the dengue endemic regions of the world. Natural infection confers long lasting immunity to the infecting serotype but not to other dengue serotypes. The more severe forms of the disease (DHF/DSS) occur most often after secondary dengue infection, when infection with one serotype of dengue virus is followed by a second infection with another serotype. The more frequent association of DHF and DSS with secondary dengue infection has been hypothesized to be due to non-neutralizing antibodies induced by infection with one virus type enhancing infectivity of a second dengue virus type (antibody-dependent enhancement—ADE).

To date, the majority of the vaccines tested clinically are live, attenuated vaccines. The use of non-replicating vaccine candidates is also being explored. For example, Ivy et al. (U.S. Pat. No. 6,432,411) disclose a tetravalent subunit vaccine comprising DEN1-4 80% E (the peptide region of DEN1-4 corresponding to amino acids 1-395 of the DENV-2 envelope polypeptide) proteins. Ivy et al, supra, also report compositions comprising DENV 1-4 80% E and ISCOMATRIX® adjuvant. Coller et al. (WO 2012/154202) disclose tetravalent formulations comprising DEN1-4 80% E of DEN 1-4. Inactivated viruses may also be used as potential vaccine candidates or as components of an effective vaccine (Putnak et al. *Vaccine* 23: 4442-4452 (2005), U.S. Pat. Nos. 6,190,859, 6,254,873 and Sterner et al. WO 2007/002470). Compositions comprising a live attenuated dengue virus vaccine and a non-replicating dengue vaccine are disclosed in International Patent Application No. PCT/US14/042625 (WO2014/204892).

Whole viruses are one of the commonly used antigens in several vaccine products due to their ability to generate humoral and cellular immune responses. Vaccine products containing whole viruses are challenging to stabilize as these are sensitive to heat, freeze/thaw and other processing stresses leading to significant potency losses. These products are typically stored frozen (below −20° C.) or as dried powder. Frozen products are not easy to store and distribute as they need a stringent cold-chain requirement to prevent potency loss. Drying of whole viruses, especially enveloped viruses, often leads to significant loss of potency due to the freezing and drying stresses encountered during the drying process. Therefore, there is a need in the art to generate stable formulations of Dengue virus.

SUMMARY OF THE INVENTION

The current invention provides stable formulations of live attenuated dengue vaccine. The addition of a cellulose derivative and a sugar alcohol or glycol improved stability and/or yield after drying. Alternatively, the addition of sugar of at least 150 mg/ml improved stability and/or yield after microwave drying.

In one aspect, the invention provides a formulation comprising a live attenuated dengue vaccine comprising at least one live attenuated dengue virus (LAV) or at least one live attenuated chimeric flavivirus (LACY), a buffer at pH about 6.5 to 8.5, a sugar, a glycol or sugar alcohol, and a cellulose derivative selected from the group consisting of carboxymethyl cellulose, hydroxypropyl cellulose (HPC), hydroxypropyl methylcellulose (HPMC), 2-hydroxyethyl cellulose (2-HEC), crosscarmellose, and methyl cellulose, or a pharmaceutically acceptable salt thereof; optionally an alkali or alkaline salt, and optionally an amino acid selected from the group consisting of Ala, Asp, His, Leu, Lys, Gln, Pro or Glu, or a combination thereof.

In one embodiment, the buffer is selected from the group consisting of succinate, histidine, phosphate, TRIS, Bis-Tris, MES, MOPS, HEPES, acetate and citrate, or a combination thereof. In another embodiment, the alkali or alkaline salt is magnesium chloride, calcium chloride, potassium chloride, sodium chloride or a combination thereof. In a further embodiment, the sugar is trehalose or sucrose. In one embodiment, the cellulose derivative is a pharmaceutically acceptable salt of carboxymethyl cellulose. In another embodiment, the glycol is selected from the group consisting of propylene glycol, polypropylene glycol, ethylene glycol, polyethylene glycol, and polyethylene glycol monomethyl ethers. In a further embodiment, the sugar alcohol is glycerol.

In another aspect, the formulation comprises a live attenuated dengue vaccine comprising at least one live attenuated dengue virus (LAV) or at least one live attenuated chimeric flavivirus at about 100-10,000,000 pfu/ml, a buffer at pH about 6.5 to 8.5, about 50-300 mg/ml sugar, about 2.5-10.0 mg/ml propylene glycol (PG) or glycerol, and about 0.3-10 mg/ml sodium carboxymethylcellulose (sodium CMC), optionally about 10-150 mM NaCl, and optionally about 10-100 mM amino acid selected from the group consisting of Ala, Asp, His, Leu, Lys, Gln, Pro or Glu, or a combination thereof; a live attenuated dengue vaccine at about 100-100,000 pfu/ml, about 5-300 mM histidine, TRIS, Bis-Tris or phosphate buffer, or a combination thereof at pH about 7.0 to 8.0, about 50-300 mg/ml sugar, about 3-10 mg/ml propylene glycol or glycerol, and about 3-10 mg/ml sodium carboxymethylcellulose, optionally about 15-75 mM NaCl, and optionally about 10-75 mM amino acid selected from the group consisting of Ala, Asp, His, Leu, Lys, Gln, Pro or Glu, or a combination thereof; a live attenuated dengue vaccine at about 600-20,000 pfu/ml, about 5-300 mM potassium phosphate buffer at pH about 7.0-8.0, about 60-120 mg/ml sucrose or trehalose or a combination thereof, about 3-7 mg/ml propylene glycol or glycerol, and about 3-7 mg/ml sodium carboxymethylcellulose with average molecular weight of about 90,000, and about 30-90 mM NaCl, and optionally about 10-75 mM amino acid Leu, Lys or Glu, or a combination thereof; a live attenuated dengue vaccine at about 600-20,000 pfu/ml, about 11 mM potassium phosphate buffer at pH about 7.0-8.0, about 90 mg/ml sucrose, about 5 mg/ml propylene glycol or glycerol, about 5 mg/ml sodium carboxymethylcellulose with average molecular weight of about 90,000, and about 75 mM NaCl; a live attenuated dengue vaccine at about 600-20,000 pfu/ml, about 11 mM potassium phosphate buffer at pH about 7.0-8.0, about 90 mg/ml sucrose, about 5 mg/ml propylene glycol, about 5 mg/ml sodium carboxymethylcellulose with average molecular weight of about 90,000, about 50 mM NaCl, and about 25 mM Leu; a live attenuated dengue vaccine at about 600-20,000 pfu/ml, about 11 mM potassium phosphate buffer at pH about 7.5, about 90 mg/ml sucrose, about 5 mg/ml propylene glycol, about 5 mg/ml sodium carboxymethylcellulose with average molecular weight of about 90,000, and about 30 mM NaCl. In one aspect of the foregoing embodiments, the formulation further comprises about 90-200 mg/ml trehalose.

In a preferred embodiment of the invention, the formulation comprises a live attenuated dengue vaccine comprising at least one live attenuated dengue virus (LAV) or at least one live attenuated chimeric flavivirus at about 600-20,000 pfu/ml, about 11 mM potassium phosphate buffer at pH about 7.5-8, about 90 mg/ml sucrose, about 110 mg/ml trehalose, about 5 mg/ml propylene glycol, about 5 mg/ml sodium carboxymethylcellulose with average molecular weight of about 90,000, about 50 mM NaCl, and about 25 mM Leu. In one aspect of the foregoing embodiments, the formulation further comprises a surfactant selected from poloxamer 188 and poloxamer 407 at about 0.0001 to 5% w/v.

The invention also provides a formulation that comprises a live attenuated dengue vaccine comprising at least one live attenuated dengue virus (LAV) or at least one live attenuated chimeric flavivirus at about 100-10,000,000 pfu/ml, a buffer at pH about 6.5 to 8.5, a sugar at about 150-300 mg/ml, a carrier selected from the group consisting of polyvinylpyrrolidone (PVP), carboxymethyl cellulose, hydroxypropyl cellulose (HPC), hydroxypropyl methylcellulose (HPMC), 2-hydroxyethyl cellulose (2-HEC), crosscarmellose, methyl cellulose or a pharmaceutically acceptable salt thereof, Human Serum Albumin (HSA) and gelatin; optionally an alkali salt or alkaline salt at about 5-100 mM; optionally an amino acid Gln, Pro or Glu, or a combination thereof.

In one embodiment, the buffer is selected from the group consisting of succinate, histidine, phosphate, TRIS, Bis-Tris, MES, MOPS, HEPES, acetate and citrate, or a combination thereof. In another embodiment, the alkali or alkaline salt is magnesium chloride, calcium chloride, potassium chloride, sodium chloride or a combination thereof. In a further embodiment, the sugar is trehalose or sucrose, or a combination thereof. In one embodiment, the sucrose to trehalose ratio is between 1:1 to 1:4. In another embodiment, the carrier is a sodium carboxymethyl cellulose, HPMC, HSA or gelatin.

In a further aspect, the invention provides formulations of a live attenuated dengue vaccine comprising at least one live attenuated dengue virus (LAV) or at least one live attenuated chimeric flavivirus at about 200-100,000 pfu/ml, a buffer at pH about 6.5-8.0, about 150-300 mg/ml sugar as a combination of sucrose and trehalose, about 0.3 to 40 mg/ml sodium CMC, HSA, HPMC or gelatin, optionally about 10-100 mM alkali or alkaline salt, and optionally about 5-25 mM glutamic acid; a live attenuated dengue vaccine at about 600-20,000 pfu/ml, about 5-300 mM histidine, TRIS or phosphate buffer, or a combination thereof at pH about 7.0 to 8.0, about 50-100 mg/ml sucrose, about 90-200 mg/ml trehalose, about 0.3-10 mg/ml sodium CMC or about 10-40 mg/ml gelatin, and about 30-90 mM alkali or alkaline salt; a live attenuated dengue vaccine at about 600-20,000 pfu/ml, about 5-20 mM potassium phosphate at pH about 7-8, about 75 mg/ml sucrose, about 175 mg/ml trehalose, about 5 mg/ml sodium CMC with average molecular weight of about 90,000, and about 30 mM NaCl; a live attenuated dengue vaccine at about 600-20,000 pfu/ml, about 5-20 mM potassium phosphate at pH about 7.0-8.0, about 75 mg/ml sucrose, about 175 mg/ml trehalose, about 25 mg/ml gelatin, and about 30 mM NaCl; a live attenuated dengue vaccine at about 600-20,000 pfu/ml, about 5-20 mM potassium phosphate at pH about 7.0-8.0, about 250 mg/ml sucrose, and about 50 mg/ml PVP K12. In one aspect of the foregoing embodiments, the formulation further comprises a surfactant selected from poloxamer 188 and poloxamer 407 at about 0.0001 to 5% w/v.

In certain aspects of the foregoing embodiments, the formulation further comprises an aluminum adjuvant. The above formulations can be frozen or lyophilized, or reconstituted in solution. In one embodiment, the reconstitution is performed with about 0.5-1.0 ml saline solution, water or Bacteriostatic Water for Injection (BWFI) and optionally a diluent comprising an aluminum adjuvant. In another embodiment, the formulation is the aqueous solution prior to lyophilization or microwave vacuum drying.

In one embodiment, the live attenuated dengue vaccine comprises tetravalent live attenuated dengue virus or live attenuated chimeric flavivirus. In another embodiment, the LAV or the LACV comprise a viral genome that contains a deletion of about 30 nucleotides corresponding to the TL-2 stem-loop structure of the 3' untranslated (UTR) region; which reduces the replicative capacity of the virus. In a further embodiment, the live attenuated dengue virus is an LAV that comprise a viral genome that contains a deletion of about 30 nucleotides corresponding to the TL-2 stem-loop structure of the 3' untranslated (UTR) region, and is immunogenic against dengue serotype 3, wherein the viral genome of the LAV further contains a deletion of nucleotides upstream from the Δ30 deletion corresponding to the TL-3 structure of the 3'UTR.

In preferred embodiments of the invention, the live attenuated dengue vaccine is a live attenuated tetravalent vaccine comprising a DEN1Δ30 virus, a DEN2/4Δ30 virus (a DEN2 Δ30LACV on a DEN4 backbone), a DEN3Δ30 virus and a DEN4Δ30 virus. In another preferred embodiment, the live attenuated dengue virus is an LAV comprising rDEN1Δ30-1545, rDEN2/4Δ30 (ME)-1495,7163, rDEN3Δ30/31-7164, and rDEN4Δ30-7132,7163,8308.

BRIEF DESCRIPTION OF THE DRAWINGS

Figure 2:
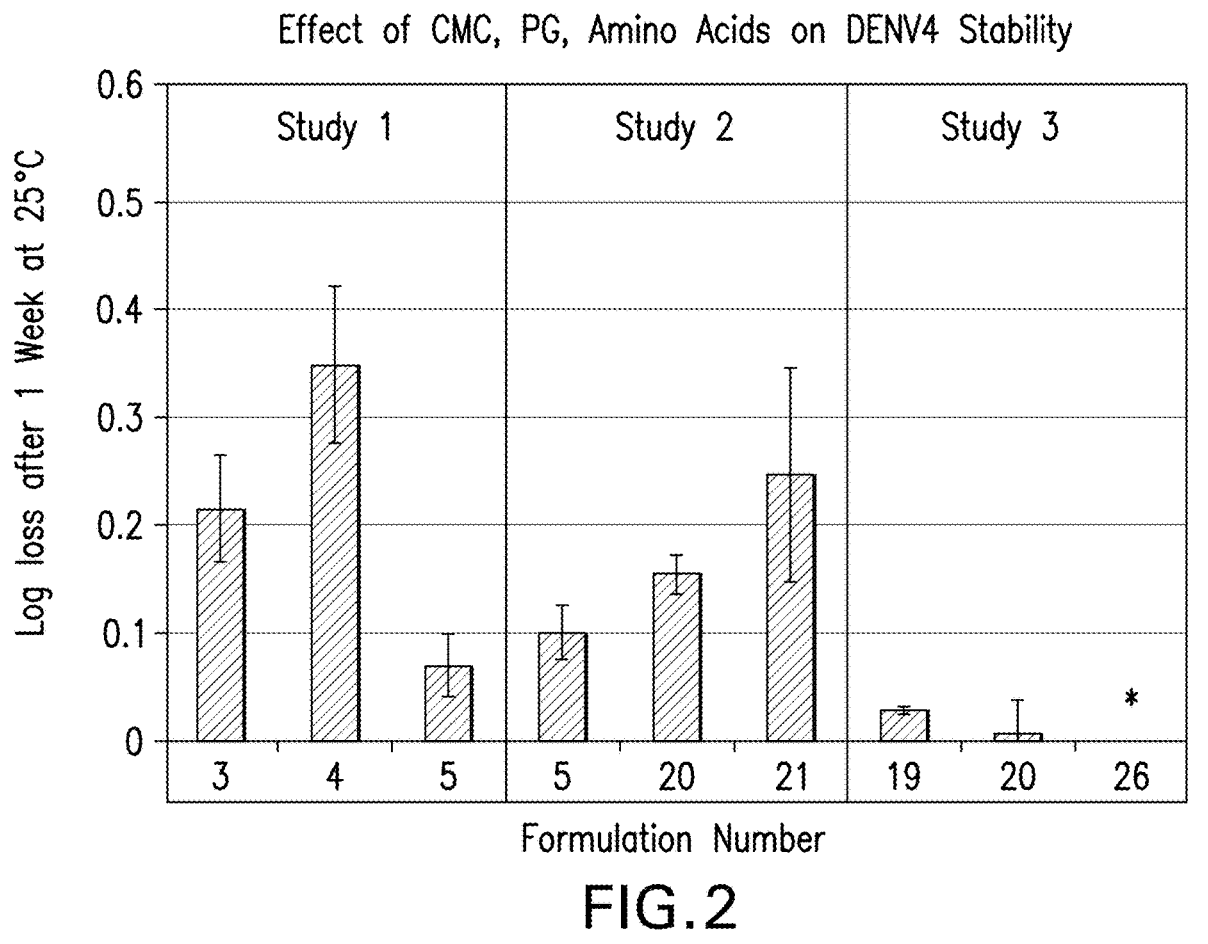

FIG. 2: Effect of Sodium CMC, PG, amino acids on DENV4 stability for DEN4 formulations. Formulation 26 (*) was not tested due to cake collapse after storage at 25° C.

FIG. 3: Effect of sugar alcohol on DENV4 lyophilization yield for DEN4 formulations.

Figure 4:
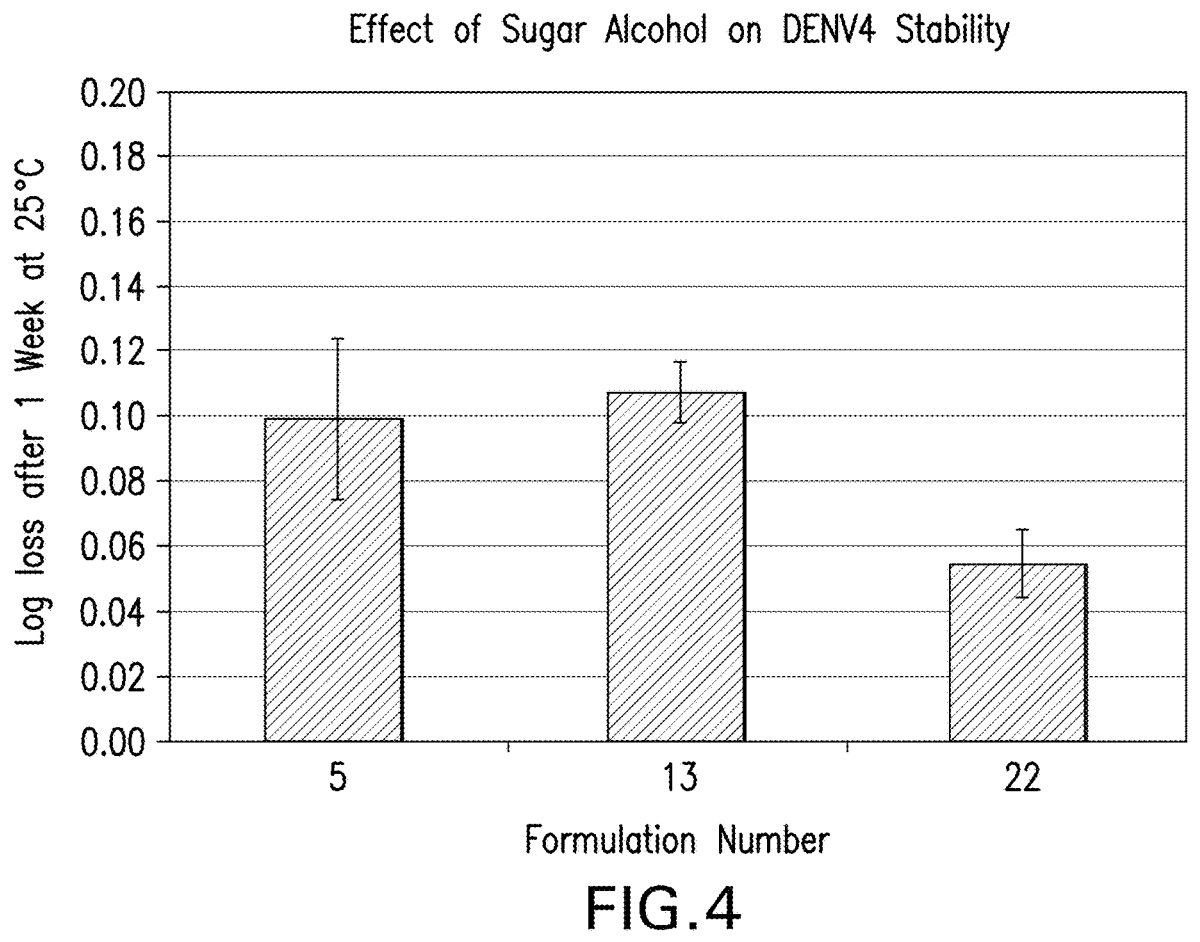

FIG. 4: Effect of sugar alcohol on DENV4 stability for DEN4 formulations.

Figure 5:
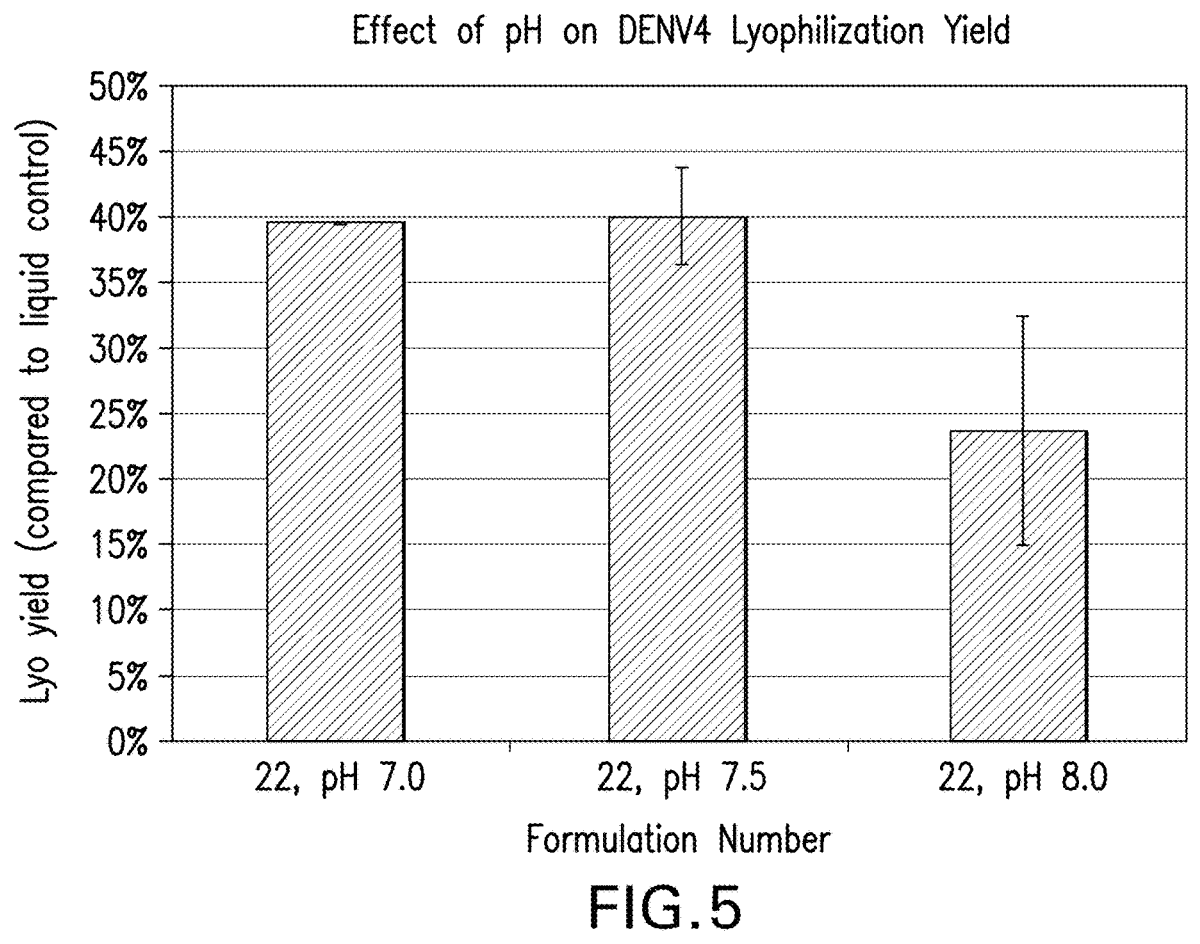

FIG. 5: Effect of pH on DENV4 lyophilization yield for DEN4 formulations.

FIG. 9: Effect of NaCl concentration on DENV4 lyophilization yield. for DEN4 formulations.

FIG. 11: Effect of propylene glycol and glyercol on lyophilization yields of Dengue serotypes.

FIG. 12: Effect of propylene glycol and glycerol on stability of Dengue serotypes.

DETAILED DESCRIPTION OF THE INVENTION

Figure 1:
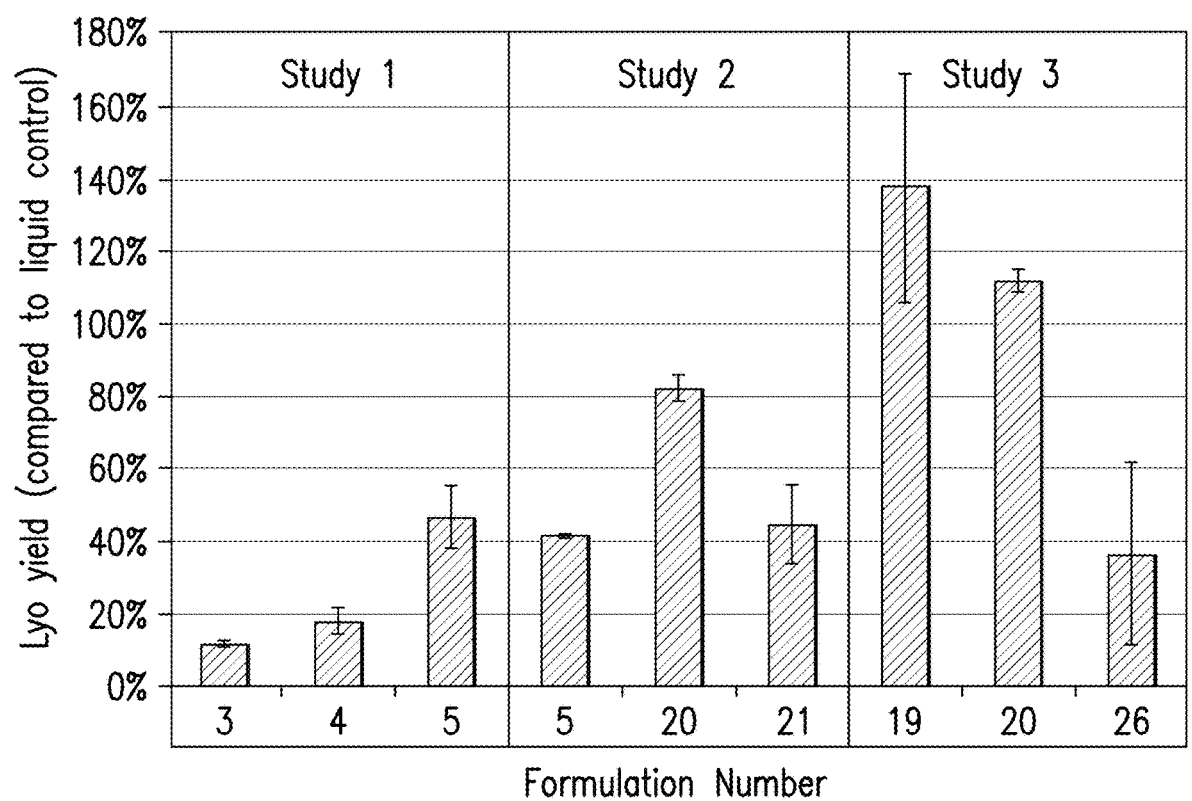
FIG. 1: Effect of Sodium CMC, PG, amino acids on DENV4 lyophilization yield for DEN4 formulations.
Figure 6:
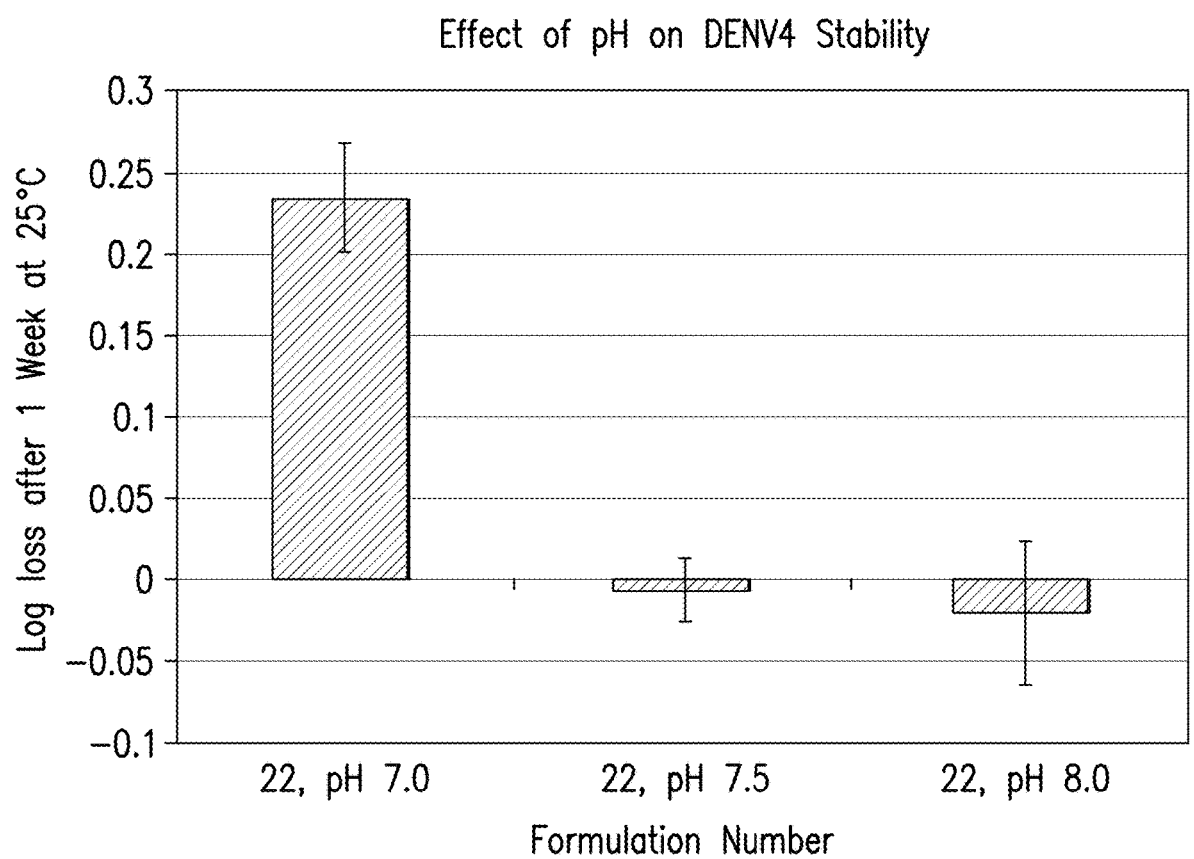
FIG. 6: Effect of pH on DENV4 stability for DEN4 formulations.
Figure 7:
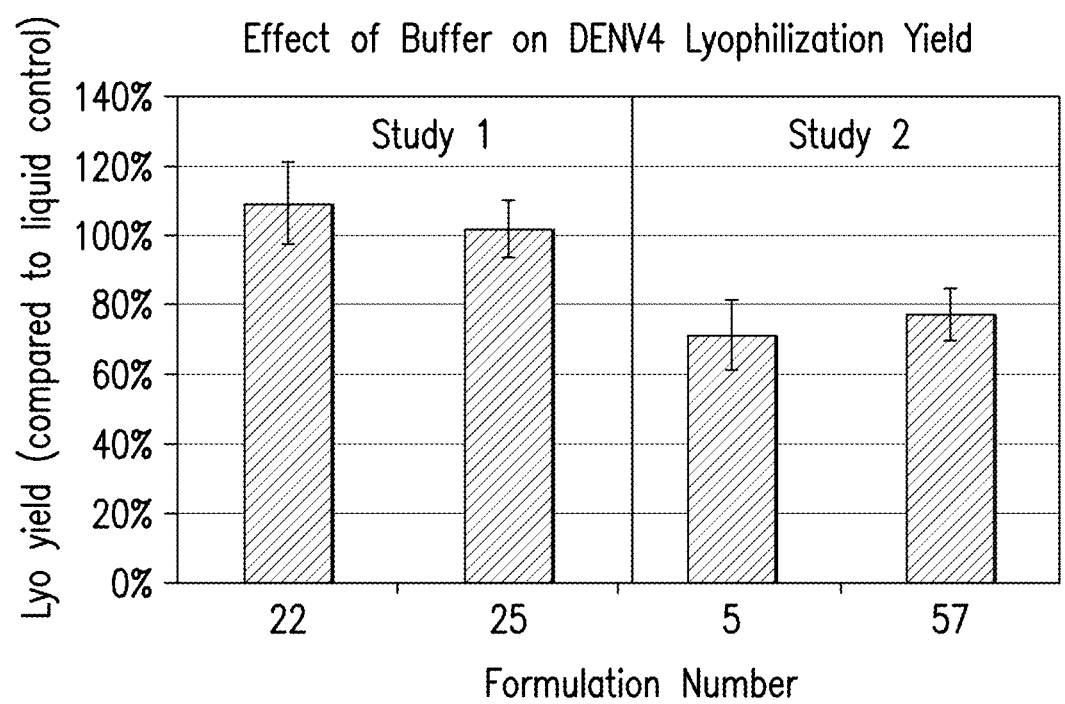
FIG. 7: Effect of buffer on DENV4 lyophilization yield for DEN4 formulations.
Figure 8:
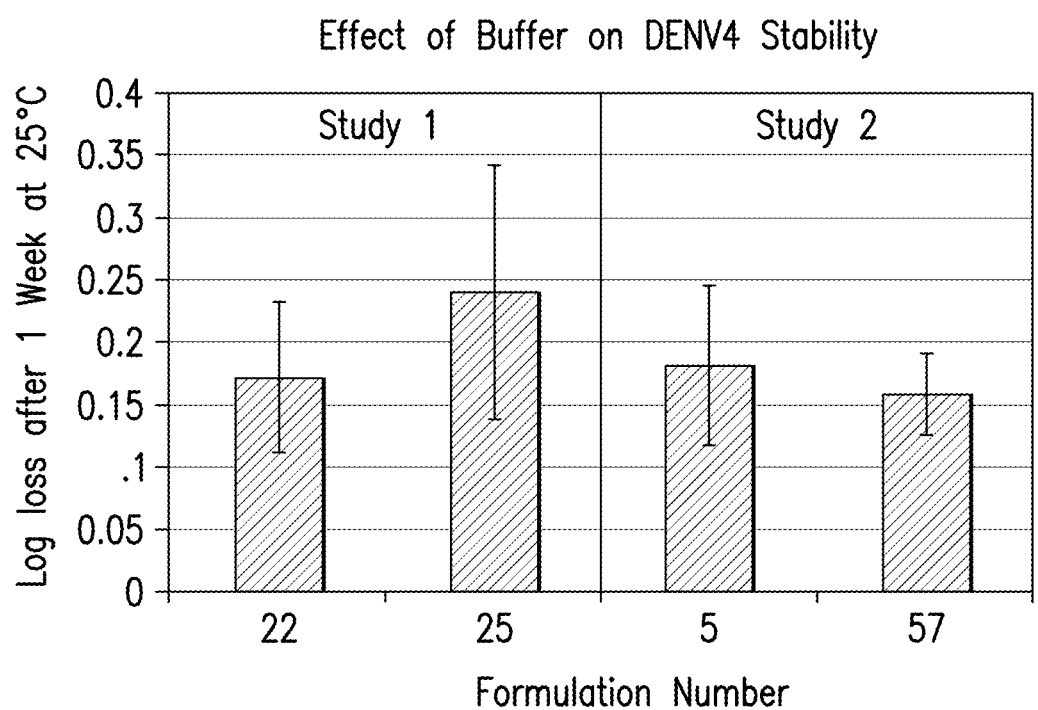
FIG. 8: Effect of buffer on DENV4 stability for DEN4 formulations.
Figure 10:
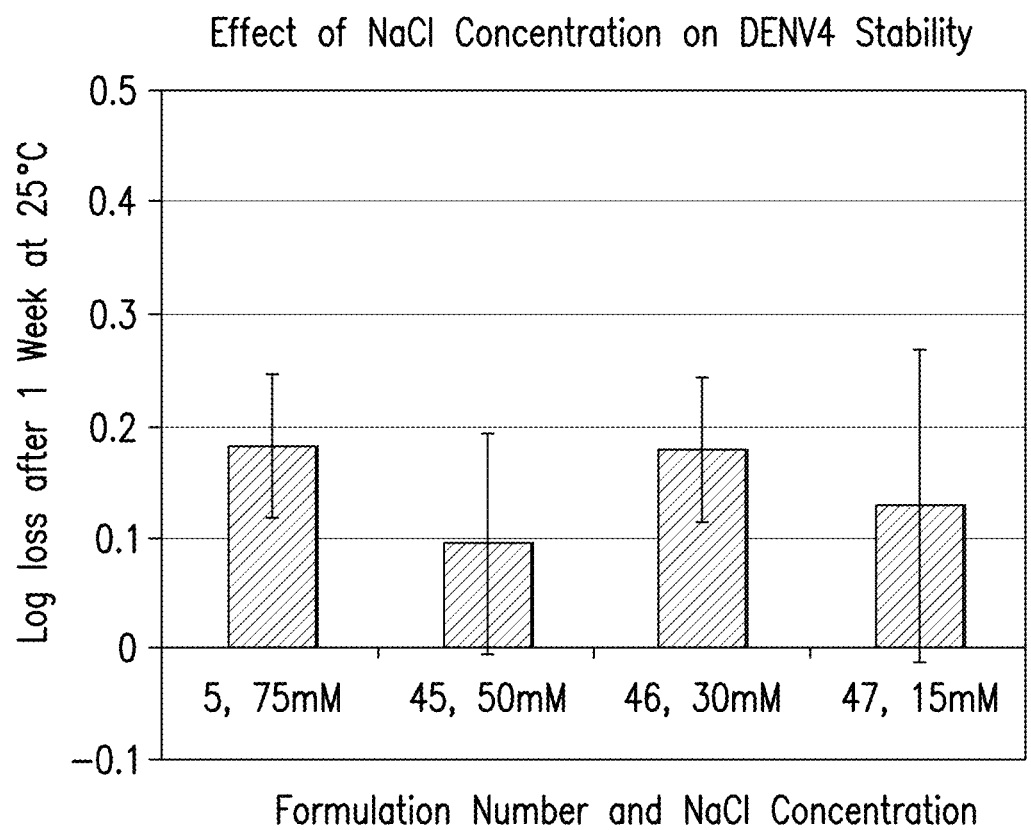
FIG. 10: Effect of NaCl concentration on DENV4 stability for DEN4 formulations.
Figure 13:
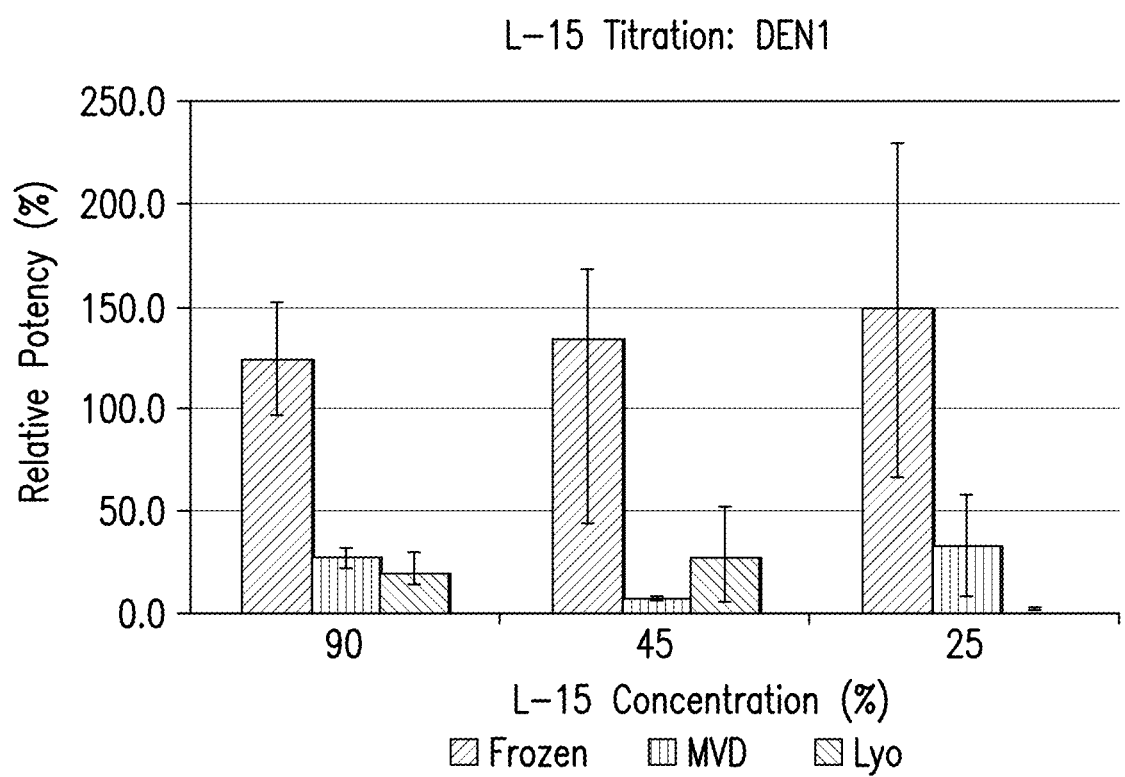
FIG. 13: Effect of L-15 concentration on relative potency for frozen, microwave dried (MVD) and lyophilized (lyo) DEN1 formulations.
Figure 14:
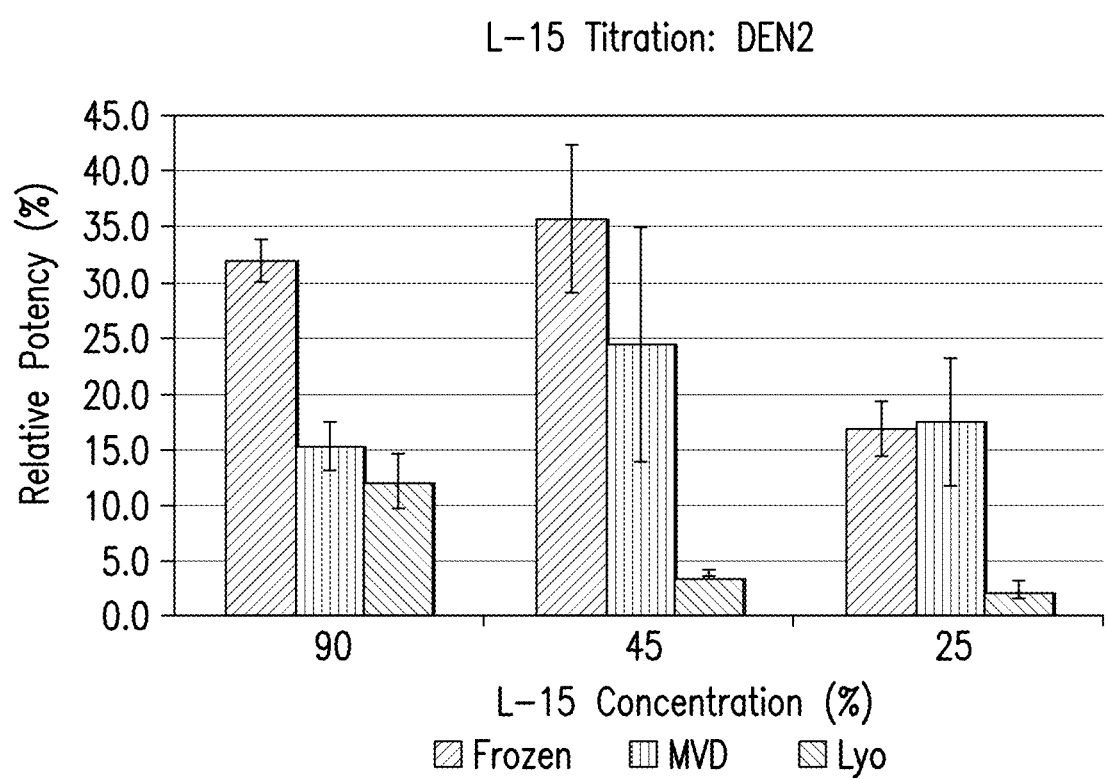
FIG. 14: Effect of L-15 concentration on relative potency for frozen, microwave dried (MVD) and lyophilized (lyo) DEN2 formulations.
Figure 15:
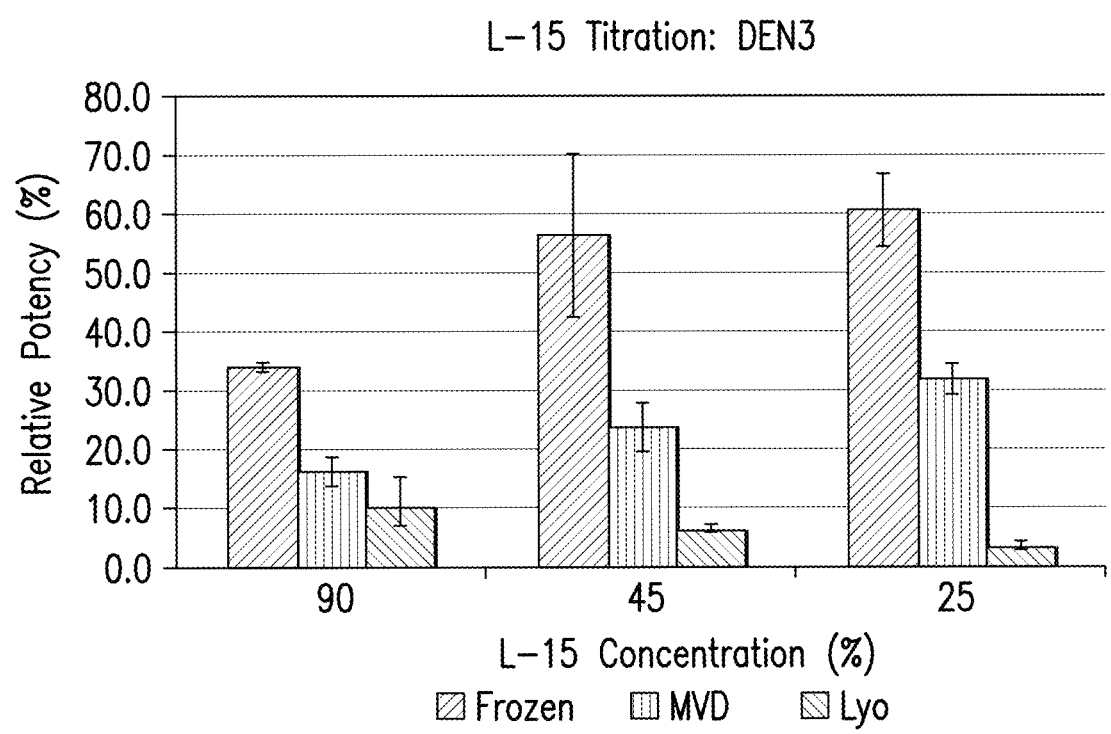
FIG. 15: Effect of L-15 concentration on relative potency for frozen, microwave dried (MVD) and lyophilized (lyo) DEN3 formulations.
Figure 16:
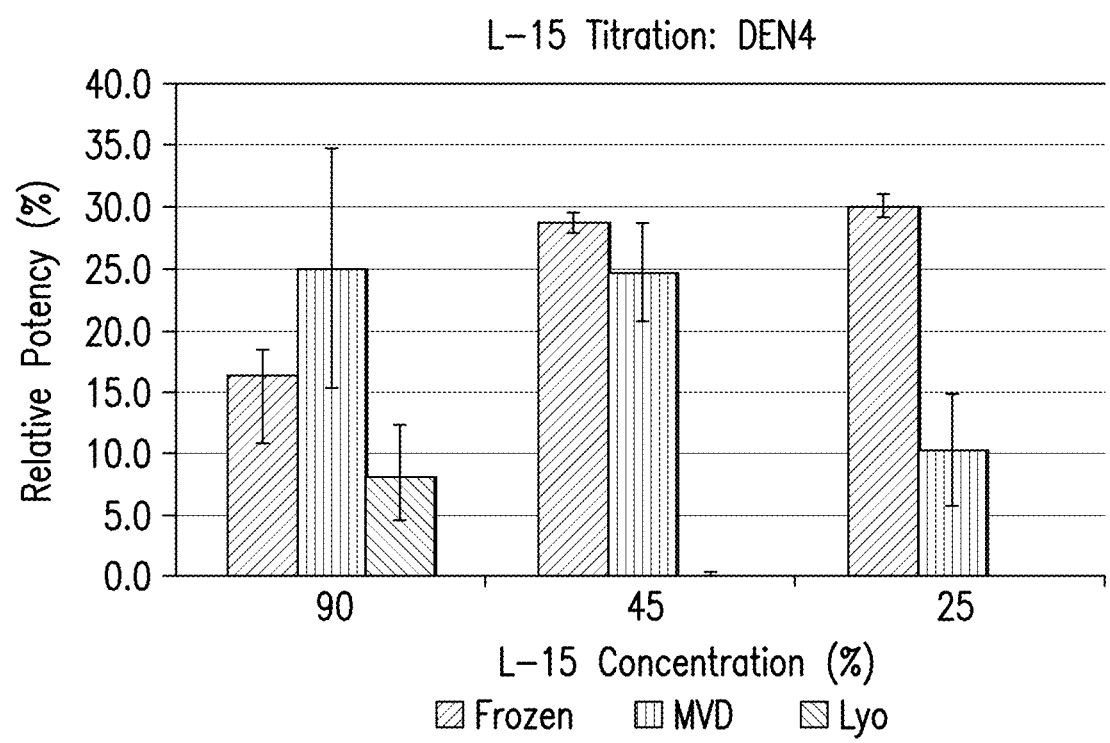
FIG. 16: Effect of L-15 concentration on relative potency for frozen, microwave dried (MVD) and lyophilized (lyo) DEN4 formulations.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

The term "about", when modifying the quantity (e.g., mM, or M) of a substance or composition, the percentage (v/v or w/v) of a formulation component, the pH of a solution/formulation, or the value of a parameter characterizing a step in a method, or the like refers to variation in the numerical quantity that can occur, for example, through typical measuring, handling and sampling procedures involved in the preparation, characterization and/or use of the substance or composition; through instrumental error in these procedures; through differences in the manufacture, source, or purity of the ingredients employed to make or use the compositions or carry out the procedures; and the like. In certain embodiments, "about" can mean a variation of ±0.1%, 0.5%, 1%, 2%, 3%, 4%, 5%, or 10%.

The term "bulking agents" comprise agents that provide the structure of the freeze-dried product. Common examples used for bulking agents include mannitol, glycine, and lactose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers.

The "Dengue Virus reference sample" has the same dengue virus formulation components and ratios as the dengue virus formulation test sample, and refers to the solid composition immediately after drying the dengue virus formulation under the same conditions as the dengue virus formulation test sample (i.e. lyophilization, microwave dried, lyosphere dried), or the foregoing dried solid composition stored at conditions where there is no or minimal infectivity loss of the dengue virus (i.e. stored at or below −70° C.); or the frozen solid dengue virus formulation at −70° C.

"Glycol" refers to a chemical compound with two hydroxyl groups.

"Infectivity loss" refers to comparing the loss of viral replication of a dengue virus test sample to a dengue virus reference sample using methods known in the art. In one embodiment, the infectivity loss is measured using a dengue relative infectivity assay. In another embodiment, the infectivity loss is measured using a plaque assay.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

"Lyosphere," as used herein, refers to dried frozen unitary bodies comprising a therapeutically active agent which are substantially spherical or ovoid-shape. In some embodiments, the lyosphere diameter is from about 2 to about 12 mm, preferably from 2 to 8 mm, such as from 2.5 to 6 mm or 2.5 to 5 mm. In some embodiments, the volume of the lyosphere is from about 20 to 550 µL, preferably from 20 to 100 µL, such as from 20 to 50 µL. In embodiments wherein the lyosphere is not substantially spherical, the size of the lyosphere can be described with respect to its aspect ratio, which is the ratio of the longer dimension to the shorter dimension. The aspect ratio of the lyospheres can be from 0.5 to 2.5, preferably from 0.75 to 2, such as from 1 to 1.5.

"Microwave Vacuum Drying" as used herein, refers to a drying method that utilizes microwave radiation (also known as radiant energy or non-ionizing radiation) for the formation of dried vaccine products (preferably, <6% moisture) of a vaccine formulation through sublimation. In certain embodiments, the microwave drying is performed as described in US2016/0228532. In one embodiment, the microwave radiation is in traveling wave format.

A "reconstituted solution" is one that has been prepared by dissolving dried virus in solid form (such as a lyophilized cake) in a diluent such that the virus is dispersed in the reconstituted solution. The reconstituted solution is suitable for administration, (e.g. intramuscular administration), and may optionally be suitable for subcutaneous administration.

"salt(s)", as employed herein, denotes acidic salts formed with inorganic and/or organic acids, as well as basic salts formed with inorganic and/or organic bases. Pharmaceutically acceptable (i.e., non-toxic, physiologically acceptable) salts are preferred, although other salts are also useful. Exemplary basic salts include ammonium salts, alkali metal salts such as sodium, lithium, and potassium salts, alkaline earth metal salts such as calcium and magnesium salts, zinc salts, salts with organic bases (for example, organic amines) such as N-Me-D-glucamine, Choline, tromethamine, dicyclohexylamines, t-butyl amines, and salts with amino acids such as arginine, lysine and the like.

"sugar alcohol" refers to polyols derived from a sugar and have the general formula $HOCH_2(CHOH)_nCH_2OH$, n=1, 2, 3, 4, 5, 6, 7, 8, 9 or 10. Examples include but are not limited to mannitol, sorbitol, erythritol, xylitol and glycerol.

As used herein, "x % (w/v)" is equivalent to x g/100 ml (for example 5% w/v equals 50 mg/ml).

The term "live attenuated dengue virus," also referred to as "LAV" herein, means the ability of the dengue virus to cause disease is reduced compared to wild-type dengue virus. One skilled in the art would understand that viruses may undergo mutation when cultured, passaged or propagated. The LAV may contain these naturally occurring mutations, in addition to mutations introduced for cloning purposes. The LAV may be a homogenous or heterogeneous population with none, or one or more of these mutations.

The term "live attenuated chimeric virus" (alternatively "live attenuated chimeric flavivirus") or "LACV" refers to a live attenuated chimeric virus wherein the viral genome comprises a backbone of a first flavivirus (including C, NS1, NS2A, NS2B, NS3, NS4A, NS4B and NS5 genes) and the preMembrane (prM) and envelope (E) genes of a second flavivirus, wherein the second flavivirus is selected from DENV1, DENV2, DENV3 or DENV4. The first flavivirus can be a different dengue serotype or another flavivirus, such as yellow fever virus.

The term "Δ30 LAV" refers to a live attenuated DEN1, DEN2, DEN3, or DEN4 virus, wherein the LAV comprises a viral genome that contains a deletion of about 30 nucleotides (nt) corresponding to the TL2 stem-loop structure of the 3' untranslated (UTR) region from about nt 143 to about nt 172, which reduces the replicative capacity of the virus (see WO 03/092592 and Whitehead et al., U.S. Pat. No. 8,337,860).

The term "Δ30 LACV" refers to a live attenuated chimeric flavivirus (LACV) from DENV 1-4 wherein the LACV comprises a viral genome that contains a deletion of about 30 nt corresponding to the TL2 stem-loop structure of the 3' UTR region from about nt 143 to about nt 172, which reduces the replicative capacity of the virus (see WO 03/092592 and Whitehead et al., U.S. Pat. No. 8,337,860).

The term "Δ30/Δ31 LAV" refers to a live attenuated DEN1, DEN2, DEN3, or DEN4 virus, wherein the viral genome comprises a deletion of about 30 nt of the TL2 stem-loop structure of the 3' UTR, and further comprises a separate, noncontiguous, upstream deletion of about 31 nt at about nt 258-228 of the 3' UTR which removes sequence up to and including the TL-3 homologous structure so that the deletion extends as far as the 5' boundary of the TL-3 homologous structure of the dengue 3'UTR. See Whitehead et al., U.S. Pat. No. 8,337,860. In preferred embodiments of the invention, the DEN3 LAV comprises the Δ30/Δ31 mutations.

The term "Δ30/Δ31 LACV" refers to a live attenuated chimeric DEN1, DEN2, DEN3, or DEN4 virus as described above, wherein the viral genome of the chimeric virus comprises a 30 nt deletion of the TL2 stem-loop structure of the 3' UTR, and further comprises a separate, noncontiguous, upstream 31 nt deletion of the 3' UTR, which deletes the TL-3 structure, as described above.

The term "LATV" or "live attenuated tetravalent dengue vaccine" or "LATV vaccine" refers to a vaccine comprising an effective amount of a DEN1 LAV or LACV, a DEN2 LAV or LACV, a DEN3 LAV or LACV and a DEN4 LAV or LACV. In one embodiment, at least one of the dengue LAVs or LACVs comprises the Δ30 mutation of the TL-2 structure in the 3' UTR, as described above and in WO 03/092592. In some preferred embodiments, the LATV comprises the following features: (1) rDEN1Δ30, which is a DENV1 LAV wherein the DENV1 viral genome comprises a 30 nt deletion corresponding to the TL2 stem-loop structure in the 3' UTR; (2) rDEN2/4Δ30, which is a DENV2 LACV comprising the DENV2 prM and E genes on a DENV4 backbone, wherein the DEN4 backbone comprises a 30-nt deletion corresponding to the TL2 stem-loop structure in the 3' UTR; (3) rDEN3Δ30/Δ31, which is a DENV3 LAV wherein the DENV3 viral genome comprises a 30 nt deletion corresponding to the TL2 stem-loop structure in the 3' UTR and a separate, noncontiguous, upstream 31 nt deletion corresponding to the TL-3 structure of the 3' UTR; and (4) rDEN4Δ30, which is a DENV4 LAV wherein the DENV4 viral genome comprises a 30 nt deletion corresponding to the TL2 stem-loop structure in the 3' UTR (see FIG. 1 of WO2016106107).

"Non-replicating vaccine" refers to a dengue virus vaccine for the prevention or treatment of dengue virus infection or the clinical symptoms thereof, selected from a recombinant subunit vaccine, an inactivated vaccine, a conjugate vaccine, or a DNA vaccine.

"Inactivated vaccine" refers to a vaccine comprising an effective amount of a killed or inactive whole dengue virus and a pharmaceutically acceptable carrier, wherein the virus is inactivated by any means, including with chemicals, heat or radiation. An inactivated vaccine has a low residual infectivity following inactivation, e.g. <5 plaque forming units PFU's)/mL after inactivation. In preferred embodiments, there is very low amount of residual infectivity following inactivation, e.g. ≤4 PFU's/mL, ≤3 PFU's/mL, or ≤2 PFU's/mL, <1 PFU/mL, ≤0.5 PFU/mL, or ≤0.1 PFU/mL. The PFU's of a particular vaccine may be determined, for example, by using a plaque assay, an immunostaining assay, or other method known in the art for detecting viral infectivity.

"Conjugate vaccine" refers to a vaccine comprising a dengue antigen covalently attached to a carrier protein.

A "DNA vaccine" is a vaccine comprising a sequence of nucleotides that encodes a dengue protein antigen, including dengue proteins, dengue protein fragments, and dengue fusion proteins, and variants thereof. DNA vaccines comprise a plasmid (e.g. a DNA or viral plasmid) comprising a sequence of nucleotides that encode an antigen of interest, operably linked to a promoter.

"Subunit vaccine" refers to a vaccine that includes one or more dengue antigen components, but not complete dengue viruses, such as dengue immunogenic epitopes, dengue proteins, dengue antigen fusion proteins, including fusions of different dengue serotype antigens, or dengue protein fragments. Subunit vaccines, as used herein, can be monovalent (comprise a single dengue antigen) or multivalent (comprise more than one antigen component). In preferred embodiments, the subunit vaccine is tetravalent.

The term "prime-boost" refers to a therapeutic regimen comprising (1) administration to a patient in need thereof a first dengue virus vaccine composition, wherein the composition comprises (a) at least one live attenuated dengue virus (LAV) or live attenuated chimeric flavivirus (LACV), and (b) a pharmaceutically acceptable carrier; (2) waiting for a predetermined amount of time to pass; and (3) administration to the patient of a second dengue virus vaccine composition or non-replicating dengue vaccine. The second dengue virus vaccine composition can be the same or different from the first dengue virus vaccine composition. In one embodiment, the second dengue virus vaccine is a live attenuated dengue vaccine or a recombinant dengue subunit vaccine. The dengue virus vaccines used in the compositions of the invention are useful for inducing a virus neutralizing antibody response to the homologous dengue viruses in human patients.

The term "treatment" refers to both therapeutic treatment and prophylactic or preventative measures. Individuals or patients "in need of" treatment include those already with a dengue infection, whether or not manifesting any clinical symptoms, as well as those at risk of being infected with dengue. Treatment of a patient with the dengue vaccine compositions of the invention includes one or more of the following: inducing/increasing an immune response against dengue in the patient, inducing a virus neutralizing antibody response against one or more dengue viruses, preventing, ameliorating, abrogating, or reducing the likelihood of the clinical manifestations of dengue in patients who have been infected with dengue, preventing or reducing the likelihood of developing dengue fever, DHF, or DSS and/or other disease or complication associated with dengue infection, reducing the severity or duration of the clinical symptoms of dengue infection and/or other disease or complication associated with dengue, and preventing or reducing the likelihood of dengue infection.

The term "pharmaceutically effective amount" or "effective amount" means sufficient vaccine composition is introduced to a patient to produce a desired effect, including, but not limited to: inducing/increasing an immune response against dengue in the patient, inducing/increasing a virus neutralizing antibody response against dengue in a patient, preventing or reducing the likelihood of dengue infection, preventing or reducing the likelihood of dengue recurrent infection, preventing, ameliorating or abrogating the clinical manifestations of dengue infection in patients who have been infected with dengue, preventing dengue fever, DHF and/or DSS, or reducing the severity or duration of disease associated with dengue. One skilled in the art recognizes that this level may vary.

The term "immune response" refers to a cell-mediated (T-cell) immune response and/or an antibody (B-cell) response.

The term "patient" refers to a mammal capable of being infected with a dengue virus, such as DEN1, DEN2, DEN3, or DEN4, that is to receive the dengue vaccine compositions described herein, including both immunocompetent and immunocompromised individuals. In preferred embodiments, the patient is a human. As defined herein, a "patient" includes those already infected with dengue, either through natural infection or vaccination or those that may subsequently be exposed.

An "ISCOM-like adjuvant" is an adjuvant comprising an immune stimulating complex (ISCOM), which is comprised of a saponin, cholesterol, and a phospholipid, which together form a characteristic caged-like particle, having a unique spherical, caged-like structure that contributes to its function (for review, see Barr and Mitchell, *Immunology and Cell Biology* 74: 8-25 (1996)). This term includes both ISCOM™ adjuvants, which are produced with an antigen and comprise antigen within the ISCOM™ particle and ISCOM™ matrix adjuvants, which are hollow ISCOM-type adjuvants that are produced without antigen. In preferred embodiments of the compositions and methods provided herein, the ISCOM-type adjuvant is an ISCOM™ matrix particle adjuvant, such as ISCOMATRIX™, which is manufactured without antigen (ISCOM™ and ISCOMATRIX™ are registered trademarks of CSL Limited, Parkville, Australia).

The designation "rDEN1Δ30-1545" refers to a recombinant dengue 1 virus wherein the viral genome comprises (1) a 30 nt deletion of the TL2 stem-loop structure of the 3' UTR and (2) a substitution at nucleotide position 1545 to G, which occurred after adaptation of the virus to growth in Vero cells.

The designation "rDEN2/4Δ30(ME)-1495,7163" refers to a recombinant chimeric dengue 2/4 virus, wherein the viral genome comprises: (1) a dengue 4 backbone (C, NS1, NS2A, NS2B, NS3, NS4A, NS4B, NS5 genes) comprising (i) a 30 nt deletion of the TL2 stem-loop structure of the 3' UTR, and (ii) substitutions at nucleotide position 1495 to U and 7163 to C, which occurred after adaptation of the virus to growth in Vero cells, and (2) dengue 2 prM and E genes.

The designation "rDEN3Δ30/31-7164" refers to a recombinant dengue 3 virus wherein the viral genome comprises: (1) a 30 nt deletion of the TL2 stem-loop structure of the 3' UTR, (2) a separate, 31 nt deletion in the 3'UTR, upstream of the Δ30 mutation, that deletes the TL-3 structure and (3) a substitution at nucleotide position 7164 to C, which occurred after adaptation of the virus to growth in Vero cells.

The designation "rDEN4Δ30-7132,7163,8308" refers to a recombinant dengue 4 virus wherein the viral genome comprises: (1) a 30 nt deletion of the TL2 stem-loop structure of the 3' UTR and (2) substitutions at nucleotide position 7132 to U, 7163 to C and 8308 to G, which occurred after adaptation of the virus to growth in Vero cells.

"V180" refers to a tetravalent subunit vaccine comprised of truncated envelope glycoproteins (DEN-80E) from each of the 4 dengue virus serotypes (DENV1, DENV2, DENV3, and DENV4), wherein the E proteins each constitute approximately 80% of the length of wild type E starting from amino acid residue 1 at its N-terminus, such that said E protein is secretable into growth medium when expressed recombinantly in a host cell. See Coller et al. WO 2012/154202.

The following abbreviations are used herein and have the following meanings: C is the dengue capsid gene, DEN (alternatively DENV) is dengue virus, DF is dengue fever, DHF is dengue hemorrhagic fever, DSS is dengue shock syndrome, h is hours, GMT is geometric mean titer, IM is intramuscular, IMX is Iscomatrix™, JE is Japanese encephalitis, LAV is live attenuated virus, NS (used in NS1-NS5) is non-structural, nt is nucleotide, PFU is plaque forming units, prM is the dengue preMembrane gene, SC is subcutaneous, TBE is tick-borne encephalitis, UTR is untranslated region, WN (alternatively WNV) is West Nile Virus, YF (alternatively YFV) is yellow fever virus, and wt is wild type.

Live Attenuated Dengue Virus Vaccine

As stated above, the dengue virus vaccine compositions of the invention comprise a live attenuated dengue vaccine comprising at least one LAV, selected from the group consisting of dengue virus type 1 (DEN1), dengue virus type 2 (DEN2), dengue virus type 3 (DEN3) and dengue virus type 4 (DEN4), or LACV. In one embodiment, the LAV or LACV comprises a viral genome that comprises a TL-2 Δ30 modification in the 3'UTR, and wherein the LAV or LACV: induces an immune response against dengue, induces a virus neutralizing antibody response against dengue, protects against or reduces the likelihood of infection or reduces the severity or duration of the clinical manifestations thereof. In embodiments of the invention, the live attenuated dengue vaccine is monovalent, bivalent, trivalent or tetravalent, i.e. induces an immune response against or protects against one, two, three or four of DEN serotypes 1-4, respectively. In preferred embodiments of the invention, the live attenuated dengue vaccine is tetravalent, i.e. induces an immune response against or protects against DEN serotypes 1-4 and comprises a DEN1, a DEN2, a DEN3 and a DEN4 component, wherein each component is either an LAV or an LACV.

In additional embodiments of the invention, the live attenuated dengue vaccine is a tetravalent LAV or "LATV" (i.e. comprises live attenuated dengue viruses from DENV 1-4, or live attenuated chimeric flaviviruses from DENV 1-4, as defined herein, or a combination thereof, wherein at least one of the LAVs or LACVs is a Δ30LAV or a Δ30LACV). In additional embodiments of the invention, the live attenuated dengue vaccine is tetravalent and comprises at least one chimeric flavivirus; wherein the chimeric flavivirus comprises a viral genome that contains nucleotide sequences encoding the prM and E proteins of a single dengue virus serotype and nucleotide sequences encoding the capsid and non-structural proteins of a different flavivirus, wherein the chimeric flavivirus is attenuated. In some embodiments of the invention, the capsid and nonstructural proteins of the chimeric flavivirus is from a different dengue serotype than the prM and E proteins.

In some embodiments of the invention, each LAV or LACV component of a LATV of the invention comprises a live attenuated virus which is independently either an attenuated chimeric flavivirus or an attenuated dengue virus comprising the TL-2 Δ30 modification in the 3'UTR of the viral genome. Attenuation of the dengue virus is achieved through the TL-2 Δ30 modification. However, additional attenuating mutations may also be included in one or more components of the vaccine, including, but not limited to: mutations at positions 1495, 1545, 7132, 7163, 7164 and 8308. Attenuating mutations can be achieved by different techniques, including methods known in the art such as through serial passage on tissue culture or through more defined genetic manipulations. Mutations useful for attenuating dengue viruses and chimeric dengue viruses are known in the art. See, e.g. WO 02/095075, WO 2006/44857, U.S. Pat. Nos. 7,189,403, 8,337,860, WO 2003/103571, WO 2000/014245, and WO 2008/022196. Known attenuated dengue strains can also be used in the compositions herein, such as the strains described in WO 06/134433, WO 2006/134443, WO 2007/141259, WO 96/40933, WO 2000/057907, WO 2000/057908, WO 2000/057909, WO 2000/057910, and WO 2007/015783.

Preferred embodiments of the compositions of the invention comprise a tetravalent live attenuated dengue vaccine (LATV). Such tetravalent live attenuated vaccine can comprise four attenuated dengue viruses (LAVs), three LAVs and one attenuated chimeric flavivirus strain (LACV), two dengue LAVs and two LACVs, one dengue LAV and three LACVs, or four LACVs.

In preferred embodiments, the LATV comprises the following features: (1) rDEN1Δ30, which is a DENV1 LAV wherein the DENV1 viral genome comprises a 30 nt deletion corresponding to the TL2 stem-loop structure in the 3' UTR; (2) rDEN2/4Δ30, which is a DENV2 LACV comprising the DENV2 prM and E genes on a DENV4 backbone, wherein the DEN4 backbone comprises a 30-nt deletion corresponding to the TL2 stem-loop structure in the 3' UTR; (3) rDEN3 Δ30/Δ31, which is a DENV3 LAV wherein the DENV3 viral genome comprises a 30 nt deletion corresponding to the TL2 stem-loop structure in the 3' UTR and a separate, noncontiguous, upstream 31 nt deletion corresponding to the TL-3 structure of the 3' UTR; and (4) rDEN4Δ30, which is a DENV4 LAV wherein the DENV4 viral genome comprises a 30 nt deletion corresponding to the TL2 stem-loop structure in the 3' UTR.

In embodiments of the invention comprising chimeric flaviviruses, each chimeric flavivirus comprises a viral genome that comprises nucleotide sequences encoding the prM and E proteins of a single dengue virus serotype and nucleotide sequences that encode the capsid and non-structural proteins (i.e. "the backbone") of a different flavivirus, wherein each of the chimeric flaviviruses are attenuated. Methods for construction of a recombinant live attenuated flavivirus strain may comprise the use of a known attenuated strain as a base, wherein the method comprises substituting the appropriate genes (prM and E) from a related virus of interest for the equivalent genes of the base virus. For example, this approach has been used for WNV wherein the chimeric virus is an intertypic chimeric based on an attenuated DEN-4 strain comprising prM and E genes of WNV (Bray, M. et al., *J. Virol.* (1996) 70:4162-4166; Chen, W., et al., *J. Virol.* (1995) 69:5186-5190; Bray, M. and Lai, C.-J., *Proc. Natl. Acad. Sci. USA* (1991) 88:10342-10346; Lai, C. J. et al., *Clin. Diagn. Virol.* (1998) 10:173-179).

Another approach has been the use of the YF 17D attenuated yellow fever strain as a base to develop recombinant chimeric vaccines, which was previously used for JE virus, DEN viruses, and WN virus. A chimeric yellow fever vaccine can be constructed comprising a yellow fever backbone by replacing the genes coding for prM and E proteins from any yellow fever strain, for example, YFV 17D, with those of a Dengue serotype. After DNA cloning, RNA is transcribed and transfected into Vero cells to obtain chimeric viruses possessing the YFV 17D replication machinery and the external coat of the relevant Dengue virus. See Guirakhoo et al., *Journal of Virology,* 74(12): 5477-5485 (2000); Guy et al., *Vaccine* 28: 632-649 (2010); Monath T. P. *Adv Virus Res* (2003) 61:469-509; Monath et al. *Proc. Natl. Acad. Sci. USA* (2006) 103:6694; and WO 98/37911. Thus, in some embodiments of the invention, the live attenuated dengue vaccine comprises (1) at least one chimeric flavivirus comprising the prM and E proteins of a single dengue serotype and a yellow fever backbone and (2) at least one LAV or LACV which comprises a viral genome comprising a 30-nucleotide deletion of the TL-2 stem-loop structure of the 3'UTR.

Chimeric live attenuated flaviviruses useful in the compositions of the invention may also comprise a dengue chimeric virus, wherein the viral genome comprises prM and E genes of a single dengue virus serotype and the capsid and nonstructural genes of a different dengue virus serotype. In embodiments wherein the chimeric virus comprises a backbone from a second dengue serotype, the dengue backbone comprises a deletion of about 30-nucleotides of the 3'UTR that corresponds to the TL-2 stem-loop structure and may optionally comprise additional attenuating mutations. Any attenuated dengue virus or wild-type dengue virus can be used as the backbone of the chimeric virus, by introduction of a 30-nucleotide deletion of the TL-2 stem-loop structure to an attenuated dengue backbone or wild-type dengue viral backbone. Attenuation of a dengue virus backbone can be achieved through serial passage, through the introduction of defined genetic mutations, or through the use of known attenuated dengue strains. Dengue chimeric vaccines are described, for example, in Whitehead et al. WO 03/092592. In some embodiments of the invention, the live attenuated vaccine comprises a chimeric flavivirus wherein the capsid and nonstructural proteins are from a different dengue serotype than the prM and E proteins.

The dengue virus vaccine compositions of the invention comprise an effective amount of live attenuated virus vaccine. In some embodiments of the invention, the potency of the live attenuated dengue vaccine is from 10 to about $1\times10^7$ plaque forming units (PFU's). In alternative embodiments, the potency of the live attenuated dengue vaccine is from about $1\times10^2$ to about $1\times10^6$ PFU's. In other embodiments, the potency of the live attenuated dengue vaccine is from about $1\times10^3$ to about $1\times10^5$ PFU's.

Viral plaque assays determine the number of plaque forming units (pfu) in a virus sample. Briefly, in a dengue immunoplaque assay, a confluent monolayer of host cells (e.g., Vero cells) is infected with dengue virus at varying dilutions and covered with a semi-solid overlay medium, containing methylcellulose, to prevent the virus infection from spreading indiscriminately. The virus infected cell(s) will lyse and spread the infection to adjacent cells where the infection-to-lysis cycle is repeated. The infected cells will form a plaque (a group of infected Vero cells surrounded by uninfected cells) which can be seen visually after fixing and immune-staining using anti dengue serotype specific monoclonal antibodies (mAb). Plaques are counted and the results, in combination with the dilution factors, are used to calculate the number of plaque forming units per mL (pfu/mL) in the samples. The dengue potency result in pfu/mL represents the number of infectious particles within the sample and is based on the assumption that each plaque formed is representative of one infectious virus particle.

Dengue Subunit Vaccine

In some embodiments of the invention, the formulations further comprises a recombinant dengue subunit vaccine which comprises one or more dengue antigen proteins. In preferred embodiments of this aspect of the invention, the recombinant dengue subunit vaccine comprises one or more dengue proteins, fusion proteins, or a fragment or fragments thereof. In further preferred embodiments, the recombinant dengue subunit vaccine comprises dengue envelope or E protein, or a fragment thereof.

In further preferred embodiments, the recombinant dengue subunit vaccine is tetravalent, i.e. targets an immune response against all four dengue serotypes. A recombinant dengue subunit vaccine can comprise four recombinant dengue proteins or less than four, e.g. a recombinant DEN1 protein, a recombinant DEN2 protein, and a recombinant DEN3/4 fusion protein. In some embodiments, the recombinant dengue subunit vaccine comprises dengue virus envelope glycoprotein, or fragments thereof, of DEN1-4 (e.g.

DEN1-80E, DEN2-80E, DEN3-80E, DEN4-80E, or DEN4-80EZip) that is produced and secreted using a recombinant expression system. Said subunit vaccine may optionally comprise an adjuvant, as described more fully below.

In some embodiments of this aspect of the invention, the recombinant dengue subunit vaccine comprises one or more purified dengue virus envelope ("E") proteins, a pharmaceutically acceptable excipient, wherein the E proteins each constitute approximately 80% of the length of wild type E starting from amino acid residue 1 at its N-terminus, such that said E protein is secretable into growth medium when expressed recombinantly in a host cell and wherein the composition induces the production of neutralizing antibodies in human subjects. In some embodiments of the invention, the recombinant dengue subunit vaccine further comprises an effective amount of an adjuvant. In some embodiments of the invention, the DEN-4 E protein is dimeric ("DEN4-80EZip"), as described in U.S. Pat. No. 6,749,857 and WO 2012/154202.

In some embodiments of this aspect of the invention, the E proteins in the composition described above are recombinantly produced and expressed in insect host cells. In further preferred embodiments, the E protein is recombinantly produced and expressed in *Drosophila melanogaster* Schneider 2 (S2) host cells.

The recombinant dengue virus E proteins of can be produced by means of a cell culture expression system that uses *Drosophila* Schneider 2 (S2) cells. This system has been demonstrated to produce recombinant dengue envelope proteins that maintain native-like structure (Cuzzubbo et al., *Clin. Diagn. Lab. Immunol.* (2001) 8:1150-55; Modis et al., *Proc. Natl. Acad. Sci.* (2003) 100:6986-91; Modis et al., *Nature* (2004) 427:313-9; Zhang et al., *Structure* (2004) 12(9):1607-18). This expression system has also been shown to express other recombinant envelope proteins from other flaviviruses such as West Nile, Japanese Encephalitis, hepatitis C, and Tick Borne Encephalitis viruses. The recombinant dengue envelope proteins may be truncated at the C-terminus, leaving 80% of the native envelope protein ("80E"). Thus 80E is defined as approximately the first 80% of consecutive amino acids of E protein starting at amino acid 1 of its N-terminus.

As stated above, some embodiments of this aspect of the invention comprise truncated 80E proteins which consist of approximately 80% of the length of wild type E starting from amino acid residue 1 at its N-terminus. The E proteins used in some embodiments of the invention delete the membrane anchor portion (approximately the last 10% of E at the carboxy end) of the protein. In other words, truncated 80E proteins of use in specific embodiments of the invention consist of up to the first 90% of consecutive amino acids of E starting at amino acid 1 of its N-terminus, thus allowing it to be secreted into the extracellular medium, facilitating recovery. The truncation may further delete the "stem" portion of the E protein that links the 80E portion with the membrane anchor portion; the stem portion does not contain notable antigenic epitopes and therefore is not included in the preferred antigens, DEN1-80E, DEN2-80E, DEN3-80E, DEN4-80E, or DEN4-80EZip. More than 90%, but less than 100%, of the E protein can be cloned and secreted, i.e., the protein can be 90%+ in length, carboxy truncated, and can include a portion of the membrane spanning domain so long as the truncated E protein is secretable. "Secretable" means able to be secreted, and typically secreted, from the transformed cells in the expression system. Thus, one of skill in the art will realize that dengue E proteins that are useful in the compositions and methods of the present invention may vary from the 80% exemplified herein, as long as the protein is secretable. In preferred embodiments of each aspect of the present invention, the DEN E proteins are about 80% in length starting from the N-terminal amino acid of the envelope protein and ending at an amino acid in the range of the $393^{rd}$ to $401^{st}$ amino acid, for example, from amino acid 1 to amino acid 395 of dengue virus type 2. In alternative embodiments of each aspect of the invention, the dengue E protein may be about 75%, about 85%, about 90%, about 95%, or about 98% of the consecutive amino acids of E starting at amino acid 1 of its N-terminus. In exemplary embodiments of aspects of the invention herein, the DEN E protein is approximately 80% of consecutive amino acids of E protein starting at amino acid 1 of its N-terminus; such as DEN1-80E, as set forth in SEQ ID NO:1, DEN2-80E, as set forth in SEQ ID NO:2, DEN3-80E, as set forth in SEQ ID NO:3 and DEN4-80E, as set forth in SEQ ID NO:4.

The secreted E protein may further contain domains which facilitate dimerization, such as in the DEN4-80EZip protein, such that the immunogenicity of the recombinant protein is further enhanced. An exemplary DEN4-80EZip protein comprises an amino acid sequence as set forth in SEQ ID NO:5. In some embodiments of this aspect of the invention, the DEN1, DEN2, and DEN3 80E antigens included in the composition are monomeric and the DEN4 80E antigen is dimeric.

In alternative embodiments of this aspect of the invention, the DEN1-80E, DEN2-80E, DEN3-80E and DEN4-80E proteins in the composition are monomeric. In such embodiments, the DEN4 component is present in an amount that is about 1.5 to about 3 times the individual amounts of DEN1, DEN2, and DEN3 proteins, preferably about 2 times the amount of the DEN1, DEN2, and DEN3 components (proteins). In preferred embodiments of this aspect of the invention, the ratio of DEN1:DEN2:DEN3:DEN4 antigens in the compositions is approximately 1:1:1:2.

In embodiments of the invention comprising dengue E proteins, the amount of each E protein in the composition is from about 0.5 μg to about 500 μg. In alternative embodiments, the amount of each E protein is from about 0.5 μg to about 450 μg, 0.5 μg to about 400 μg, 0.5 μg to about 350 μg, 0.5 μg to about 300 μg, 0.5 μg to about 250 μg, 0.5 μg to about 200 μg, 0.5 μg to about 150 μg, 0.5 μg to about 100 μg, 0.5 μg to about 50 μg, 5.0 μg to about 500 μg, 5.0 μg to about 450 μg, 5.0 μg to about 400 μg, 5.0 μg to about 350 μg, 5.0 μg to about 300 μg, 5.0 μg to about 250 μg, 5.0 μg to about 200 μg, 5.0 μg to about 150 μg, 5.0 μg to about 100 μg, 5.0 μg to about 50 μg, 10 μg to about 500 μg, 10 μg to about 450 μg, 10 μg to about 400 μg, 10 μg to about 350 μg, 10 μg to about 300 μg, 10 μg to about 250 μg, 10 μg to about 200 μg, 10 μg to about 150 μg, 10 μg to about 100 μg, 10 μg to about 50 μg, 25 μg to about 500 μg, 25 μg to about 450 μg, 25 μg to about 400 μg, 25 μg to about 350 μg, 25 μg to about 300 μg, 25 μg to about 250 μg, 25 μg to about 200 μg, 25 μg to about 150 μg, 25 μg to about 100 μg, or 25 μg to about 50 μg. In further preferred embodiments, the amount of each E protein in the composition is from about 1.0 μg to about 100 μg. In still further embodiments, the amount of each E protein in the composition is selected from approximately 10, 20, 30, 40, 50, 60, 70, 80, 90, 100, 150, 200, 250, 300, 350, 400, 450, or 500 μg.

Inactivated Dengue Vaccine

Inactivated dengue vaccines herein comprise one or more whole inactivated dengue viruses and/or one or more inactivated dengue chimeric viruses. In some embodiments of this aspect of the invention, the inactivated dengue vaccine is tetravalent and comprises whole inactivated DEN1, DEN2, DEN3 and DEN4. In alternative embodiments, the inactivated vaccine comprises four inactivated chimeric dengue viruses. In still other embodiments, the inactivated vaccine is tetravalent and comprises one or more whole inactivated dengue viruses and one or more inactivated dengue chimeric viruses, e.g. an inactivated whole DEN1 virus, an inactivated whole DEN2 virus, an inactivated DEN3 chimeric virus and an inactivated DEN4 chimeric virus. One of skill in the art realizes that any combination of inactivated whole or chimeric DEN viruses may be used in the tetravalent compositions and methods of the invention, as long as the vaccine composition targets all four dengue serotypes.

Inactivated dengue vaccines useful in the compositions and methods of the invention are described in Putnak et al. *Vaccine* 23: 4442-4452 (2005), U.S. Pat. Nos. 6,190,859, 6,254,873 and Sterner et al. WO 2007/002470. Alternatively, dengue virus strains and chimeric dengue strains/chimeric flavivirus strains can be inactivated for use in the compositions through methods known in the art, e.g., with chemicals, heat or radiation.

Accordingly, the present invention also relates to the above formulations comprising effective amounts of a live attenuated dengue vaccine and a non-replicating dengue vaccine, wherein the live, attenuated dengue vaccine comprises at least one live attenuated dengue virus (LAV) or at least one live attenuated chimeric flavivirus (LACV), wherein the LAV or LACV comprise a viral genome that comprises a 30-nucleotide deletion of the TL-2 stem-loop structure in the 3'UTR. In some embodiments of the invention, the non-replicating dengue vaccine of the dengue virus vaccine compositions of the invention are selected from a recombinant dengue subunit vaccine or an inactivated dengue vaccine. In one embodiment, the formulation is lyophilized, frozen, microwave dried or has lyospheres with effective amounts of a live attenuated dengue vaccine and a non-replicating dengue vaccine. In another embodiment, the formulation of live attenuated dengue vaccine is reconstituted with a liquid solution comprising the non-replicating dengue vaccine, for example V180.

In preferred embodiments of the invention, the live attenuated and the non-replicating dengue vaccines are tetravalent (i.e. comprise DEN1, DEN2, DEN3, and DEN4 components or induce an immune response against DEN1, DEN2, DEN3, and DEN4).

Adjuvants

Co-administration of vaccines with compounds that can enhance the immune response against the antigen of interest, known as adjuvants, has been extensively studied. In addition to increasing the immune response against the antigen of interest, some adjuvants may be used to decrease the amount of antigen necessary to provoke the desired immune response or decrease the number of injections needed in a clinical regimen to induce a durable immune response and provide protection from disease.

To that end, the dengue virus vaccine formulations of the invention may employ an adjuvant. The adjuvant of the formulations described herein can be any adjuvant that performs the desired function, as described above, and does not inactivate or significantly impact the titer of the LAV or LACV of the composition.

Aluminum-based compounds were determined to possess adjuvant activity over 60 years ago (for review, see Lindblad, E. B. *Immunol. and Cell Biol.* 82: 497-505 (2004); Baylor et al. *Vaccine* 20: S18-S23 (2002)). Aluminum adjuvants are generally regarded as safe when used at appropriate dosages. Many have been approved for administration into humans by regulatory agencies worldwide.

Accordingly, aluminum-based compounds, such as aluminum hydroxide ($Al(OH)_3$), aluminum hydroxyphosphate ($AlPO_4$), amorphous aluminum hydroxyphosphate sulfate (AAHS), or so-called "alum" ($KAl(SO_4) \cdot 12H_2O$) (see Klein et al., Analysis of aluminum hydroxyphosphate vaccine adjuvants by Al MAS NMR, *J. Pharm. Sci.* 89(3): 311-21 (2000)), may be combined with the compositions provided herein. In exemplary embodiments of the invention provided herein, the aluminum adjuvant is aluminum hydroxyphosphate or AAHS. In alternative embodiments, the aluminum adjuvant is an aluminum phosphate adjuvant, referred to herein as "APA". In other embodiments, the adjuvant is aluminum hydroxide.

One of skill in the art will be able to determine an optimal dosage of aluminum adjuvant that is both safe and effective at increasing the immune response to the targeted dengue viruses. For a discussion of the safety profile of aluminum, as well as amounts of aluminum included in FDA-licensed vaccines, see Baylor et al., *Vaccine* 20: S18-S23 (2002). Generally, an effective and safe dose of aluminum adjuvant varies from 50 µg to 1.25 mg elemental aluminum per dose (100 µg/mL to 2.5 mg/mL concentration).

Thus, specific embodiments of the present invention include compositions comprising a live attenuated dengue virus vaccine and further comprising an aluminum adjuvant. In embodiments of the invention, the dengue compositions comprise an adjuvant which comprises from about 50 µg to about 1.25 mg of elemental aluminum per dose of vaccine. In other embodiments, the aluminum adjuvant per dose of vaccine composition comprises an amount of elemental aluminum ranging from about 100 µg to about 1.0 mg, from about 100 µg to about 900 µg, from about 100 µg to about 850 µg, from about 100 µg to about 800 µg, from about 100 µg to about 700 µg, from about 100 µg to about 600 µg, from about 100 µg to about 500 µg, from about 100 µg to about 400 µg, from about 100 µg to about 300 µg, from about 100 to about 250 µg, from about 200 µg to about 1.25 mg, from about 200 µg to about 1.0 mg, from about 200 µg to about 900 µg, from about 200 µg to about 850 µg, from about 200 µg to about 800 µg, from about 200 µg to about 700 µg, from about 200 µg to about 600 µg, from about 200 µg to about 500 µg, from about 200 µg to about 400 µg, from about 200 µg to about 300 µg, from about 300 µg to about 1.25 mg, from about 300 µg to about 1.0 mg, from about 300 µg to about 900 µg, from about 300 µg to about 850 µg, from about 300 µg to about 800 µg, from about 300 µg to about 700 µg, from about 300 µg to about 600 µg, from about 300 µg to about 500 µg, from about 300 µg to about 400 µg, from about 400 µg to about 1.25 mg, from about 400 µg to about 1.0 mg, from about 400 µg to about 900 µg, from about 400 µg to about 850 µg, from about 400 µg to about 800 µg, from about 400 µg to about 700 µg, from about 400 µg to about 600 µg, from about 400 µg to about 500 µg, from about 500 µg to about 1.25 mg, from about 500 µg to about 1.0 mg, from about 500 µg to about 900 µg, from about 500 µg to about 850 µg, from about 500 µg to about 800 µg, from about 500 µg to about 700 µg, from about 500 µg to about 600 µg, from about 600 µg to about 1.25 mg, from about 600 µg to about 1.0 mg, from about 600 µg to about 900 µg, from about 600 µg to about 850 µg, from about 600 µg to about 800 µg, or from about 600 µg to about 700 µg.

Other adjuvants that may be used in conjunction with the dengue virus vaccine compositions of the invention, include, but are not limited to, adjuvants containing CpG oligonucleotides, or other molecules acting on toll-like receptors such as TLR4 and TLR9 (for reviews, see, Daubenberger, C. A., *Curr. Opin. Mol. Ther.* 9(1):45-52 (2007); Duthie et al., *Immunological Reviews* 239(1): 178-196 (2011); Hedayat et al., *Medicinal Research Reviews* 32(2): 294-325 (2012)), including lipopolysaccharide, monophosphoryl lipid A, and aminoalkyl glucosaminide 4-phosphates. Additional adjuvants useful in the compositions of the invention include immunostimulatory oligonucleotides s; see, e.g. U.S. Pat. Nos. 7,713,535 and 7,470,674); T-helper epitopes, lipid-A and derivatives or variants thereof, liposomes, calcium phosphate, cytokines, (e.g. granulocyte macrophage-colony stimulating factor (GM-CSF) IL-2, IFN-α, Flt-3L), CD40, CD28, CD70, IL-12, heat-shock protein (HSP) 90, CD134 (OX40), CD137, CoVaccine HT, non-ionic block copolymers, incomplete Freund's adjuvant, chemokines, cholera toxin; *E. coli* heat-labile enterotoxin; pertussis toxin; muramyl dipeptide, muramyl peptide analogues, MF59, SAF, immunostimulatory complexes, biodegradable microspheres, polyphosphazene; synthetic polynucleotides.

Additional adjuvants for use with the compositions described herein are adjuvants containing saponins (e.g. QS21), either alone or combined with cholesterol and phospholipid in the characteristic form of an ISCOM ("immune stimulating complex," for review, see Barr and Mitchell, *Immunology and Cell Biology* 74: 8-25 (1996); and Skene and Sutton, *Methods* 40: 53-59 (2006)). Such adjuvants are referred to herein as "saponin-based adjuvants". In specific embodiments of the compositions herein, the mutant toxins and/or toxin proteins are combined with an ISCOM-type adjuvant or "ISCOM", which is an ISCOM matrix particle adjuvant, such as ISCOMATRIX™, which is manufactured without antigen (ISCOM™ and ISCOMATRIX™ are the registered trademarks of CSL Limited, Parkville, Australia).

Formulations

The formulations or compositions of the invention comprise a live attenuated dengue vaccine comprising at least one live attenuated dengue virus (LAV) or at least one live attenuated chimeric flavivirus (LACY), a buffer at pH about 6.5 to 8.5, a sugar, a glycol or sugar alcohol, and a cellulose derivative selected from the group consisting of carboxymethyl cellulose, hydroxypropyl cellulose (HPC), hydroxypropyl methylcellulose (HPMC), 2-hydroxyethyl cellulose (2-HEC), crosscarmellose, and methyl cellulose, or a pharmaceutically acceptable salt thereof; optionally an alkali or alkaline salt, and optionally an amino acid selected from the group consisting of Ala, Asp, His, Leu, Lys, Gln, Pro or Glu, or a combination thereof.

In another aspect of the invention, the formulation comprises live attenuated dengue vaccine comprising at least one live attenuated dengue virus (LAV) or at least one live attenuated chimeric flavivirus at about 20-200,000,00 pfu/ml, a buffer at pH about 6.5 to 8.5, a sugar at about 150-300 mg/ml, a carrier selected from the group consisting of polyvinylpyrrolidone (PVP), carboxymethyl cellulose, hydroxypropyl cellulose (HPC), hydroxypropyl methylcellulose (HPMC), 2-hydroxyethyl cellulose (2-HEC), crosscarmellose, methyl cellulose or a pharmaceutically acceptable salt thereof, Human Serum Albumin (HSA) and gelatin; optionally an alkali salt or alkaline salt at about 5-100 mM; and optionally an amino acid Gln, Pro or Glu, or a combination thereof.

In one embodiment, the live attenuated dengue vaccine is at a concentration of 100-10,000,000 pfu/ml, 100-100,000 pfu/ml, or 600-20,000 pfu/ml in the formulation. In another embodiment, the live attenuated dengue vaccine is at a concentration of 200-200,000 pfu/ml, 600-200,000 pfu/ml, or 600-100,000 pfu/ml in the formulation.

In preferred embodiments, the cellulose derivative is anionic and forms a salt, for example carboxymethyl cellulose sodium or potassium at about 0.3-10 mg/ml, 1-10 mg/ml, 3-7 mg/ml or 5 mg/ml in the live attenuated dengue vaccine formulation. Carboxymethyl cellulose salt is available in high viscosity type with average molecular weight of about 700,000; medium viscosity type with average molecular weight of about 250,000; and low viscosity type with average molecular weight of about 90,000. In one embodiment, the cellulose derivative is carboxymethyl cellulose salt with average molecular weight of about 700,000 at about 0.3-1.5 mg/ml in the live attenuated dengue vaccine formulation. In another embodiment, the cellulose derivative is carboxymethyl cellulose salt with average molecular weight of about 250,000 at about 1-4 mg/ml. In a further embodiment, the cellulose derivative is carboxymethyl cellulose salt with average molecular weight of about 90,000 at about 3-7 or 3-10 mg/ml. In yet a further embodiment, the cellulose derivative is carboxymethyl cellulose salt with average molecular weight of about 50,000 to 1000,000 at about 0.3-10 mg/ml.

In one embodiment, the buffer is selected from the group consisting of phosphate, succinate, histidine, TRIS, MES, MOPS, HEPES, acetate and citrate at about 5-300 mM, 5-20 mM, 10-12 mM or 11 mM.

The alkali or alkaline salt can provide a stabilizing effect and can be selected from the group consisting of magnesium chloride, calcium chloride, potassium chloride, sodium chloride or a combination thereof at about 10-150 mM, 10-100 mM, 15-75 mM, 30-90 mM, 75 mM, 50 mM or 30 mM.

The amino acid can be selected from the group consisting of Val, Ile, Ala, Asp, His, Leu, Lys, Gln, Pro or Glu, or a combination thereof at 10-100, 10-75, 10-50, 20-30, or 25 mM. In another embodiment, the amino acid can be selected from the group consisting of Ala, Asp, His, Leu, Lys, Gln, Pro or Glu, or a combination thereof at 10-100, 10-75, 10-50, 20-30, or 25 mM. In one embodiment, the amino acid is Lys, Leu or Glu. In another embodiment, the amino acids are Leu and Glu. In another embodiment, the amino acid is Leu, Lys, Glu, or Ala. In another embodiment, the amino acid is Leu.

The sugar and glycol or sugar alcohol can act as a cryoprotectant or stabilizing excipient. In one embodiment, the sugar is at a concentration of 50-300 mg/ml. In another embodiment, the sugar is trehalose or sucrose or a combination thereof at about 60-120 mg/ml, 90-110 mg/ml, or 80-100 mg/ml. In one embodiment, the sucrose to trehalose ratio is between 1:1 to 1:4. In another embodiment, the sucrose is 90 mg/ml and the trehalose is 90-200 mg/ml, and preferably 110 mg/ml. In another embodiment, the glycol is propylene glycol, and the sugar alcohol is glycerol or sorbitol at about 2.5-7.5 mg/ml, 3-7 mg/ml or 5 mg/ml.

The compositions of the invention can be administered to a subject by one or more methods known to a person skilled in the art, such as parenterally, transmucosally, transdermally, intramuscularly, intravenously, intra-dermally, intranasally, subcutaneously, intra-peritonealy, and formulated accordingly.

In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like. The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

In one aspect of the invention, the formulation is a solid dried formulation prepared from lyophilization, freezing, microwave drying or through the generation of lyospheres. In one embodiment, the solid dried formulation is obtainable by or produced from the microwave drying process described in example 7. The formulations can be stored at −70° C., −20° C., 2-8° C. or at room temperature (25 or 37° C.). The dried formulations can be expressed in terms of the weight of the components in a unit dose vial, but this varies for different doses or vial sizes. Alternatively, the dried formulations of the present invention can be expressed in the amount of a component as the ratio of the weight of the component compared to the weight of the drug substance (DS) in the same sample (e.g. a vial). This ratio may be expressed as a percentage. Such ratios reflect an intrinsic property of the dried formulations of the present invention, independent of vial size, dosing, and reconstitution protocol. In other embodiments, the formulation is in lyospheres.

In another aspect of the invention, the formulation is a reconstituted solution. A dried solid formulation can be reconstituted at different concentrations depending on clinical factors, such as route of administration or dosing. For example, a dried formulation may be reconstituted at a high concentration (i.e. in a small volume) if necessary for subcutaneous administration. High concentrations may also be necessary if high dosing is required for a particular subject, particularly if administered subcutaneously where injection volume must be minimized. Subsequent dilution with water or isotonic buffer can then readily be used to dilute the drug product to a lower concentration. If isotonicity is desired at lower drug product concentration, the dried powder may be reconstituted in the standard low volume of water and then further diluted with isotonic diluent, such as 0.9% sodium chloride.

Reconstitution generally takes place at a temperature of about 25° C. to ensure complete hydration, although other temperatures may be employed as desired. The time required for reconstitution will depend, e.g., on the type of diluent, amount of excipient(s) and virus or protein. Exemplary diluents include sterile water, bacteriostatic water for injection (BWFI), a pH buffered solution (e.g. phosphate-buffered saline), sterile saline solution, Ringer's solution or dextrose solution. The reconstitution volume can be about 0.5-1.0 ml, preferably 0.5 ml or 0.7 ml. In one embodiment, a single dose has a volume of 0.5 ml. In another aspect, the invention provides a method of preparing a liquid formulation comprising the steps of reconstituting the formulations of the invention with a diluent as described above.

In another embodiment of the invention, the formulation is the aqueous solution prepared before lyophilization, freezing, microwave drying or generation of lyospheres.

Processes for Preparing the Lyospheres

Processes for preparing lyospheres are disclosed in US patent publication US20140294872, the disclosure of which is herein incorporated by reference in its entirety. The method comprises dispensing at least one liquid droplet having a substantially spherical shape onto a solid and flat surface (i.e., lacking any sample wells or cavity), freezing the droplet on the surface without contacting the droplet with a cryogenic substance and lyophilizing the frozen droplet to produce a dried pellet that is substantially spherical in shape. U.S. Pat. No. 9,119,794, the disclosure of which is herein incorporated by reference in its entirety, also discloses processes for forming lyospheres. The unitary volumes containing the aqueous medium mixture are formed on a solid element containing cavities. The solid element is cooled below the freezing temperature of the mixture, the cavities are filled with the mixture, and the mixture is solidified while present in the cavity to form the unitary forms. The unitary forms are dried in a vacuum to provide the lyospheres.

In other embodiments, the lyospheres are formed in a substantially spherical shape and are prepared by freezing droplets of a liquid composition of a desired biological material on a flat, solid surface, in particular, a surface that does not have any cavities, followed by lyophilizing the unitary forms. U.S. Patent Application Publication No. US2014/0294872, the disclosure of which is herein incorporated by reference, discloses similar processes for forming lyospheres.

Briefly, in some embodiments the process comprises dispensing at least one liquid droplet having a substantially spherical shape onto a solid and flat surface (i.e., lacking any sample wells or cavity), freezing the droplet on the surface without contacting the droplet with a cryogenic substance and lyophilizing the frozen droplet to produce a dried pellet that is substantially spherical in shape. The process may be used in a high throughput mode to prepare multiple dried pellets by simultaneously dispensing the desired number of droplets onto the solid, flat surface, freezing the droplets and lyophilizing the frozen droplets. Pellets prepared by this process from a liquid formulation may have a high concentration of a biological material (such as a protein therapeutic) and may be combined into a set of dried pellets.

In some embodiments, the solid, flat surface is the top surface of a metal plate which comprises a bottom surface that is in physical contact with a heat sink adapted to maintain the top surface of the metal plate at a temperature of −90° C. or below. Since the top surface of the metal plate is well below the freezing point of the liquid formulation, the droplet freezes essentially instantaneously with the bottom surface of the droplet touching the top surface of the metal plate.

In other embodiments, the solid, flat surface is hydrophobic and comprises the top surface of a thin film that is maintained above 0° C. during the dispensing step. The dispensed droplet is frozen by cooling the thin film to a temperature below the freezing temperature of the formulation.

Lyophilization Process

The lyophilized formulations of the present invention are formed by lyophilization (freeze-drying) of a pre-lyophilization solution. Freeze-drying is accomplished by freezing the formulation and subsequently subliming water at a temperature suitable for primary drying. Under this condition, the product temperature is below the eutectic point or the collapse temperature of the formulation. Typically, the shelf temperature for the primary drying will range from about −50 to 25° C. (provided the product remains frozen during primary drying) at a suitable pressure, ranging typically from about 30 to 250 mTorr. The formulation, size and type of the container holding the sample (e.g., glass vial) and the volume of liquid will dictate the time required for drying, which can range from a few hours to several days (e.g. 40-60 hrs). A secondary drying stage may be carried out at about 0-40° C., depending primarily on the type and size of container and the type of protein employed. The secondary drying time is dictated by the desired residual moisture level in the product and typically takes at least about 5 hours.

Typically, the moisture content of a lyophilized formulation is less than about 5%, and preferably less than about 3%. The pressure may be the same as that employed during the primary drying step. Freeze-drying conditions can be varied depending on the formulation, vial size and lyophilization trays.

In some instances, it may be desirable to lyophilize or microwave dry the formulation in the container in which reconstitution is to be carried out in order to avoid a transfer step. The container in this instance may, for example, be a 2, 3, 5, 10 or 20 ml vial.

Methods of Use

Embodiments of the invention also include one or more of the dengue vaccine compositions or formulations described herein (i) for use in, (ii) for use as a medicament or composition for, or (iii) for use in the preparation of a medicament for: (a) therapy (e.g., of the human body); (b) medicine; (c) inhibition of dengue virus replication, including DEN1, DEN2, DEN3 and/or DEN4; (d) induction of an immune response or a protective immune response against one or more of DEN1, DEN2, DEN3 and/or DEN4; (e) induction of a virus neutralizing antibody response against one or more types of dengue; (f) treatment or prophylaxis of infection by dengue virus; (g) prevention of recurrence of dengue virus infection; (h) reduction of the progression, onset or severity of pathological symptoms associated with dengue virus infection and/or reduction of the likelihood of a dengue virus infection or, (i) treatment, prophylaxis of, or delay in the onset, severity, or progression of dengue-associated disease(s), including, but not limited to: dengue fever, dengue hemorrhagic fever, and dengue shock syndrome. In these uses, the dengue vaccine compositions can optionally be employed in combination with one or more adjuvants (e.g., AAHS, aluminum phosphate, aluminum hydroxide such as Alhydrogel®, or other aluminum salt adjuvant, a saponin-based adjuvant such as ISCOMA-TRIX™ (CSL, Ltd.), a TLR-agonist, or lipid nanoparticles, described herein).

Prophylactic treatment can be performed using a dengue virus vaccine composition of the invention, as described herein. The composition of the invention can be administered to the general population or to those persons at an increased risk of dengue infection, e.g. those persons who live in or will be travelling to areas of the world in which mosquitoes of the genus *Aedes* are prevalent.

Those "in need of treatment" include those already with a dengue infection (e.g. infected with one or more of DEN1, DEN2, DEN3, or DEN4), as well as those prone to have an infection or any person in which a reduction in the likelihood of infection is desired.

Dengue virus vaccine compositions of the invention can be formulated and administered to a patient using techniques well known in the art. Guidelines for pharmaceutical administration in general are provided in, for example, Vaccines Eds. Plotkin and Orenstein, W. B. Sanders Company, 1999; *Remington's Pharmaceutical Sciences* 20$^{th}$ Edition, Ed. Gennaro, Mack Publishing, 2000; and *Modern Pharmaceutics* 2$^{nd}$ Edition, Eds. Banker and Rhodes, Marcel Dekker, Inc., 1990.

Accordingly, the invention provides a method for inducing a protective immune response in a patient against a dengue infection comprising the step of administering to the patient an immunologically effective amount of any of the dengue virus vaccine compositions described herein. In one embodiment, the dengue virus vaccine composition is co-administered in combination with other vaccines for treating or preventing diseases from Zika, Measles Mumps and Rubella, or Varicella etc.

Also provided by the invention is a method for treating dengue infection, or for treating any pathological condition associated with dengue infection, such treatment including prophylaxis of infection, and reduction in the severity of clinical symptoms, delay or prevention of the progression of disease, and/or reduction in the likelihood of infection or the clinical symptoms thereof; the method comprising the step of administering to the patient an immunologically effective amount of any of the vaccine compositions as described herein.

Additional embodiments of the invention comprise the administration of two or more compositions of the invention to a patient in a prime/boost regime. Accordingly, the invention relates to a method of preventing or reducing the likelihood of dengue infection in a patient in need thereof, comprising the steps of:

(a) administering a first dengue virus vaccine composition of the invention to the patient;
(b) waiting for a predetermined amount of time to pass after step (a);
(c) administering to the patient a second dengue virus vaccine composition of the invention; and,
(d) optionally repeating steps (b) and (c);
whereby the dengue infection is prevented or the likelihood of being infected with dengue is reduced in the patient.

In embodiments of the method above, the dengue virus vaccine compositions of the invention are in the form of a frozen liquid. In alternative embodiments, the dengue virus vaccine compositions are lyophilized, or microwaved dried and reconstituted with a sterile diluent prior to administration to the patient.

The amount of time between the first dose of a dengue virus vaccine composition of the invention and the second dose of a dengue virus vaccine composition of the invention, or any dose thereafter, is from about 2 weeks to about 2 years. In preferred embodiments of the invention, a time of 2 months to 12 months is allowed to pass between multiple administrations. In alternative embodiments of this aspect of the invention, the amount of time between each administration of each dose of vaccine composition is independently selected from the group consisting of 2 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, and 24 months.

In some embodiments of the invention, the first and second dengue virus vaccine compositions are the same. In alternative embodiments, the first and second dengue virus vaccine compositions are not the same.

The dengue virus vaccine compositions of the invention can be administered by different routes. In preferred embodiments of the invention, the compositions of the invention are administered parenterally, i.e. by intradermal, subcutaneous or intramuscular injection. Subcutaneous and intramuscular administration can be performed using, for example, needles or jet-injectors.

The compositions described herein may be administered in a manner compatible with the dosage formulation, and in such amount as is immunologically-effective to treat and/or reduce the likelihood of dengue infection. The dose administered to a patient, in the context of the present invention, should be sufficient to affect a beneficial response in a patient over time such as a reduction in the level of dengue virus, or to reduce the likelihood of infection by dengue. The quantity of the dengue virus vaccines to be administered may depend on the subject to be treated inclusive of the age, sex, weight and general health condition thereof. In this regard, precise amounts of the vaccine required to be administered will depend on the judgment of the practitioner. In determining the effective amount of the vaccine to be administered in the treatment or prophylaxis against dengue infection, the physician may evaluate circulating plasma levels, progression of disease, and the production of anti-dengue antibodies. In any event, suitable dosages of the immunogenic compositions of the invention may be readily determined by those of skill in the art.

Suitable dosing regimens are preferably determined taking into account factors well known in the art including age, weight, sex and medical condition of the patient; the route of administration; the desired effect; and the particular composition employed. The timing of doses depends upon factors well known in the art, and can range from 2 weeks to 24 months. After the initial administration one or more additional doses may be administered to maintain and/or boost antibody titers.

The invention also relates to methods for preventing dengue infection, or preventing or ameliorating the symptoms thereof, comprising the steps of: administering to a patient in which dengue infection or the symptoms thereof are to be prevented or ameliorated compositions of the dengue virus vaccine. Further embodiments of this aspect of the invention comprise allowing a predetermined amount of time to pass after administration of the dengue virus vaccine composition, and administering a second dose of a dengue virus vaccine composition.

In the method described above the first dengue vaccine is preferably tetravalent and comprises a DEN1, DEN2, DEN3, and DEN 4 component, wherein each component comprises either a live attenuated dengue virus or a live attenuated chimeric flavivirus, as described herein. In exemplary embodiments, the live attenuated dengue vaccine comprises four chimeric flaviviruses; wherein each of the chimeric flavivirus comprises the prM and E proteins of a single dengue virus serotype and the capsid and non-structural proteins of a different flavivirus, wherein the each of the chimeric flavivirus is attenuated. In certain embodiments, the capsid and nonstructural proteins of the four chimeric flaviviruses are from yellow fever virus. In alternative embodiments, the capsid and nonstructural proteins of each of the four chimeric flaviviruses are from a different dengue serotype than the prM and E proteins.

In some embodiments of this aspect of the invention, the second dengue vaccine is a tetravalent recombinant dengue subunit vaccine comprising dengue E proteins, or fragments thereof, from DEN1, DEN2, DEN3, and DEN4. Subunit vaccines useful in this method of the invention are described herein. In preferred embodiments, the E proteins each constitute about 80% of the length of wild type E of DEN1, DEN2, DEN3 and DEN4, starting from amino acid residue 1 at its N-terminus.

EXAMPLES

Examples of live attenuated dengue virus sequences used in these studies are rDEN1-rDEN1Δ30-1545 PMVS (SEQ ID NO: 6); rDEN2-rDEN2/4 Δ30(ME)-1495,7163 PMVS (SEQ ID NO: 7); rDEN3-rDEN3Δ30/31-7164 PMVS (SEQ ID NO: 8); and rDEN4-rDEN4 Δ30-7132,7163,8308 PMVS (SEQ ID NO: 9).

TABLE 1

Summary of PMVS DENV1 sequence changes

| Nucleotide Number | Gene | Nucleotide Change wt | Nucleotide Change PMVS | Protein Amino Acid Number | Amino Acid Change wt | Amino Acid Change PMVS |
|---|---|---|---|---|---|---|
| 1544* | E | A | C | 484 | Lys | Arg |
| 1545 | E | A | G | 484 | Lys | Arg |
| 1549* | E | A | G | 485 | Ser | Ser |

*Introduced for stabilization and cloning purposes

TABLE 2

Summary of PMVS DENV2 sequence changes

| Nucleotide Number | Gene | Nucleotide Change Original cDNA Clone | Nucleotide Change PMVS | Protein Amino Acid Number | Amino Acid Change Original cDNA Clone | Amino Acid Change PMVS |
|---|---|---|---|---|---|---|
| 183 | C | T | C | 28 | Leu | Leu |
| 1490 | E | G | A | 184 | Glu | Glu |
| 1495 | E | C | U | 186 | Ser | Phe |
| 7132 | NS4b | C | U | 102 | Thr | Ile |
| 7163 | NS4b | A | C | 112 | Leu | Phe |
| 7166 | NS4b | C | G | 113 | Val | Val |
| 7169 | NS4b | T | C | 114 | His | His |

TABLE 3

Summary of PMVS DENV3 sequence changes

| Nucleotide Number | Gene | Nucleotide Change wt | Nucleotide Change PMVS | Protein Amino Acid Number | Amino Acid Change wt | Amino Acid Change PMVS |
|---|---|---|---|---|---|---|
| 1539 | E | A | G | 202 | Lys | Arg |
| 1681 | E | A | G | 250 | Val | Val |
| 2095 | E | C | U | 388 | Ile | Ile |
| 7164 | NS4b | T | C | 115 | Val | Ala |
| 7304 | NS4b | T | C | 162 | Ser | Pro |
| 8082 | NS5 | A | G | 173 | Lys | Arg |
| 10533 | 3'UTR | G | A | N/A | N/A | N/A |

TABLE 4

Summary of PMVS DENV4 sequence changes

| Nucleotide Number | Gene | Nucleotide Change Original cDNA Clone | Nucleotide Change PMVS | Protein Amino Acid Number | Amino Acid Change Original cDNA Clone | Amino Acid Change PMVS |
|---|---|---|---|---|---|---|
| 2440 | NS1 | T | C | 6 | Val | Ala |
| 7132 | NS4b | C | U | 102 | Thr | Ile |
| 7153 | NS4b | T > C | U | 109 | Val > Ala | Val |
| 7163 | NS4b | A | C | 112 | Leu | Phe |
| 8308 | NS5 | A > G | G | 249 | Lys > Arg | Arg |

DENV1, 2, 3 and 4 wild type and original cDNA clone in the above tables correspond to the dengue virus serotype described in Whitehead, S. S. et al., J Virol 77:1653-1657 (2003); Blaney, J. E. et al. The American journal of tropical medicine and hygiene 71:811-821 (2004); Blaney, J. E., Jr. et al., BMC Infect Dis 4:39 (2004); Durbin, A. P. et al., The American journal of tropical medicine and hygiene 65:405-413 (2001).

The above versions of the live attenuated dengue virus are referred to as DENV1 or DEN1, DENV2 or DEN2, DENV3 or DEN3 and DENV4 or DEN4 below in the examples. For examples 1-6, the formulations had a potency of $2 \times 10^5$ pfu/ml of each of DENV1, DENV2, DENV3 or DENV4. For examples 7-10, the formulations had a potency of $1.5 \times 10^5$ pfu/ml of each of DEN1, DEN2, DEN3 or DEN4.

Example 1

Effect of CMC, PG, and Amino Acids (Compared with Dengvaxia® Formulation) on DENV4

Three separate studies were performed to investigate the effects of various excipients on the lyophilization yield and stability of DENV4. The formulations are listed in Table 5.

Study 1: DENV4 was formulated in 11 mM potassium phosphate, 90 mg/mL sucrose, and 75 mM NaCl (formulation 3), with the addition of 5 mg/mL sodium carboxymethylcellulose (sodium CMC) (formulation 4) or addition of 5 mg/mL Sodium CMC and 5 mg/mL propylene glycol (formulation 5).

Study 2: Formulation 5 was tested against comparable formulations containing either 25 mM leucine (formulation 20) or 25 mM proline (formulation 21) as well as 11 mM potassium phosphate, 90 mg/mL sucrose, 50 mM NaCl, 5 mg/mL sodium CMC and 5 mg/mL propylene glycol.

Study 3: Formulation 20 was tested against a comparable formulation containing 11 mM potassium phosphate, 90 mg/mL sucrose, 50 mM NaCl, 5 mg/mL sodium CMC and 5 mg/mL propylene glycol and 25 mM glutamic acid (for-

TABLE 5

Formulation Compositions

| Formulation Number | Composition |
|---|---|
| 1 | 11 mM potassium phosphate, 90 mg/mL sucrose, 30 mM sodium chloride pH 7.5 |
| 2 | 11 mM potassium phosphate, 90 mg/mL sucrose pH 7.5 |
| 3 | 11 mM potassium phosphate, 90 mg/mL sucrose, 75 mM sodium chloride pH 7.5 |
| 4 | 11 mM potassium phosphate, 90 mg/mL sucrose, 75 mM sodium chloride, 5 mg/mL sodium carboxymethylcellulose pH 7.5 |
| 5 | 11 mM potassium phosphate, 90 mg/mL sucrose, 75 mM sodium chloride, 5 mg/mL sodium carboxymethylcellulose, 5 mg/mL propylene glycol pH 7.5 |
| 13 | 11 mM potassium phosphate, 90 mg/mL sucrose, 25 mg/mL sorbitol, 75 mM sodium chloride, 5 mg/mL sodium carboxymethylcellulose pH 7.5 |
| 18 | 11 mM potassium phosphate, 90 mg/mL sucrose, 50 mM sodium chloride, 5 mg/mL sodium carboxymethylcellulose, 5 mg/mL propylene glycol, 25 mM L arginine pH 7.5 |
| 19 | 11 mM potassium phosphate, 90 mg/mL sucrose, 50 mM sodium chloride, 5 mg/mL sodium carboxymethylcellulose, 5 mg/mL propylene glycol, 25 mM L glutamic acid pH 7.5 |
| 20 | 11 mM potassium phosphate, 90 mg/mL sucrose, 50 mM sodium chloride, 5 mg/mL sodium carboxymethylcellulose, 5 mg/mL propylene glycol, 25 mM L leucine pH 7.5 |
| 21 | 11 mM potassium phosphate, 90 mg/mL sucrose, 50 mM sodium chloride, 5 mg/mL sodium carboxymethylcellulose, 5 mg/mL propylene glycol, 25 mM L proline pH 7.5 |
| 22 | 11 mM potassium phosphate, 90 mg/mL sucrose, 75 mM sodium chloride, 5 mg/mL sodium carboxymethylcellulose, 5 mg/mL glycerol pH 7.5 |
| 25 | 11 mM TRIS, 90 mg/mL sucrose, 75 mM sodium chloride, 5 mg/mL sodium carboxymethylcellulose, 5 mg/mL propylene glycol pH 7.5 |
| 26 | 6 mM TRIS, 37.5 mg/mL sorbitol, 75 mg/mL sucrose, 55 mg/mL trehalose, 2.5 mg/mL urea, 15 mg/mL amino acid mixture ‡ |
| 45 | 11 mM potassium phosphate, 90 mg/mL sucrose, 50 mM sodium chloride, 5 mg/mL sodium carboxymethylcellulose, 5 mg/mL propylene glycol pH 7.5 |
| 46 | 11 mM potassium phosphate, 90 mg/mL sucrose, 30 mM sodium chloride, 5 mg/mL sodium carboxymethylcellulose, 5 mg/mL propylene glycol pH 7.5 |
| 47 | 11 mM potassium phosphate, 90 mg/mL sucrose, 15 mM sodium chloride, 5 mg/mL sodium carboxymethylcellulose, 5 mg/mL propylene glycol pH 7.5 |
| 50 | 11 mM potassium phosphate, 90 mg/mL sucrose, 50 mM potassium chloride, 5 mg/mL sodium carboxymethylcellulose, 5 mg/mL propylene glycol pH 7.5 |
| 55 | 11 mM potassium phosphate, 90 mg/mL sucrose, 75 mM sodium chloride, 5 mg/mL sodium carboxymethylcellulose, 5 mg/mL glycerol, 5 mg/mL urea pH 7.5 |
| 56 | 11 mM potassium phosphate, 90 mg/mL sucrose, 201 mg/mL Leibovitz's L-15 Medium without phenol red*, 5 mg/mL sodium carboxymethylcellulose, 5 mg/mL propylene glycol pH 7.5 |
| 57 | 5.5 mM TRIS, 5.5 mM L histidine, 90 mg/mL sucrose, 50 mM sodium chloride, 5 mg/mL sodium carboxymethylcellulose, 5 mg/mL propylene glycol, 25 mM L leucine pH 7.5 |
| 81 | 11 mM potassium phosphate, 90 mg/mL sucrose, 75 mM sodium chloride, 5 mg/mL sodium carboxymethylcellulose, 5 mg/mL propylene glycol, 25 mM L leucine pH 7.5 |
| 98 | 11 mM potassium phosphate, 90 mg/mL sucrose, 50 mM sodium chloride, 5 mg/mL sodium carboxymethylcellulose, 5 mg/mL propylene glycol, 25 mM L leucine, 0.01% poloxamer 188 pH 7.5 |
| 104 | 11 mM potassium phosphate, 90 mg/mL sucrose, 50 mM sodium chloride, 5 mg/mL sodium carboxymethylcellulose, 5 mg/mL propylene glycol, 25 mM L leucine, 25 mM L glutamic acid, pH 7.5 |

*Leibovitz's L-15 medium without phenol red is a solution manufactured by Hyclone Laboratories, Inc.

mulation 19) and the Dengvaxia® formulation (formulation 26), which consists of 37.5 mg/mL sorbitol, 75 mg/mL sucrose, 55 mg/mL trehalose, 25 mg/mL urea, 6 mM TRIS, 15 mg/mL of an amino acid mixture.

For all studies, samples were frozen and a portion were stored at −70° C. as frozen liquid controls and a portion were lyophilized. After lyophilization, some samples were stored at −70° C. as control and the remainder were placed at 25° C. for 1 week. After incubation, the 25° C. samples were frozen and tested with a dengue relative infectivity assay (DRIA) along with the frozen liquid controls and frozen lyophilized controls. Two individual vials of each sample were tested.

DRIA is a cell-based relative infectivity assay used to measure infectivity of dengue virus formulation samples based on expression of envelope protein. Vero cells were plated in 96-well micro-titer plates, incubated for 24 hours, and then infected with serial dilutions of DEN1, DEN2, DEN3 and/or DEN4 reference standard and positive control specific for the serotype being tested in addition to the test articles. The infected cells were incubated for 48 hours and followed by fixation of the cells with a dilute formaldehyde solution. The fixed cells were then permeabilized before primary antibody (rabbit anti-DEN serotype-specific MAb) was added to the plates and incubated overnight. After washing the plates, secondary antibody (Donkey NL637-conjugated anti-rabbit IgG, R&D Systems) was added to the wells and incubated at room temperature for >2 hrs. After washing the plates, PBS was added to the wells in preparation for image analysis using the MiniMax imaging reader (Molecular Devices). The relative potency (% RP) of samples (relative to the reference standard) was calculated using SoftMAX Pro software (Molecular Devices) using a reduced 4 parameter logistic curve fit.

Lyophilization yields were calculated by dividing the lyophilized infectivity result by the frozen liquid control infectivity result. To calculate log loss after storage at 25° C. for one week, infectivity values were converted into log scale and the 1 week 25° C. log result was subtracted from the −70° C. lyophilized control result for each formulation.

A synergistic effect was observed with the combination of sodium CMC and propylene glycol, which resulted in improved lyophilization yield and stability. The addition of leucine further improved yield and stability. Formulations containing Sodium CMC, propylene glycol and leucine or glutamic acid provided improved lyophilization yield over the Dengvaxia formulation. See FIGS. 1-2. The 1 week 25° C. stability time point for formulation 26 was not tested due to cake collapse after storage at 25° C.

Example 2

Effect of Sugar Alcohol on DENV4:

DENV4 was formulated in a base formulation of 11 mM potassium phosphate, 90 mg/mL sucrose, 75 mM NaCl, and 5 mg/mL sodium CMC pH 7.5 with 5 mg/mL propylene glycol (formulation 5), 5 mg/mL glycerol (formulation 22), or 25 mg/mL sorbitol (formulation 13) as sugar alcohols.

Samples were frozen and a portion were stored at −70° C. as frozen liquid controls and a portion were lyophilized. After lyophilization, some samples were stored at −70° C. and the remainder were placed at 25° C. for 1 week. After incubation, the 25° C. samples were frozen and tested with a dengue relative infectivity assay along with the frozen liquid controls and frozen lyophilized controls. Two individual vials of each sample were tested.

Lyophilization yields were calculated by dividing the lyophilized infectivity result by the frozen liquid control infectivity result. To calculate log loss after storage at 25° C. for one week, infectivity values were converted into log scale and the 1 week 25° C. log result was subtracted from the −70° C. lyophilized control result for each formulation.

This example demonstrates that both propylene glycol and glycerol improved DENV4 lyophilization yield and stability compared to sorbitol (see FIGS. 3 and 4).

Example 3

Effect of pH on DENV4:

DENV4 was formulated in formulation 22 (11 mM potassium phosphate, 90 mg/mL sucrose, 75 mM NaCl, 5 mg/mL sodium CMC, 5 mg/mL glycerol at pH 7.0, 7.5 or 8.0).

Samples were frozen and a portion were stored at −70° C. as frozen liquid controls and a portion were lyophilized. After lyophilization, some samples were stored at −70° C. and the remainder were placed at 25° C. for 1 week. After incubation, the 25° C. samples were frozen and tested with a dengue relative infectivity assay along with the frozen liquid controls and frozen lyophilized controls. Two individual vials of each sample were tested.

Lyophilization yields were calculated by dividing the lyophilized infectivity result by the frozen liquid control infectivity result. To calculate log loss after storage at 25° C. for one week, infectivity values were converted into log scale and the 1 week 25° C. log result was subtracted from the −70° C. lyophilized control result for each formulation.

FIGS. 5 and 6 demonstrate that DENV4 can be formulated in formulation 22 from pH 7.0 to pH 8.0.

Example 4

Effect of buffer on DENV4:

In Study 1, DENV4 was formulated in a base formulation of 90 mg/mL sucrose, 75 mM NaCl, 5 mg/mL sodium CMC, and 5 mg/mL glycerol with alternative buffer systems adjusted to pH 7.5. Formulation 22 contained 11 mM potassium phosphate and formulation 25 contained 11 mM TRIS in addition to the base formulation.

In study 2, DENV4 was formulated in a base formulation of 90 mg/mL sucrose, 75 mM NaCl, 5 mg/mL sodium CMC, and 5 mg/mL propylene glycol with alternative buffer systems adjusted to pH 7.5. Formulation 5 contained 11 mM potassium phosphate and formulation 57 contained a combination of 5.5 mM histidine and 5.5 mM TRIS in addition to the base formulation.

Samples were frozen and a portion were stored at −70° C. as frozen liquid controls and a portion were lyophilized. After lyophilization, some samples were stored at −70° C. and the remainder were placed at 25° C. for 1 week. After incubation, the 25° C. samples were frozen and tested with a dengue relative infectivity assay along with the frozen liquid controls and frozen lyophilized controls. Two individual vials of each sample were tested.

Lyophilization yields were calculated by dividing the lyophilized infectivity result by the frozen liquid control infectivity result. To calculate log loss after storage at 25° C. for one week, infectivity values were converted into log scale and the 1 week 25° C. log result was subtracted from the −70° C. lyophilized control result for each formulation.

FIGS. 7 and 8 demonstrate that DENV4 can be formulated in a variety of buffer systems at pH 7.5 including potassium phosphate, TRIS, or a combination of histidine and TRIS.

Example 5

Effect of NaCl on DENV4:

DENV4 was formulated in a base formulation of 11 mM potassium phosphate, 90 mg/mL sucrose, 5 mg/mL sodium CMC, and 5 mg/mL propylene glycol with a concentration range of NaCl from 15-75 mM.

Samples were frozen and a portion were stored at −70° C. as frozen liquid controls and a portion were lyophilized. After lyophilization, some samples were stored at −70° C. and the remainder were placed at 25° C. for 1 week. After incubation, the 25° C. samples were frozen and tested with a dengue relative infectivity assay along with the frozen liquid controls and frozen lyophilized controls. Two individual vials of each sample were tested.

Lyophilization yields were calculated by dividing the lyophilized infectivity result by the frozen liquid control infectivity result. To calculate log loss after storage at 25° C. for one week, infectivity values were converted into log scale and the 1 week 25° C. log result was subtracted from the −70° C. lyophilized control result for each formulation.

FIGS. 9 and 10 show that DENV4 lyophilization yield and stability for 1 week at 25° C. were similar when the NaCl concentration ranged from 15-75 mM.

Example 6

Effect of Propylene Glycol and Glycerol on All Dengue Serotypes:

DENV1, DENV2, DENV3 and DENV4 were prepared as monovalent drug products in formulation 5 (11 mM potassium phosphate, 90 mg/mL sucrose, 75 mM NaCl, 5 mg/mL CMC, 5 mg/mL propylene glycol), formulation 20 (11 mM potassium phosphate, 90 mg/mL sucrose, 50 mM NaCl, 5 mg/mL CMC, 5 mg/mL propylene glycol, and 25 mM Leucine) and formulation 22 (11 mM potassium phosphate, 90 mg/mL sucrose, 75 mM NaCl, 5 mg/mL CMC, 5 mg/mL glycerol) at pH 7.5.

Samples were frozen and a portion were stored at −70° C. as frozen liquid controls and a portion were lyophilized. After lyophilization, some samples were stored at −70° C. and the remainder were placed at 25° C. for 1 week. After incubation, the 25° C. samples were frozen and tested with a dengue relative infectivity assay along with the frozen liquid controls and frozen lyophilized controls. Two individual vials of each sample were tested.

Lyophilization yields were calculated by dividing the lyophilized infectivity result by the frozen liquid control infectivity result. To calculate log loss after storage at 25° C. for one week, infectivity values were converted into log scale and the 1 week 25° C. log result was subtracted from the −70° C. lyophilized control result for each formulation.

FIGS. 11 and 12 show that propylene glycol and glycerol stabilize all four serotypes in combination with sucrose, NaCl, and Sodium CMC.

Example 7

SPG (Sucrose, Potassium Phosphate, Glutamic acid) was made as a 10× solution with the below concentration seen in the Table 6.

TABLE 6

| | |
|---|---|
| Sucrose (crystals) | 746.2 mg/mL |
| $KH_2PO_4$ (monobasic, anhydrous) | 5.17 mg/mL |
| $K_2HPO_4$ (dibasic, anhydrous) | 12.54 mg/mL |
| L-glutamic acid (monosodium salt, monohydrate) | 11.2 mg/mL |

The following other solutions were also made: 650 mg/mL Sucrose, 650 mg/mL Trehalose, dihydrate, 200 mg/mL Gelatin, 150 mg/mL Arginine, and 20 mg/mL Human Serum Albumin (HSA).

The SPG, sucrose, trehalose, gelatin, arginine, and HSA were filtered with PES 0.22 μm Stericup filters. The solutions, Leibovitz's L-15 and DEN1 were combined to obtain the final formulations seen below:

TABLE 7

| Rx# | Formulations |
|---|---|
| 1 | 250 mg/mL L-15, 11 mM Potassium Phosphate, 6 mM L-glutamic acid, 75 mg/mL Sucrose |
| 2 | 250 mg/mL L-15, 11 mM Potassium Phosphate, 6 mM L-glutamic acid, 75 mg/mL Sucrose, 175 mg/mL Trehalose |
| 4 | 250 mg/mL L-15, 11 mM Potassium Phosphate, 6 mM L-glutamic acid, 75 mg/mL Sucrose , 175 mg/mL Trehalose, 2.5 mg/mL HAS |
| 5 | 250 mg/mL L-15,11 mM Potassium Phosphate, 6 mM L-glutamic acid, 75 mg/mL Sucrose, 175 mg/mL Trehalose, 25 mg/mL Gelatin |
| 6 | 250 mg/mL L-15, 11 mM Potassium Phosphate, 6 mM L-glutamic acid, 150 mg/mL Sucrose |
| 7 | 250 mg/mL L-15, 11 mM Potassium Phosphate, 6 mM L-glutamic acid, 75 mg/mL Sucrose, 75 mg/mL Trehalose |
| 9 | 250 mg/mL L-15, 11 mM Potassium Phosphate, 6 mM L-glutamic acid, 75 mg/mL Sucrose, 75 mg/mL Trehalose, 40 mg/mL Arginine |
| 11 | 450 mg/mL L-15, 11 mM Potassium Phosphate, 6 mM L-glutamic acid, 75 mg/mL Sucrose |
| 12 | 450 mg/mL L-15, 11 mM Potassium Phosphate, 6 mM L-glutamic acid, 75 mg/mLSucrose, 175 mg/mL Trehalose, 25 mg/mL Gelatin |
| 13 | 450 mg/mL L-15, 11 mM Potassium Phosphate, 6 mM L-glutamic acid, , 75 mg/mL Sucrose, 75 mg/mL Trehalose, 40 mg/mL Arginine |

The formulations were filled into 2R glass vials at a 0.5 mL fill and frozen at −115° C. for 15 minutes. Once frozen the vials were dried in the Microwave Vacuum Dryer (MVD). Once dried, some vials were place on stability at 25° C. for 1 week. The vials were then submitted for potency testing using the Dengue Relative Infectivity Assay (DRIA).

Microwave Drying Process

Material being dried in the microwave vacuum dryer (MVD) were blast frozen and immediately loaded into the drying chamber. Vacuum was quickly pulled on the chamber to below 100 mTorr. Once the vacuum setpoint was reached, the magnetrons (i.e. number of magnetron and power output) were selected to begin drying the material. Microwave (radiation is applied in a travelling wave format) was operated in scanning mode with an algorithm that cycles selected magnetrons (e.g. 2 magnetrons out of 4 total magnetrons) on and off every 30 seconds for uniform power distribution. Furthermore, a water load on top of the unit allows for single pass of microwave through the sample that minimizes any interference from reflected microwave thereby allowing for controlled sublimation. Power was increased throughout the drying cycle to achieve a final terminal temperature of 30-45° C. Once dried, vacuum was broken in the chamber and the material was sealed.

TABLE 8

| | Rx# | | | | |
|---|---|---|---|---|---|
| | 1 | 2 | 4 | 5 | 6 |
| | | | Rx | | |
| | 250 mg/mL L-15, 11 mM Potassium Phosphate, 6 mM L-glutamic acid, 75 mg/mL Sucrose | 250 mg/mL L-15, 11 mM Potassium Phosphate, 6 mM L-glutamic acid, 75 mg/mL Sucrose, 175 mg/mL Trehalose | 250 mg/mL L-15, 11 mM Potassium Phosphate, 6 mM L-glutamic acid, 75 mg/mL Sucrose, 175 mg/mL Trehalose, 2.5 mg/mL HSA | 250 mg/mL L-15, 11 mM Potassium Phosphate, 6 mM L-glutamic acid, 75 mg/mL Sucrose, 175 mg/mL Trehalose, 25 mg/mL Gelatin | 250 mg/mL L-15, 11 mM Potassium Phosphate, 6 mM L-glutamic acid, 150 mg/mL Sucrose |
| F/T Yield (%) | 55 | 88 | 142 | 102 | 61 |
| Drying Yield (%) | 62 | 59 | 67 | 83 | 64 |
| Avg. Log Loss | 0.45 | 0.26 | 0.23 | 0.19 | 0.33 |

| | Rx# | | | | |
|---|---|---|---|---|---|
| | 7 | 9 | 11 | 12 | 13 |
| | | | Rx | | |
| | 250 mg/mL L-15, 11 mM Potassium Phosphate, 6 mM L-glutamic acid, 75 mg/mL Sucrose, 75 mg/mL Trehalose | 250 mg/mL L-15, 11 mM Potassium Phosphate, 6 mM L-glutamic acid, 75 mg/mL Sucrose, 75 mg/mL Trehalose, 40 mg/mL Arginine | 450 mg/mL L-15, 11 mM Potassium Phosphate, 6 mM L-glutamic acid, 75 mg/mL Sucrose | 450 mg/mL L-15, 11 mM Potassium Phosphate, 6 mM L-glutamic acid, 75 mg/mL Sucrose, 175 mg/mL Trehalose, 25 mg/mL Gelatin | 450 mg/mL L-15, 11 mM Potassium Phosphate, 6 mM L-glutamic acid, , 75 mg/mL Sucrose, 75 mg/mL Trehalose, 40 mg/mL Arginine |
| F/T Yield (%) | 69 | 53 | 23 | 98 | 29 |
| Drying Yield (%) | 78 | 6 | 167 | 98 | 10 |
| Avg. Log Loss | 0.35 | 3.65 | 0.36 | 0.27 | 2.11 |

Freeze/Thaw (F/T) yield, drying yield, and log loss at 25° C. for 1 week were determined for all formulations. Freeze/thaw (F/T) yield was calculated by dividing the reported relative potency by the expected relative potency for the frozen controls at −70° C. Drying yield was calculated by dividing the relative potency of the dried material by the relative potency of the frozen control. The log loss was calculated by converting the relative potency of the T0 timepoint of the dried material and the 1 week 25° C. stability material into logs by a Log 10 calculation. Once the numbers are converted into log, the stability timepoint was subtracted from the T0 timepoint to determine the log loss at 25° C. for 1 week.

Formulations 2, 4, 5, and 12 showed the best combination of F/T yield, drying yield, and log loss at 25° C. for one week. All four of these formulations contained ≥25% disaccharide (sucrose and/or trehalose).

TABLE 9 summary of ranges of excipients of formulations in Table 7

| Excipients | Quantity (per 0.5 mL dose) |
|---|---|
| Sucrose | 37.5 mg-75 mg |
| Potassium Phosphate (monobasic, anhydrous) | ~0.26 mg |
| Potassium Phosphate (dibasic, anhydrous) | ~0.63 mg |
| L-glutamic acid (monosodium salt, monohydrate) | 0.56 mg |
| Trehalose | 37.5 mg-87.5 mg |
| Human Serum Albumin (HSA) | 1.25 mg |
| Arginine | 20 mg |
| Gelatin | 12.5 mg |

Example 8

SPG (Sucrose, Potassium Phosphate, Glutamic acid) was made according to Example 7. The following other solutions were also made: 650 mg/mL Sucrose, 650 mg/mL Trehalose, 5M Sodium Chloride (NaCl), and 10 mg/mL sodium Carboxymethyl Cellulose (sodium CMC).

All solutions were filter with PES 0.22 µm Stericup filters. The solutions and Dengue virus DEN1 or DEN4 were combined to obtain the final formulations seen in the results table.

The formulations were filled into 2R glass vials at a 0.5 mL fill and frozen at −115° C. for 15 minutes. Once frozen the vials were dried in the Microwave Vacuum Dryer (MVD). Once dried, some vials were place on stability at 25° C. for 1 week. The vials were then submitted for potency testing using the Dengue Relative Infectivity Assay (DRIA).

TABLE 10

| Formulations | DEN1 Avg. Log Loss 25° C. 1 week | DEN4 Avg. Log Loss 25° C. 1 week | Residual Moisture (%) |
|---|---|---|---|
| 11 mM Potassium Phosphate, 6 mM L-glutamic acid, 75 mg/mL Sucrose, 175 mg/mL Trehalose | 0.55 | 0.55 | 5.65 ± 0.75 |
| 11 mM Potassium Phosphate, 6 mM L-glutamic acid, 75 mg/mL Sucrose, 175 mg/mL Trehalose, 30 mM NaCl | 0.46 | 0.54 | 5.61 ± 0.40 |
| 11 mM Potassium Phosphate, 6 mM L-glutamic acid, 75 mg/mL Sucrose, 175 mg/mL Trehalose, 30 mM NaCl, 5 mg/mL sodium CMC | 0.60 | 0.59 | 4.58 ± 0.33 |
| 11 mM Potassium Phosphate, 6 mM L-glutamic acid, 75 mg/mL Sucrose, 75 mg/mL Trehalose | 1.12 | 0.95 | 3.71 ± 0.22 |
| 11 mM Potassium Phosphate, 6 mM L-glutamic acid, 75 mg/mL Sucrose, 75 mg/mL Trehalose, 30 mM NaCl | 0.96 | 0.51 | 4.75 ± 0.54 |
| 11 mM Potassium Phosphate, 6 mM L-glutamic acid, 75 mg/mL Sucrose, 75 mg/mL Trehalose, 30 mM NaCl, 5 mg/mL sodium CMC | 1.07 | 0.65 | 3.98 ± 0.01 |
| 11 mM Potassium Phosphate, 6 mM L-glutamic acid, 75 mg/mL Trehalose | 0.83 | 1.82 | 2.20 ± 0.12 |
| 11 mM Potassium Phosphate, 6 mM L-glutamic acid, 75 mg/mL Trehalose, 30 mM NaCl | 1.18 | 1.33 | 3.43 ± 0.19 |

Figure 17:
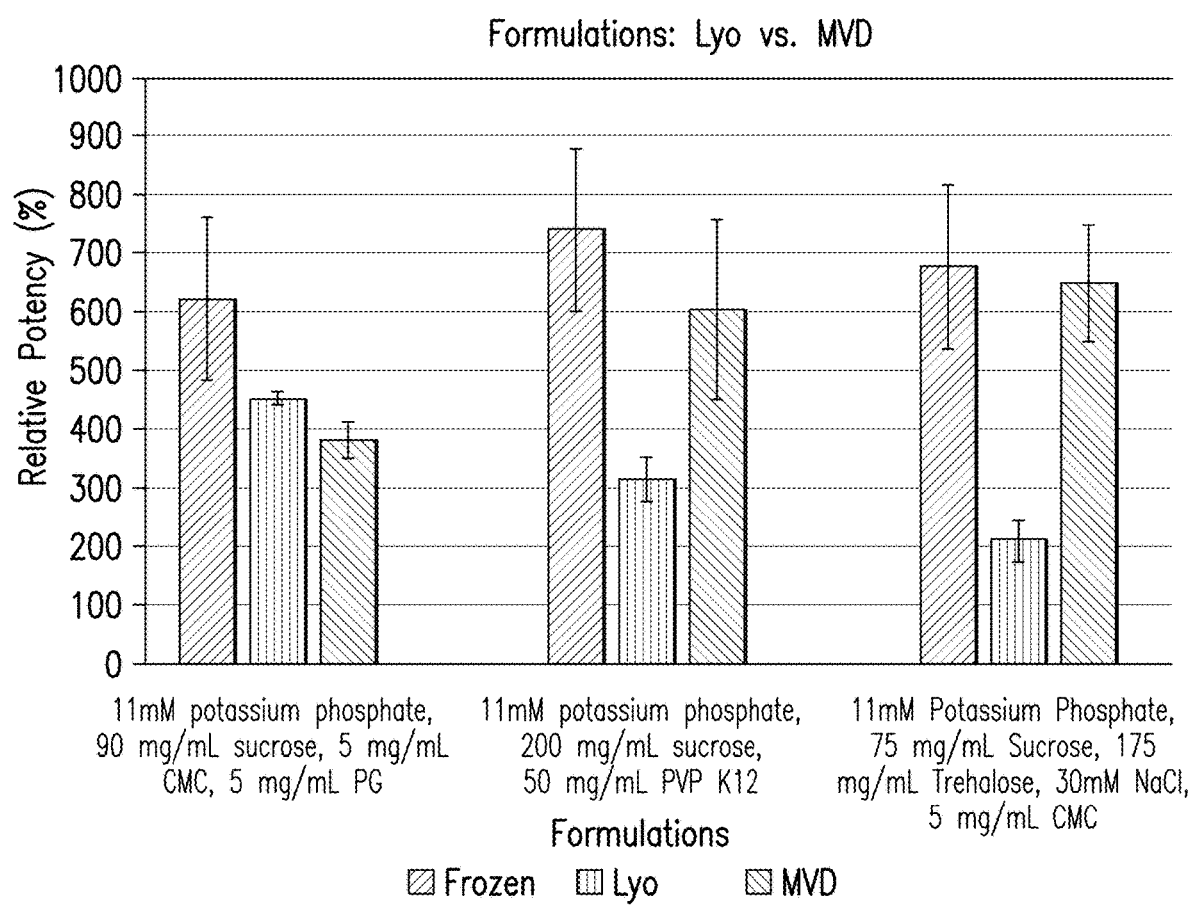
FIG. 17: Relative potency for frozen, microwave dried (MVD) and lyophilized (lyo) DEN1 formulations.
Figure 18A:
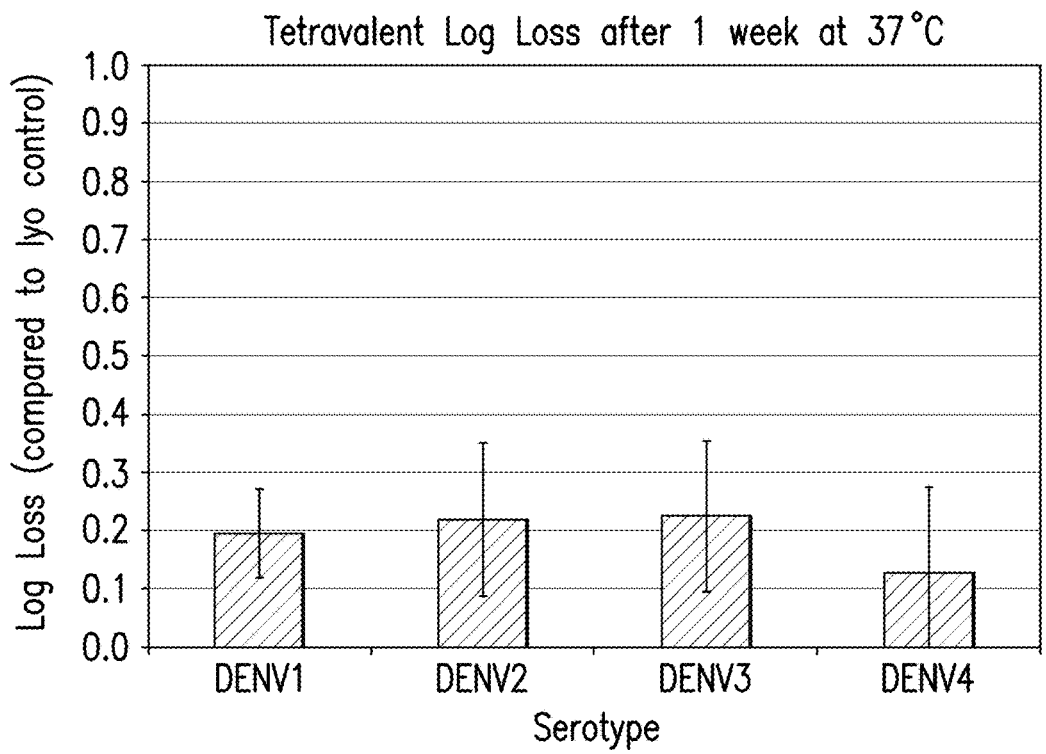
FIG. 18A-B: A) Stability of tetravalent formulations at 37° C. after one week. B) Stability of tetravalent formulations at 25° C. after one month.
Figure 18B:
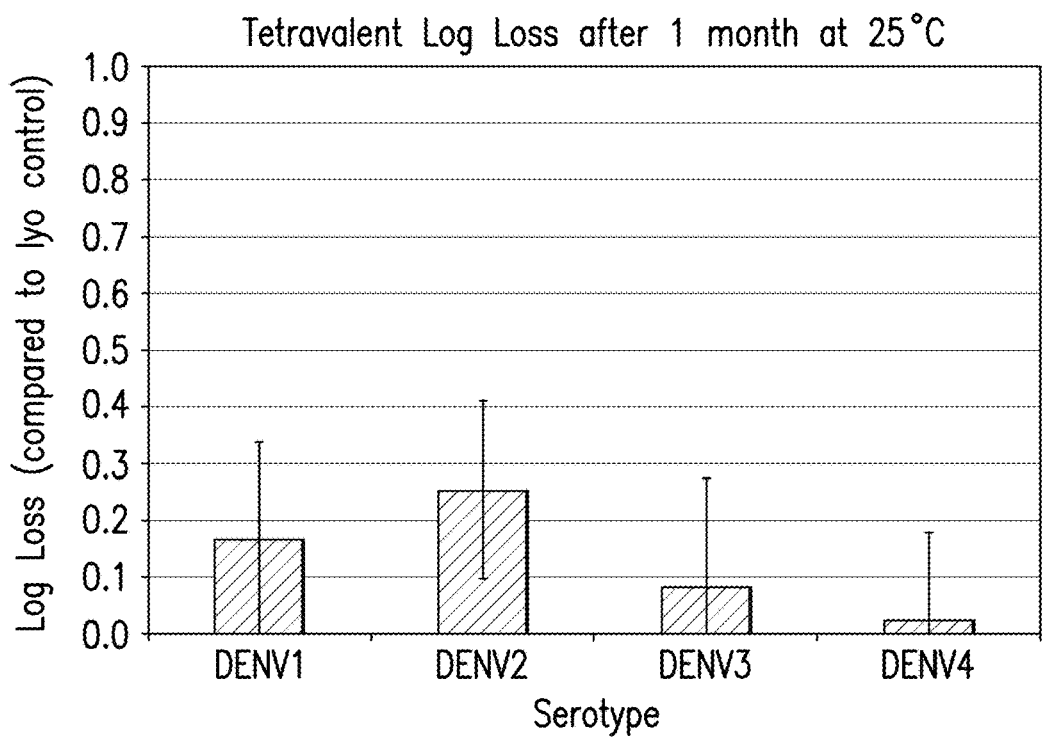
Figure 19A:
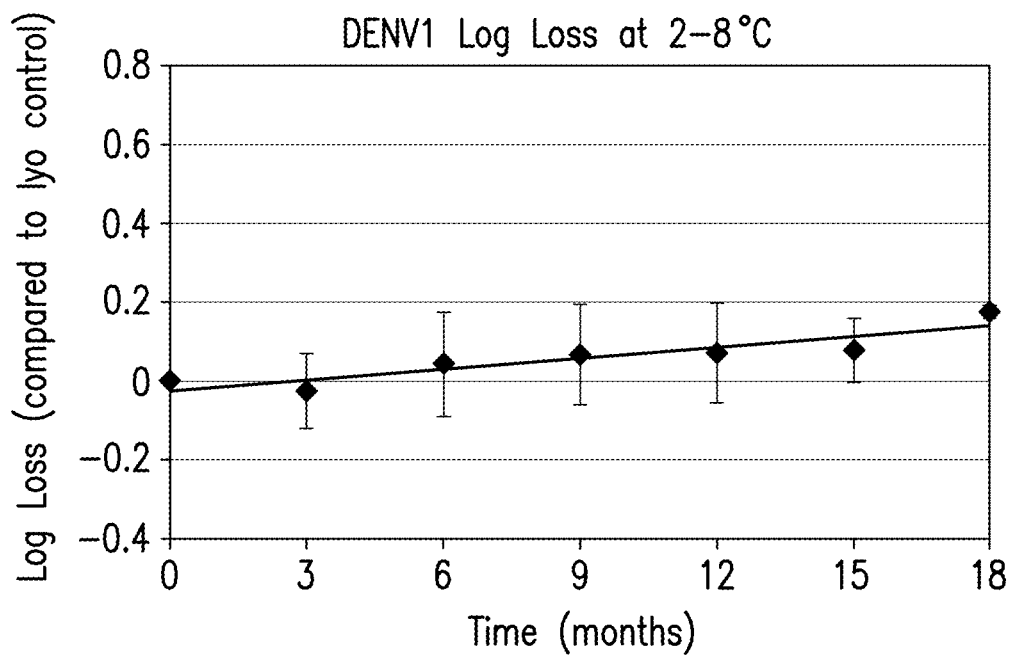
FIG. 19A-D: Stability of tetravalent formulations (DEN1-DEN4) at 2-8° C. tested every 3 months up to 18 months.
Figure 19B:
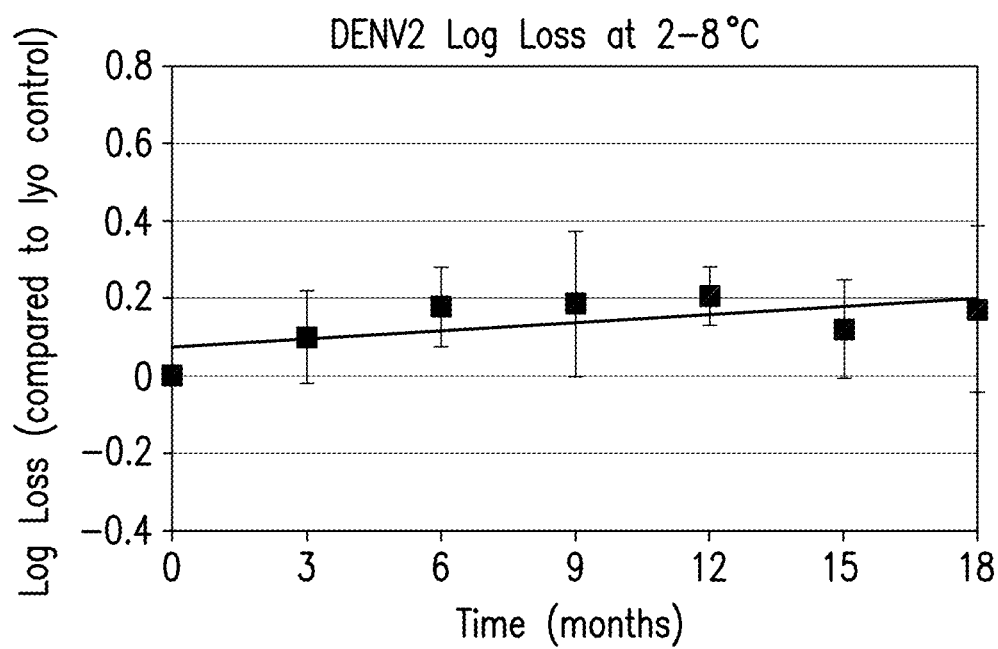
Figure 19C:
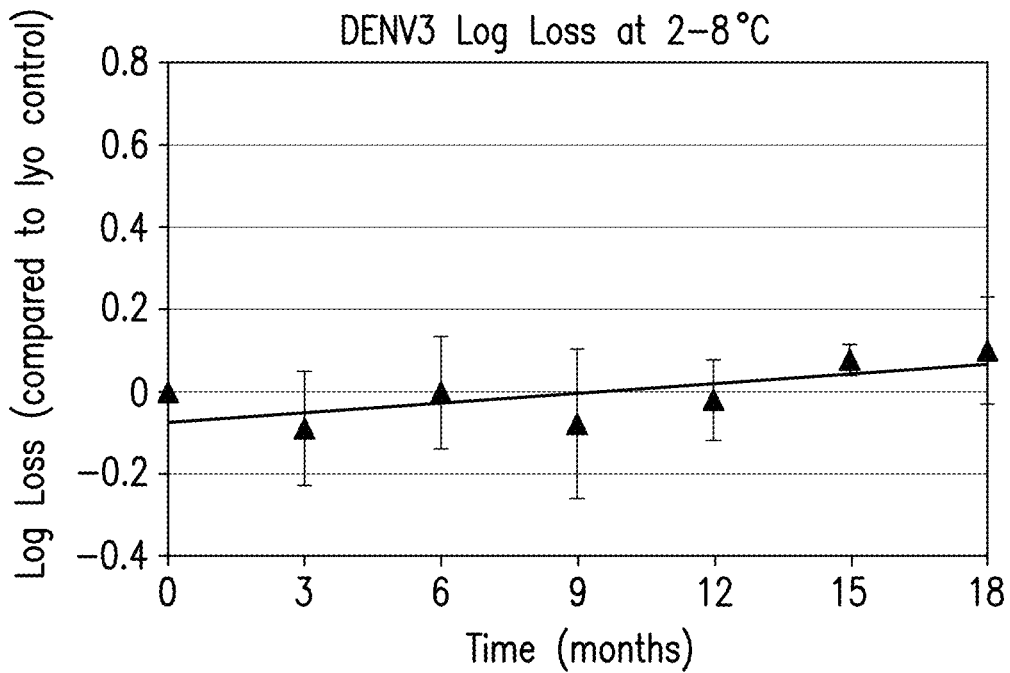
Figure 19D:
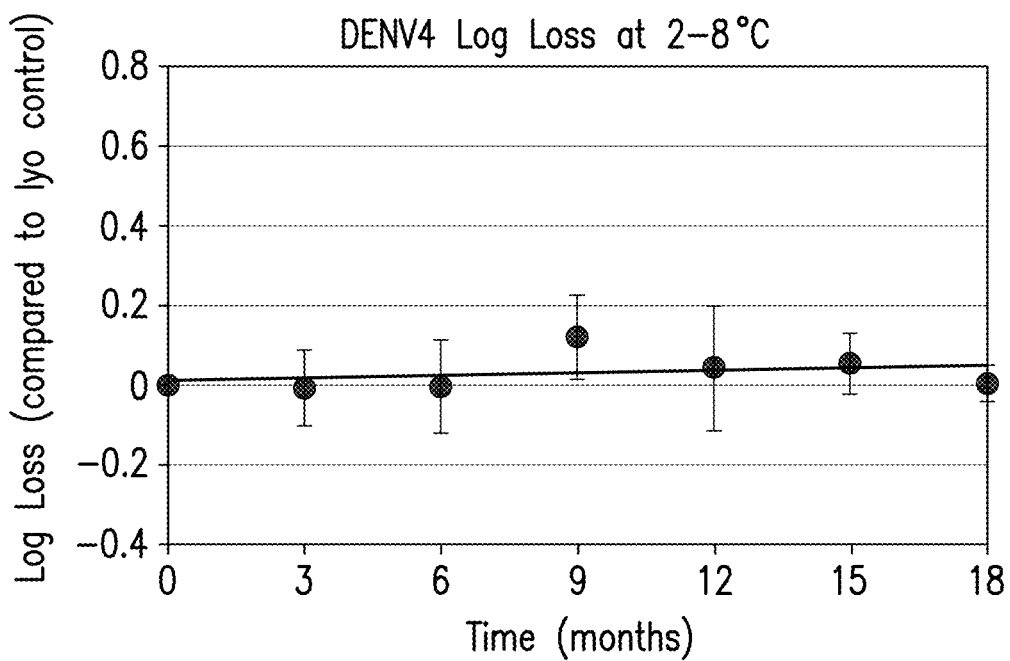

The log loss was calculated by converting the relative potency of the T0 timepoint of the dried material and the 1 week 25° C. stability material into logs by a Log 10 calculation. Once the numbers were converted into log, the stability timepoint was subtracted from the T0 timepoint to determine the log loss at 25° C. for 1 week.

The results showed that for DEN1 formulations containing ≥25% disaccharides, the lowest log loss at 25° C. one week was observed. The DEN4 formulations with ≥15% disaccharides and 30 mM salt had the lowest log loss at 25° C. at one week. For formulations containing ≥15% disaccharides and salt, the addition of sodium CMC helped with reducing residual moisture.

TABLE 11 summary of ranges of excipients of formulations in Table 10

| Excipients | Quantity (per 0.5 mL dose) |
|---|---|
| Sucrose | 0 mg-37.5 mg |
| Potassium Phosphate (monobasic, anhydrous) | ~0.26 mg |
| Potassium Phosphate (dibasic, anhydrous) | ~0.63 mg |
| L-glutamic acid (monosodium salt, monohydrate) | 0.56 mg |
| Trehalose | 37.5 mg-87.5 mg |
| Sodium Carboxylmethyl cellulose | 2.5 mg |
| Sodium Chloride | 0.88 mg |

Example 9

Formulations were 1×SPG (11 mM Potassium Phosphate, 6 mM L-glutamic acid, 0.22M Sucrose) with varying amounts of L-15 (90%, 45%, and 25%) and DEN1, DEN2, DEN3, or DEN4. The major component in Leibovitz's L-15 is NaCl (137.39 mM). Therefore, 90% L-15 equals 123.65 mM NaCl, 45% L-15 equals 61.83 mM NaCl, and 25% L-15 equals 34.35 mM NaCl.

The formulations were filled into 2R glass vials at a 0.5 mL fill and frozen at −115° C. for 15 minutes. Once frozen the vials were dried in the Microwave Vacuum Dryer (MVD). The vials were then submitted for potency testing using the Dengue Relative Infectivity Assay (DRIA).

Formulations that were dried fast under MVD were more stable than formulations dried slower under lyophilization (See FIGS. 13-16). In the above formulation, salt concentration of ≥61.83 mM NaCl appears to improve DEN4 stability during drying that is not observed in the other three types (DEN1, DEN2, and DEN3).

Example 10

The following solutions were also made: 500 mg/mL Sucrose, 250 mg/mL Trehalose, 1M Sodium Chloride (NaCl), and 10 mg/mL Sodium Carboxymethyl Cellulose (Sodium CMC), 100 mg/mL Polyvinylpyrrolidone (PVP), 100 mM Potassium Phosphate, 500 mg/mL Propylene Glycol, and Sterile Water.

All solutions were filtered with PES 0.22 μm Stericup filters. The solutions and Dengue virus (DEN1) were combined to obtain the following formulations: 11 mM Potassium Phosphate, 90 mg/mL Sucrose, 5 mg/mL sodium CMC, 5 mg/ml PG; 11 mM Potassium Phosphate, 200 mg/mL Sucrose, 50 mg/ml PVP K12; 11 mM Potassium Phosphate, 75 mg/mL Sucrose, 175 mg/ml Trehalose, 30 mM NaCl, 5 mg/ml CMC.

The formulations were filled into 2R glass vials at a 0.5 mL fill and frozen at −115° C. for 15 minutes. Once frozen the vials were dried in either a Microwave Vacuum Dryer (MVD) or Lyophilizer (Lyo). The vials were then submitted for potency testing using the Dengue Relative Infectivity Assay (DRIA).

FIG. 17 shows that relative potency of vials for the formulations dried in the Microwave Vacuum Dryer is greater than or equal to those dried in the Lyophilizer.

TABLE 12 summary of ranges of excipients of formulations in FIG. 17

| Excipients | Quantity (per 0.5 mL dose) |
|---|---|
| Sucrose | 37.5 mg-100 mg |
| Potassium Phosphate (monobasic, anhydrous) | ~0.26 mg |
| Potassium Phosphate (dibasic, anhydrous) | ~0.63 mg |
| Trehalose | 87.5 mg |
| Sodium carboxymethyl cellulose | 2.5 mg |

TABLE 12-continued summary of ranges of excipients of formulations in FIG. 17

| Excipients | Quantity (per 0.5 mL dose) |
|---|---|
| Sodium Chloride | 0.88 mg |
| PVP K12 | 25 mg |
| Propylene Glycol | 2.5 mg |

Example 11

Tetravalent formulations (formulation 20) of DENV1, DENV2, DENV3 and DENV4 were lyophilized and stored at 37° C. for one week (FIG. 18A), 25° C. for one month (FIG. 18B), and 2-8° C. for 18 months (FIGS. 19A-D). Potency was analyzed by plaque assay (as described earlier in the text) at each time point. A control sample stored at −70° C. was tested by plaque assay in the same assay run as each stability time point. A log loss for each time point was calculated by subtracting the log result of the stability sample from the −70° C. control sample. FIGS. 18A-B and 19A-D show the log loss over time for each of the serotypes in the tetravalent formulation 20. The error bars indicate two standard error of the mean of the log loss calculated at each time point. Formulation 20 provides thermal stability to all four dengue serotypes in the tetravalent vaccine at 37° C., 25° C. and 2-8° C. as evidenced by the minimal potency loss observed at 1 week, 1 month and 18 months, respectively.

Example 12

High Throughput Plaque Assay

The high throughput plaque assay "microplaque (uP)" assay is an automated, minitiarized dengue plaque assay run in a 96-well microplate. Briefly, Vero cells are seeded into black-walled, clear bottom tissue-culture plates in OptiPro SFM with 2% L-glutamine at 40,000 cells per well. Cells are allowed to attach overnight at 37° C., 5% pCO$_2$, >90% rH. Virus is pre-diluted in OptiMEM reduced serum media and further serially diluted 1:2 in media in ultra-low attachment plates. The plant medium is removed from the cell plates using gentle aspiration, and 25 µL/well of inoculum is transferred from the serial dilution plate to the cell plate. Viral adsorption proceeds for 4 hours at 37° C., 5% pCO$_2$, >90% rH. After the adsorption incubation, 175 µL/well overlay medium is added to all wells to inhibit viral secretion and spread. Depending on serotype, infection proceeds for 2 or 3 days at the aforementioned incubation conditions.

After the infection incubation, overlay medium is removed and cells are fixed with 3.7% formaldehyde in PBS. Plates are permeabilized with 0.5% Triton X-100 in PBS, then blocked with 1% BSA in PBS. Type specific rabbit monoclonal antibodies, followed by anti-rabbit AlexaFluor488 are used to fluorescently stain viral plaques. Plates are imaged using a Perkin Elmer EnSight and fluorescent plaques are counted by an automated counting algorithm. Titer is determined using equation below from wells that contain valid object counts that are within counting criteria (type dependent):

$$\text{Viral titer}\left(\frac{PFU}{mL}\right) = \frac{\text{plaques counted}}{\text{volume of inoculum (mL)}} \times \text{total dilution}$$

Two studies were executed in which tetravalent formulations of DENV1, DENV2, DENV3 and DENV4 were lyophilized in formulations detailed in Table 13 and stored at 25° C. for one week. Each formulation contains 9% sucrose, 11 mM potassium phosphate, 50 mM NaCl, 25 mM Leu at pH 7.5 and varying amounts of CMC or PG. Potency was analyzed by the high throughput plaque assay described above at each time point. A control sample stored at −70° C. was also tested in the assay. A log loss for each time point was calculated by subtracting the log result of the stability sample from the −70° C. control sample. Tables 14a and 14b show the log loss over time for each of the serotypes in the various tetravalent formulations. Concentrations of 0.2%-1% CMC or PG in various combinations show similar stability to each other and increased stability over formulations without the combination.

TABLE 13

Tetravalent Formulations

| Full Formulation | Formulation Variations | Formulation Number |
|---|---|---|
| 9% sucrose, 11 mM potassium phosphate, 50 mM NaCl, 25 mM Leu, pH 7.5 | No CMC or PG | 140 |
| 9% sucrose, 11 mM potassium phosphate, 0.5% CMC, 50 mM NaCl, 25 mM Leu, pH 7.5 | CMC only | 141 |
| 9% sucrose, 11 mM potassium phosphate, 0.2% CMC, 0.2% propylene glycol, 50 mM NaCl, 25 mM Leu, pH 7.5 | 0.2% CMC, 0.2% PG | 142 |
| 9% sucrose, 11 mM potassium phosphate, 0.3% CMC, 0.3% propylene glycol, 50 mM NaCl, 25 mM Leu, pH 7.5 | 0.3% CMC, 0.3% PG | 143 |
| 9% sucrose, 11 mM potassium phosphate, 0.5% CMC, 0.5% propylene glycol, 50 mM NaCl, 25 mM Leu, pH 7.5 | 0.5% CMC, 0.5% PG | 20 |
| 9% sucrose, 11 mM potassium phosphate, 0.8% CMC, 0.8% propylene glycol, 50 mM NaCl, 25 mM Leu, pH 7.5 | 0.8% CMC, 0.8% PG | 144 |
| 9% sucrose, 11 mM potassium phosphate, 0.9% CMC, 0.9% propylene glycol, 50 mM NaCl, 25 mM Leu, pH 7.5 | 0.9% CMC, 0.9% PG | 145 |
| 9% sucrose, 11 mM potassium phosphate, 0.8% CMC, 0.5% propylene glycol, 50 mM NaCl, 25 mM Leu, pH 7.5 | 0.8% CMC, 0.5% PG | 138 |
| 9% sucrose, 11 mM potassium phosphate, 0.5% CMC, 0.8% propylene glycol, 50 mM NaCl, 25 mM Leu, pH 7.5 | 0.5% CMC, 0.8% PG | 139 |
| 9% sucrose, 11 mM potassium phosphate, 0.3% CMC, 0.5% propylene glycol, 50 mM NaCl, 25 mM Leu, pH 7.5 | 0.3% CMC, 0.5% PG | 123 |

TABLE 14a

Effect of Concentration of CMC and PG on Stability at 25° C.

| Formulation | Formulation Number | DENV1 Log Loss 1 week 25° C. | DENV2 Log Loss 1 week 25° C. | DENV3 Log Loss 1 week 25° C. | DENV4 Log Loss 1 week 25° C. |
|---|---|---|---|---|---|
| No CMC or PG | 140 | 0.41 | 0.38 | 0.42 | 0.43 |
| CMC only | 141 | 0.47 | 0.40 | 0.52 | 0.31 |
| 0.2% CMC, 0.2% PG | 142 | 0.23 | 0.20 | 0.27 | 0.10 |

TABLE 14a-continued

Effect of Concentration of CMC and PG on Stability at 25° C.

| Formulation | Formulation Number | DENV1 Log Loss 1 week 25° C. | DENV2 Log Loss 1 week 25° C. | DENV3 Log Loss 1 week 25° C. | DENV4 Log Loss 1 week 25° C. |
|---|---|---|---|---|---|
| 0.3% CMC, 0.3% PG | 143 | 0.27 | 0.18 | 0.15 | 0.04 |
| 0.5% CMC, 0.5% PG | 20 | 0.18 | 0.16 | 0.23 | 0.04 |
| 0.8% CMC, 0.8% PG | 144 | 0.22 | 0.17 | 0.09 | 0.22 |
| 0.9% CMC, 0.9% PG | 145 | 0.16 | 0.12 | 0.03 | 0.16 |
| 0.8% CMC, 0.5% PG | 138 | 0.15 | 0.07 | 0.21 | −0.01 |
| 0.5% CMC, 0.8% PG | 139 | 0.20 | 0.12 | 0.18 | 0.04 |
| 0.3% CMC, 0.5% PG | 123 | 0.22 | 0.13 | 0.10 | 0.08 |

TABLE 14b

Effect of Concentration of CMC and PG on Stability at 25° C.

| Formulation | Formulation Number | DENV1 Log Loss 1 week 25° C. | DENV2 Log Loss 1 week 25° C. | DENV3 Log Loss 1 week 25° C. | DENV4 Log Loss 1 week 25° C. |
|---|---|---|---|---|---|
| 0.5% CMC, 0.5% PG | 20 | 0.19 | 0.30 | 0.15 | 0.06 |
| 0.2% CMC, 0.5% PG | 122 | 0.20 | 0.15 | 0.21 | 0.07 |
| 0.3% CMC, 0.5% PG | 123 | 0.26 | 0.12 | 0.16 | 0.02 |
| 0.4% CMC, 0.5% PG | 124 | 0.26 | 0.33 | 0.33 | 0.10 |
| 0.1% CMC, 0.5% PG | 125 | 0.27 | 0.33 | 0.22 | 0.16 |
| 0.5% CMC, 0.2% PG | 126 | 0.23 | 0.20 | 0.30 | 0.11 |
| 0.5% CMC, 0.3% PG | 127 | 0.31 | 0.28 | 0.22 | 0.14 |
| 0.5% CMC, 0.7% PG | 128 | 0.24 | 0.20 | 0.15 | 0.14 |
| 0.5% CMC, 0.1% PG | 129 | 0.23 | 0.15 | 0.16 | 0.19 |

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A formulation comprising:
   a) a live attenuated tetravalent dengue vaccine comprising i) 100-10,000,000 pfu/ml rDEN1Δ30 virus, ii) 100-10,000,000 pfu/ml rDEN2/4Δ30 virus, iii) 100-10,000,000 pfu/ml rDEN3Δ30/31 virus, and iv) 100-10,000,000 pfu/ml rDEN4Δ30 virus,
   b) 5-300 mM potassium phosphate buffer at pH 7.0 to 8.0,
   c) 60-120 mg/ml sucrose or trehalose or a combination thereof,
   d) 3-7 mg/ml propylene glycol or glycerol, and
   e) 3-7 mg/ml carboxymethylcellulose,
   f) optionally 30-90 mM NaCl, and
   g) optionally 10-75 mM amino acid Leu, Lys or Glu, or a combination thereof.

2. The formulation of claim 1 further comprising an aluminum adjuvant.

3. The formulation of claim 1 that is frozen or lyophilized.

4. The formulation of claim 1 that is reconstituted in solution.

5. The formulation of claim 1 that is in an aqueous solution prior to lyophilization or microwave vacuum drying.

* * * * *

UNITED STATES PATENT AND TRADEMARK OFFICE
CERTIFICATE OF CORRECTION

PATENT NO. : 12,208,135 B2
APPLICATION NO. : 18/530421
DATED : January 28, 2025
INVENTOR(S) : Michael S. Ryan et al.

Page 1 of 1

It is certified that error appears in the above-identified patent and that said Letters Patent is hereby corrected as shown below:

In the Claims

Claim 1, Column 61, Lines 4-5:
Please delete "rDEN1430 virus, ii) 100-10,000,000 pfu/ml rDEN2/4430"
And replace with "rDEN1Δ30 virus, ii) 100-10,000,000 pfu/ml rDEN2/4Δ30"

Signed and Sealed this
Twenty-fifth Day of March, 2025

Coke Morgan Stewart
*Acting Director of the United States Patent and Trademark Office*

```
                        SEQUENCE LISTING

Sequence total quantity: 9
SEQ ID NO: 1            moltype = AA  length = 395
FEATURE                 Location/Qualifiers
source                  1..395
                        mol_type = protein
                        organism = Dengue 1
SEQUENCE: 1
MRCVGIGSRD FVEGLSGATW VDVVLEHGSC VTTMAKDKPT LDIELLKTEV TNPAVLRKLC   60
IEAKISNTTT DSRCPTQGEA TLVEEQDANF VCRRTFVDRG WGNGCGLFGK GSLITCAKFK  120
CVTKLEGKIV QYENLKYSVI VTVHTGDQHQ VGNESTEHGT TATITPQAPT SEIQLTDYGA  180
LTLDCSPRTG LDFNEMVLLT MKEKSWLVHK QWFLDLPLPW TSGASTSQET WNRQDLLVTF  240
KTAHAKKQEV VVLGSQEGAM HTALTGATEI QTSGTTTIFA GHLKCRLKMD KLTLKGMSYV  300
MCTGSFKLEK EVAETQHGTV LVQIKYEGTD APCKIPFSTQ DERGVTQNGR LITANPIVTD  360
KEKPVNIEAE PPFGESYIVI GAGEKALKLS WFKKG                            395

SEQ ID NO: 2            moltype = AA  length = 395
FEATURE                 Location/Qualifiers
source                  1..395
                        mol_type = protein
                        organism = Dengue 2
SEQUENCE: 2
MRCIGISNRD FVEGVSGGSW VDIVLEHGSC VTTMAKNKPT LDFELIKTEA KQPATLRKYC   60
IEAKLTNTTT DSRCPTQGEP TLNEEQDKRF VCKHSMVDRG WGNGCGLFGK GGIVTCAMFT  120
CKKNMEGKIV QPENLEYTVV ITPHSGEEHA VGNDTGKHGK EVKITPQSSI TEAELTGYGT  180
VTMECSPRTG LDFNEMVLLQ MKDKAWLVHR QWFLDLPLPW LPGADTQGSN WIQKETLVTF  240
KNPHAKKQDV VVLGSQEGAM HTALTGATEI QMSSGNLLFT GHLKCRLRMD KLQLKGMSYS  300
MCTGKFKVVK EIAETQHGTI VIRVQYEGDG SPCKIPFEIM DLEKRHVLGR LITVNPIVTE  360
KDSPVNIEAE PPFGDSYIII GVEPGQLKLD WFKKG                            395

SEQ ID NO: 3            moltype = AA  length = 393
FEATURE                 Location/Qualifiers
```

```
source                          1..393
                                mol_type = protein
                                organism = Dengue 3
SEQUENCE: 3
MRCVGVGNRD FVEGLSGATW VDVVLEHGGC VTTMAKNKPT LDIELQKTEA TQLATLRKLC    60
IEGKITNITT DSRCPTQGEA ILPEEQDQNY VCKHTYVDRG WGNGCGLFGK GSLVTCAKFQ   120
CLESIEGKVV QHENLKYTVI ITVHTGDQHQ VGNETQGVTA EITPQASTVE AILPEYGTLG   180
LECSPRTGLD FNEMILLTMK NKAWMVHRQW FFDLPLPWTS GATTETPTWN RKELLVTFKN   240
AHAKKQEVVV LGSQEGAMHT ALTGATEIQN SGGTSIFAGH LKCRLKMDKL ELKGMSYAMC   300
LNTFVLKKEV SETQHGTILI KVEYKGEDAP CKIPFSTEDG QGKAHNGRLI TANPVVTKKE   360
EPVNIEAEPP FGESNIVIGI GDKALKINWY KKG                                393

SEQ ID NO: 4                    moltype = AA   length = 395
FEATURE                         Location/Qualifiers
source                          1..395
                                mol_type = protein
                                organism = Dengue 4
SEQUENCE: 4
MRCVGVGNRD FVEGVSGGAW VDLVLEHGGC VTTMAQGKPT LDFELIKTTA KEVALLRTYC    60
IEASISNITT ATRCPTQGEP YLKEEQDQQY ICRRDVVDRG WGNGCGLFGK GGVVTCAKFS   120
CSGKITGNLV QIENLEYTVV VTVHNGDTHA VGNDTSNHGV TATITPRSPS VEVKLPDYGE   180
LTLDCEPRSG IDFNEMILMK MKKKTWLVHK QWFLDLPLPW AAGADTSEVH WNYKERMVTF   240
KVPHAKRQDV TVLGSQEGAM HSALTGATEV DSGDGNHMYA GHLKCKVRME KLRIKGMSYT   300
MCSGKFSIDK EMAETQHGTT VVKVKYEGAG APCKVPIEIR DVNKEKVVGR IISSTPFAEY   360
TNSVTNIELE PPFGDSYIVI GVGDSALTLH WFRKG                              395

SEQ ID NO: 5                    moltype = AA   length = 451
FEATURE                         Location/Qualifiers
REGION                          1..451
                                note = DEN4-80EZip
source                          1..451
                                mol_type = protein
                                organism = synthetic construct
SEQUENCE: 5
MRCVGVGNRD FVEGVSGGAW VDLVLEHGGC VTTMAQGKPT LDFELIKTTA KEVALLRTYC    60
IEASISNITT ATRCPTQGEP YLKEEQDQQY ICRRDVVDRG WGNGCGLFGK GGVVTCAKFS   120
CSGKITGNLV QIENLEYTVV VTVHNGDTHA VGNDTSNHGV TATITPRSPS VEVKLPDYGE   180
LTLDCEPRSG IDFNEMILMK MKKKTWLVHK QWFLDLPLPW AAGADTSEVH WNYKERMVTF   240
KVPHAKRQDV TVLGSQEGAM HSALTGATEV DSGDGNHMYA GHLKCKVRME KLRIKGMSYT   300
MCSGKFSIDK EMAETQHGTT VVKVKYEGAG APCKVPIEIR DVNKEKVVGR IISSTPFAEY   360
TNSVTNIELE PPFGDSYIVI GVGDSALTLH WFRKGGGGSG GGGTGGGSGG GSPRMKQLED   420
KVEELLSKNY HLENEVARLK KLVGERGGCG G                                  451

SEQ ID NO: 6                    moltype = RNA   length = 10705
FEATURE                         Location/Qualifiers
misc_feature                    1..10705
                                note = DENV1
source                          1..10705
                                mol_type = other RNA
                                organism = synthetic construct
SEQUENCE: 6
agttgttagt ctacgtggac cgacaagaac agtttcgaat cggaagcttg cttaacgtag    60
ttctaacagt tttttattag agagcagatc tctgatgaac aaccaacgga aaaagacggg   120
tcgaccgtct ttcaatatgc tgaaacgcgc gagaaaccgc gtgtcaactg tttcacagtt   180
ggcgaagaga ttctcaaaag gattgctttc aggccaagga cccatgaaat tggtgatggc   240
ttttatagca ttcctaagat ttctagccat acctccaaca gcaggaattt tggctagatg   300
gggctcattc aagaagaatg gagcgatcaa agtgttacgg gtttcaagaa agaaatctc   360
aaacatgttg aacataatga acaggaggaa agatctgtg accatgctcc tcatgctgct   420
gcccacagcc ctggcgttcc atctgaccac ccgaggggga gagcgcacaa tgatagttag   480
caagcaggaa agaggaaaat cactttttgtt taagacctct gcaggtgtca acatgtgcac   540
ccttattgca atggatttgg agagttatg tgaggacaca atgacctaca aatgcccccg   600
gatcactgag acggaaccag atgacgttga ctgttggtgc aatgccacgg agacatgggt   660
gacctatgga acatgttctc aaactggtga acaccgacga gacaaacgtt ccgtcgcact   720
ggcaccacac gtagggcttg gtctagaaac aagaaccgaa acgtggatgt cctctgaagg   780
cgcttggaaa caaatacaaa aagtggagac ctgggctctg agacacccag gattcacggt   840
gatagccctt ttctagcac atgccatagg aacatccatc cccagaaagg gatcatttt   900
tatttgctg atgctggtaa ctccatccat ggccatgcgg tgcgtgggaa taggcaacag   960
agacttcgtg gaaggactgt caggagctac gtgggtggat gtggtactgg agcatggaag  1020
ttgcgtcact accatggcaa aagacaaacc aacactgatg attgaagacg gaaaagacgg  1080
ggtcacaaac cctgccgtcc tgcgcaaact gtgcattgaa gctaaatat caaacaccac  1140
caccgattcg agatgtccaa cacaggagag ccacgctgtg aagaacagga cacacgaa   1200
cttgtgtgt cgacgaacgt tcgtggacag aggctgggc aatggttgtg ggctattcgg  1260
aaaaggtagc ttaataacgt gtgctaagtt taagtgtgtg acaaaactgg aaggaaagat  1320
agtccaatat gaaaacttaa aatattcagt gatagtcacc gtacacgtgg agaccagatg  1380
ccaagttgga aatgagacca gaacatgtaa caactgcacc ataacactca agctcc    1440
cacgtcggaa atacagctga cagactacgg agctctaaca ttggattgtt cacctagaac  1500
agggctagac tttaatgaga tggtgttgtt gacaatggaa aaacgatcgt ggcctcgtcca  1560
caaacaatgg tttctagact taccactgcc ttggacctcg ggggcttcaa catcccaaga  1620
gacttggaat agacaagact tgctggtcac atttaagaca gctcatgcaa aaaagcagga  1680
```

```
agtagtcgta ctaggatcac aagaaggagc aatgcacact gcgttgactg gagcgacaga   1740
aatccaaacg tctggaacga caacaatttt tgcaggacac ctgaaatgca gactaaaaat   1800
ggataaactg actttaaaag ggatgtcata tgtaatgtgc acagggtcat tcaagttaga   1860
gaaggaagtg gctgagaccc agcatggaac tgttctagtg caggttaaat acgaaggaac   1920
agatgcacca tgcaagatcc ccttctcgtc ccaagatgaa aagggagtaa cccagaatgg   1980
gagattgata acagccaacc ccatagtcac tgacaaagaa aaaccagtca acattgaagc   2040
ggagccacct tttggtgaga gctacattgt ggtaggagca ggtgaaaaag ctttgaaact   2100
aagctggttc aagaagggaa gcagtatagg gaaaatgttt gaagcaactg cccgtggagc   2160
acgaaggatg gccatcctgg gagacactgc atgggacttc ggttctatag gagggggtgtt  2220
cacgtctgtg ggaaaactga tacaccagat ttttgggact gcgtatggag ttttgttcag   2280
cggtgtttct tggaccatga agataggaat agggattctg ctgacatggc taggattaaa   2340
ctcaaggagc acgtcccttt caatgacgtg tatcgcagtt ggcatggtca cactgtacct   2400
aggagtcatg gttcaggcgg actcgggatg tgtaatcaac tggaaaggca gagaactcaa   2460
atgtggaagc ggcattttttg tcaccaatga agtccacacc tggacagagc aatataaatt   2520
ccaggccgac tccctaaga gactatcagc ggccattggg aaggcatggg aggagggtgt    2580
gtgtggaatt cgatcagcca ctcgtctcga gaacatcatg tggaagcaaa tatcaaatga   2640
attaaaccac atccttacttg aaaatgacat gaaatttaca gtggtcgtag agacgttag    2700
tggaatcttg gcccaaggaa agaaaatgat taggccacca cccatggaac acaaatactc   2760
gtggaaaagc tggggaaaag ccaaaatcat aggagcagat gtacagaata ccaccttcat   2820
catcgacggc ccaaacaccc cagaatgccc tgataaccaa agagcatgga catttgggga   2880
agttgaagac tatggatttg gaattttcac gacaaacata tggttgaaat tgcgtgactc   2940
ctacactcaa gtgtgtgacc accggctaat gtcagctgcc atcaaggata gcaaagcagt   3000
ccatgctgac atgggtgtact ggatagaaag tgaaaagaac gagacttgga agttggcaag   3060
agcctccttc atagaagtta agacatgcat ctggccaaaa tcccacactc tatggagcaa   3120
tggagtcctg gaaagtgaga tgataatccc aaagatatat ggaggaccaa tatctcagca   3180
caactacaga ccaggatatt tcacacaaac agcagggccg tggcacttgg gcaagttaga   3240
actagatttt gatttatgtg aaggtaccac tgttgttgtg gatgaacatt gtggaaatcg   3300
aggaccatct cttagaacca caacagtcac aggaaagaca atccatgaat ggtgctgtag   3360
atcttgcacg ttacccccccc tacgtttcaa aggagaagac gggtgctggt acggcatgga   3420
aatcagacca gtcaaggaga aggaagagaa cctagttaag tcaatggtct ctgcagggtc   3480
aggagaagtg gacagttttt cactaggact gctatgcata tcaataatga tcgaagaggt   3540
aatgagatcc agatggagca gaaaaatgct gatgactgga acattggctg tgttcctcct   3600
tctcacaatg ggacaattga catggaatga tctgatcagg ctatgtatca tggttggagc   3660
caacgcttca gacaagatgg ggatgggaac aacgtaccta gctttgatgg ccactttcag   3720
aatgagacca atgttcgcag tcgggtact gtttcgcaga ttaacatcta gagaagttct   3780
tcttcttaca gttggattga gtctggtggc atctgtagaa ctaccaaatt ccttagagga   3840
gctaggggat ggacttgcaa tgggcatcat gatgttgaaa ttactgactg attttcagtc   3900
acatcagcta tgggctacct tgctgtcttt aacattgtc aaaacaactt tttcattgca    3960
ctatgcatgg aagacaatgg ctatgatact gtcaattgta tctctcttcc ctttatgcct   4020
gtccacgact tctcaaaaaa caacatggct tccggtgttg ctgggatctc ttggatgcaa   4080
accactaacc atgtttctta acagaaaaa caaaatctgg ggaaggaaaa gctggcctct   4140
caatgaagga attatggctg ttggaatagt tagcattctt ctaagttcac ttctcaagaa   4200
tgatgtgcca ctagctggcc cactaataagc tggaggcatg ctaatagcat gttatgtcat   4260
atctggaagc tcggccgatt tatcactgga gaaagcggct gaggtctcct gggaagaaga   4320
agcagacaca tctggtgcct cacacaacat actagtggag gtccaagatg atggaaccat   4380
gaaaataaag gatgaagaga gagatgacac actcaccatt ctcctcaaag caactctgct   4440
agcaatctca ggggtatacc caatgtcaat accggcgacc ctcttttgtgt ggtattttg   4500
gcagaaaaag aaacagagat caggagtgct atgggcacac cccagccctc cagaagtgga   4560
aagagcagtc cttgatgatg gcatttatag aattctccaa agaggattgt tgggcaggtc   4620
tcaagtagga gtaggagttt ttcaagaagg cgtgttccac acaatgtggc acgtcaccag   4680
gggagctgtc ctcatgtacc aagggaagag actggaacca agttgggcca gtgtcaaaaa   4740
agacttgatc tcatatgag gaggttggag gtttcaagga tcctggaacg cgggagaaga   4800
agtgcaggtg attgctgttg aaccggggaa gaacccaaa aatgtacaga cagcgccggg   4860
tacccttcaag acccctgaag gcgaagttgg agccatagct ctagactta aacccggcac   4920
atctgatct cctatcgtga acagagaggg aaaaatagta ggtctttatg gaaatggagt   4980
ggtgacaaca agtggtacct acgtcagtgc catagctcaa gctaaagcat cacaagaagg   5040
gcctctacca gagattgagg acgaggtgtt taggaaaaga aacttaacaa taatggacct   5100
acatccagga tcgggaaaaa caagaagata ccttccagcc atagtccgtg aggccataaa   5160
aagaaagctg cgcacgctag tcttagctcc cacaagagtt gtcgcttctg aaatggcaga   5220
ggcgctcaag ggaatgccaa taaggtatca gacaacagca gtgaagagtg aacacacggg   5280
aaaggagata gttgacctta tgtgtcacgc cactttcact atgcgtctcc tgtctcctgt   5340
gagagttccc aattataata tgattatcat ggatgaagca catttcaccg atccagccag   5400
catagcagcc agagggtata tctcaacccg agtgggtatg ggtgaagcag ctgcgatttt   5460
catgacagcc actcccccg gatcggtgga ggccttttca cagagcaatg cagttatcca   5520
agatgaggaa agagacattc ctgaaagatc atggaactca ggctatgact ggatcactga   5580
tttcccaggt aaaacagtct ggtttgttcc aagcatcaaa tcaggaaatg acattgccaa   5640
ctgtttaaga aagaatggga acgggtggt ccaattgagc agaaaaactt ttgacactga    5700
gtaccagaaa acaaaaata acgactggga ctatgttgtc acaacagaca tatccgaaat   5760
gggagcaaac ttccgagccg acaggggtaat agacccgagg cggtgcctga accggtaat   5820
actaaagat ggcccagagc gtgtcattct agccggaccg atgccagtga ctgtggctag   5880
cgccgcccag aggagaggaa gaattggaag gaaccaaaat aaggaaggcg atcagtatat   5940
ttacatggga cagcctctaa aaaatgatga ggaccacgcc cattgacag aagcaaaaat   6000
gctccttgac aacataaaca caccagaagg gattatccca gccctctttg agccggagag   6060
agaaaagagt gcagcaatag acgggggaata cagactacgg ggtgaagcga ggaaaacgtt   6120
cgtggagctc atgagaagag agatctacc tgtctggcta tcctacaaag ttgcctcaga   6180
aggcttccag tactccgaca aaggtggtgt ctttgatggg gaaaggaaca accaggtgtt   6240
ggaggagaac atgacgtgg agatctggac aaaagaagga gaaagaaga aactacgacc   6300
ccgctggctg gatgccagaa catactctga cccactggct ctgcgcgaat caaagagtt    6360
cgcagcagga agaagaagcg tctcaggtga cctaatatta gaaatagga aacttccaca   6420
```

```
acatttaacg caaagggccc agaacgcctt ggacaatctg gttatgttgc acaactctga  6480
acaaggagga aaagcctata gacacgccat ggaagaacta ccagacacca tagaaacgtt  6540
aatgctccta gctttgatag ctgtgctgac tggtggagtg acgttgttct tcctatcagg  6600
aaggggtcta ggaaaaacat ccattggcct actctgcgtg attgcctcaa gtgcactgtt  6660
atggatggcc agtgtggaac cccattggat agcggcctct atcatactgg agttctttct  6720
gatggtgttg cttattccag agccggacag acagcgcact ccacaagaca accagctagc  6780
atacgtggtg ataggtctgt tattcatgat attgacagtg gcagccaatg agatgggatt  6840
actggaaacc acaagaaagg acctgggggat tggtcatgca gctgctgaaa accaccatca  6900
tgctgcaatg ctggacgtag acctacatcc agcttcagcc tggactctct atgcagtggc  6960
cacaacaatt atcactccca tgatgagaca cacaattgaa aacacaacgg caaatatttc  7020
cctgacagct attgcaaacc aggcagctat attgatggga cttgacaagg gatgccaat   7080
atcaaagatg gacataggag ttccacttct cgccttgggg tgctattctc aggtgaaccc  7140
gctgacgctg acagcggcgg tatttatgct agtggctcat tatgccataa ttggacccgg  7200
actgcaagca aaagctacta gagaagctca aaaaaggaca gcagccggaa taatgaaaaa  7260
cccaactgtc gacgggatcg ttgcaataga tttggaccct gtggtttacg atgcaaaatt  7320
tgaaaaacag ctaggccaaa taatgttgtt gatactttgc acatcacaga tcctcctgat  7380
gcggaccaca tgggccttgt gtgaatccat cacactagcc actggacctc tgaccacgct  7440
ttgggaggga tctccaggaa aattctgaaa caccacgata gcggtgtcca tggcaaacat  7500
ttttagggga agttatctag caggagcagg tctggccttt tcattaatga aatctctagg  7560
aggaggtagg agaggcacgg gagcccaagg ggaaacactg ggagaaaaat ggaaaagaca  7620
gctaaaccaa ttgagcaagt cagaattcaa cacttacaaa aggagtggga ttatagaggt  7680
ggatagatct gaagccaaag aggggttaaa aagaggagaa acgactaaac acgcagtgtc  7740
gagaggaacg gccaaactga ggtggttgt ggagaggaac cttgtgaaac cagaagggaa  7800
agtcatagac ctcggttgtg aagaggtgg ctggtcatat tattgcgctg ggctgaagaa  7860
agtcacagaa gtgaaaggat acacgaaagg aggacctgga catgaggaac caatcccaat  7920
ggcaacctat ggatggaacc tagtaaagct atactccggg aaagatgtat tctttacacc  7980
acctgagaaa tgtgacaccc tcttgtgtga tattggtgag tcctctccga acccaactat  8040
agaagaagga agaacgttac gtgttctaaa gatggtggaa ccatggctca gaggaaacca  8100
atttttgcata aaaattctaa atcccatat gccgagtgtg gtagaaactt tggagcaaat  8160
gcaaagaaca catggaggaa tgctagtgcg aaatccactc tcaagaaact ccactcatga  8220
aatgtactgg gtttcatgtg aacaggaaca cattgtgtca gcagtaaaca tgacatctag  8280
aatgctgcta aatcgattca caatggctca caggaagcca acatatgaaa gagacgtgga  8340
cttaggcgct ggaacaagac atgtggcagt agaaccagag gtggccaacc tagatatcat  8400
tggccagagg atagaaata taaaaaatga acacaaatca acatggcatt atgatgagga  8460
caatccatac aaaaacatggg cctatcatgg atcatatgag gtcaagccat caggatcgac  8520
ctcatccatg gtcaatggtg tggtgagact gctaaccaaa ccatgggatg tcattcccat  8580
ggtcacacaa atagccatga ctgacaccac ccctttgga caacagaggg tgtttaaaga  8640
gaaagttgac acgcgtacac caaagcgaa acgaggcaca gcacaaatta tggaggtgac  8700
agccaggtgg ttatgggtt ttctctctag aaacaaaaaa cccagaatct gcacaagaga  8760
ggagttcaca agaaaagtca ggtcaaacgc agctattgga gcagtgttcg ttgatgaaaa  8820
tcaatggaac tcagcaaaag aggcagtgga agatgaacgg ttctgggacc ttgtgcacag  8880
agagagggag cttcataaac aaggaaaatg tgccacgtgt gtctacaaca tgatgggaaa  8940
gagagagaaa aaattaggag agttcggaaa ggcaaaagga agtcgcgcaa tatggtacat  9000
gtggttggga gcgcgctttt tagagtttga agcccttggt ttcatgaatg aagatcactg  9060
gttcagcaga gagaattcac tcagtggagt ggaaggagaa ggactccaca acttggata   9120
catactcaga gacatatcaa agattccagg gggaaatatg tatgcagatg acacagccgg  9180
atgggacaca agaataacag aggatgatct tcagaatgag gccaaaatca ctgacatcat  9240
ggaacctgaa catgccctat tggccacgtc aatctttaag ctaacctacc aaaacaaggt  9300
agtaaggtg cagagaccag cgaaaaatgg aaccgtgatg gatgtcatat ccagacgtga  9360
ccagagagga agtggacagg ttggaactta tggcttaaac accttcacca catggaggc   9420
ccaactaata agacaaatgg agtctgaggg aatcttttca cccagcgat tggaaacccc  9480
aaatctagcc gaaagagtcc tcgactggtt gaaaaacat ggcaccgaga ggctgaaaag  9540
aatggcaatc agtggagatg actgtgtggt gaaaccaatt gatgacagat ttgcaacagc  9600
cttaacagct ttgaatgaca tgggaaaggt aagaaaagac ataccgcaat gggaaccttc  9660
aaaaggatgg aatgattggc aacaagtgcc tttctgttca caccatttcc accagctgat  9720
tatgaaggat gggagggaga tagtggtgcc atgccgcaac caagatgaac ttgtaggtag  9780
ggccagagta tcacaaggcg ccggatggag cttgagagaa actgcatgcc taggcaagtc  9840
atatgcacaa atgtggcagc tgatgtactt ccacaggaga gacttgagat tagcggctaa  9900
tgctatctgt tcagccgttc cagttgattg gtgcccaacc agcgtacca ctggtcgtgat   9960
ccatgcccac catcaatgga tgacaacaga agacatgttg tcagtgtgga tagggtttg  10020
gatagaggaa aacccatgga tggaggacaa gactcatgtg tccagttggg aagacgttcc  10080
atacctagga aaaagggaag atcaatggtg tggatcccta ataggcttaa cagcacgagc  10140
cacctgggcc accaacatac aagtggccat aaaccaagtg agaaggctca ttgggaatga  10200
gaattatcta gacttcatga catcatgaa gagattcaaa aacgagagtg atcccgaagg  10260
ggcactctgg taagccaact cattcacaaa ataaggaaa ataaaaaatc aaacaaggca  10320
agaagtcagg ccggattaag ccatagcacg gtaagagcta tgctgcctgt gagccccgtc  10380
caaggacgta aaatgaagtc aggccgaaag ccacggttcg agcaagccgt gctgcctgta  10440
gctccatcgt ggggatgtaa aaacccggga ggctgcaaac catggaagct gtacgcatgg  10500
ggtagcagac tagtggttag aggagaccc tcccaagaca caacgcagca gcggggccca  10560
agactagagg ttagaggaga ccccccgcac aacaacaaac agcatattga cgctgggaga  10620
gaccagagat cctgctgtct ctacagcatc attccaggca cagatcggaa gaaaatggaa  10680
tggtgctgtt gaatcaacag gttct                                       10705

SEQ ID NO: 7        moltype = RNA   length = 10618
FEATURE             Location/Qualifiers
misc_feature        1..10618
                    note = DENV2
source              1..10618
                    mol_type = other RNA
```

-continued organism = synthetic construct
SEQUENCE: 7

```
agttgttagt ctgtgtggac cgacaaggac agttccaaat cggaagcttg cttaacacag   60
ttctaacagt ttgtttgaat agagagcaga tctctggaaa aatgaaccaa cgaaaaaagg  120
tggttagacc acctttcaat atgctgaaac gcgagagaaa ccgcgtatca accccctcaag  180
ggctggtgaa gagattctca accggacttt tttctgggaa aggacccctta cggatggtgc  240
tagcattcat cacgtttttg cgagtccttt ccatcccacc aacagcaggg attctgaaga  300
gatgggggaca gttgaagaaa aataaggcca tcaagatact gattggattc aggaaggaga  360
taggccgcat gctgaacatc ttgaacggga gaaaaaggtc tgcaggcatg atcattatgc  420
tgattccaac agtgatggcg ttccatttaa ccacacgtaa cggagaacca cacatgatcg  480
tcagtagaca agagaaaggg aaaagtcttc tgtttaaaac agaggatggt gtgaacatgt  540
gtaccctcat ggccatggac cttggtgaat tgtgtgaaga tacaatcacg tacaagtgtc  600
ctcttctcag gcagaatgaa ccagaagaca tagattgttg gtgcaactct acgtccacat  660
gggtaacttca tgggacgtgt accaccacag gagaaccaga aagagaaaaa agatcagtgg  720
cactcgttcc acatgtggga atgggactgg agacacgaac tgaaacatgg atgtcatcag  780
aaggggcctg gaaacatgcc cagagaattg aaacttggat cttgagacat ccaggcttta  840
ccataatggc agcaatcctg gcatacacca taggaacgac acatttccaa agagccctga  900
ttttcatctt actgacagct gtcgctcctt caatgacaac gcgttgcata ggaatatcaa  960
atagagactt tgtagaaggg gtttcaggag aagctgggtg tgacatagtc ttagaacatg 1020
gaagctgtgt gacgacgatg gcaaaaaaca aaccaacatt ggattttgaa ctgataaaaa 1080
cagaagccaa acaacctgcc actctaagga agtactgtat agaggcaaag ctgaccaaca 1140
caacaacaga atctcgctgc ccaacacaag gagaacctag cctaaatgaa gagcaggaca 1200
aaaggttcgt ctgcaaacac tccatgtggg acagaggatg gggaaatgga tgtggattat 1260
ttggaaaagg aggcattgtg acctgtgcta tgttcacatg caaaaagaac atggaaggaa 1320
aagtcgtgca accagaaaac ttgaatacac ccattgtgat aacacctcac tcaggggaag 1380
agcatgcagt cggaaatgac acaggaaaac atggcaagga aatcaaaata acaccacaga 1440
gttccatcac agaagcagag ttgacaggct atggcactgt cacgatggaa tgctttccga 1500
gaacgggcct cgacttcaat gagatggtgt tgctgcaaat ggaaaataaa gcttggctgg 1560
tgcacaggca atggttccta gacctgccgt tgccatggct gcccggagcg gacacacaag 1620
gatcaaattg gatacagaaa gagacattgg tcactttcaa aaatcccat gcgaagaaac 1680
aggatgttgt tgttttggga tcccaagaag gggccatgca cacagcactc acaggggcca 1740
cagaaatcca gatgtcatca ggaaacttac tgttcacagg acatctcaag tgcaggctga 1800
ggatggacaa actacagctc aaaggaatgt catactctat gtgcacagga aagtttaaag 1860
ttgtgaagga aatagcagaa acacaacatg gaacaatagt tatcagagta caatatgaag 1920
gggacggttc tccatgtaag atccctttg agataatgga tttggaaaaa agacatgttt 1980
taggtcgcct gattacagtc aacccaatcg taacagaaaa agatagccca gtcaacatag 2040
aagcagaacc tccattcgga gacagctaca tcatcatagg agtagagccg gacaattga 2100
agctcaactg gtttaagaaa ggaagttcta tcggccaaat gtttgagaca acaatgaggg 2160
gagcgaagga aatggccatt ttaggtgaca cagcttgagg ttttggatcc ctgggaggag 2220
tgtttacatc tataggaaag gctctccacc aagttttcgg agcaatctat ggggctgcct 2280
tcagtggggt ctcatggact atgaaaatcc tcataggagt cattatcaca tggataggaa 2340
tgaactcgag gaacacttca atggctatga cgtgcatagc tgttggagga atcactctgt 2400
ttctgggctt cacagttcaa gcagacatgg gttgtgtggt gtcatggagt gggaaagaat 2460
tgaagtgtgg aagcggaatt tttgtggttg acaacgtgca cacttggaca gaacagtaca 2520
aatttcaacc agagtcccca gcgagactag cgtctgcaat attaaatgcc acaaagatg 2580
gggtctgtgg aattagatca accacgaggc tggaaaatgt catgtggaag caaataacca 2640
acgagctaaa ctatgttctc tgggaaggag gacatgacct cactgtagtg gctggggatg 2700
tgaaggggt gttgaccaaa ggcaagagag cactcacacc cccagtgagt gatctgaaat 2760
attcatggaa gacatgggga aaagcaaaaa tcttcacccc agaagcaaga aatagcacat 2820
tttaatagac cggaccagac acctctgaat gccccaatga acgaagagca tggaactctc 2880
ttgaggtgga agactatgga tttggcatgt tcacgaccaa catatggatg aaattccgtg 2940
aaggaagttc agaagtgtgt gaccacaggt taatgtcagc tgcaattaaa gatcagaaag 3000
ctgtgcatgc tgacatgggt tattggatag agagctcaaa aaaccagacc tggcagatag 3060
agaaagcatc tcttattgaa gtgaaaacat gtctgtggcc caagacccac acactgtgga 3120
gcaatggagt gctggaaagc cagatgctca ttccaaaatc atatgcgggc ccttttttcac 3180
agcacaatta ccgccagggc tatgccacgc aaaccgtggg cccatggcac ttaggcaaat 3240
tagagataga ctttgagaa tgccccggaa caacagtcac aattcaggag gattgtgacc 3300
atagaggccc atctttgagg accaccactg catctgaaaa actagtcacg caatggtgct 3360
gccgctcctg cacgatgcct cccttaaggt tcttgggaga agatgggtgc tggtatggac 3420
tggagattag gccccttgagt gaaaaagaag agaacatggt caaatcacag gtgacggccg 3480
gacagggcac atcagaaact ttttctatgg gtctgttgtg cctgaccttg tttgtggaag 3540
aatgcttgag gagaagagtc actaggaaac acatgatatt agttgtggtg atcactcttt 3600
gtgctatcat cctgggaggc ctcacatgga tggacttact acgagccctc atcatgttgg 3660
gggacactat gtctggtaga ataggaggac agatccatct agcctcatgt gggacactat 3720
agatgtcacc aggatacgtg ctgggtgtgt ttttaaggaa actcacttca agagagcag 3780
cactaatggt aataggaatg gccatgacaa cggtgctttc aattccacat gaccttatgg 3840
aactcattga tggaatatca ctgggactaa ttttgctaaa aatagtaaca cagtttgaca 3900
acacccaagt gggaaccctta gctctcttcct tgacttcat aagatcaaca atgccattgg 3960
tcatgccttg gaggaccatt atggctgtgt tgtttggt cacactcatt cctttgtgca 4020
ggacaagctg tcttcaaaaa cagtctcatt gggtagaaat aacagcactc atcctaggaa 4080
cccaagctct gccagtgtac ctaatgactc ttatgaaagg agcctcaaga agatcttggc 4140
ctcttaacga gggcataatg gctgtgggtt tggttagtct cttaggaagc gctccttttaa 4200
agaatgatgt ccctttagct ggcccaatgg tggcaggagg cttacttctg gcggcttacg 4260
tgatgagtgg tagctcagca gatctgtcac tagagaaggc cgcaacgtg cagtgggatg 4320
aaatggcaga cataacaggc tcaagcccaa tcatagaagt gaagcaggat gaagatggct 4380
cttttctccat acgggacgtc gaggaaacca atatgataac cttttttggtg aaactggcac 4440
tgataacagt gtcaggtctc taccccttgg caattccagt cacaatgacc ttatggtaca 4500
tgtggcaagt gaaaacacaa agatcaggag ccctgtggga cgtcccctca cccgctgcca 4560
ctaaaaaagc cgcactgtct gaaggagtgt acaggatcat gcaagagggg ttattcggga 4620
```

```
aaactcaggt tggagtaggg atacacatgg aaggtgtatt tcacacaatg tggcatgtaa   4680
caagaggatc agtgatctgc cacgagactg ggagattgga gccatcttgg gctgacgtca   4740
ggaatgacat gatatcatac ggtgggggat ggaggcttgg agacaaatgg gacaaagaag   4800
aagacgttca ggtcctcgcc atagaaccag gaaaaaatcc taaacatgtc caaacgaaac   4860
ctggccttt caagacccta actggagaaa ttggagcagt aacattagat ttcaaacccg   4920
gaacgtctgg ttctcccatc atcaacagga aaggaaaagt catccggactc tatggaaatg   4980
gagtagttac caaatcaggt gattacgtca gtgccataac gcaagccgaa agaattggag   5040
agccagatta tgaagtggat gaggacattt ttcgaaagaa aagattaact ataatggact   5100
tacaccccgg agctggaaag acaaaaagaa ttcttccatc aatagtgaga gaagccttaa   5160
aaaggaggct acgaactttg attttagctc ccacgagagt ggtggcggcc gagatggaag   5220
aggccctacg tggactgcca atccgttatc agacccagc tgtgaaatca gaacacacag   5280
gaagagagat tgtagacctc atgtgtcatg caaccttcac aacaagactt ttgtcatcaa   5340
ccagggttcc aaattacaac cttatagtga tggatgaagc acatttcacc gatccttcta   5400
gtgtcgcggc tagaggatac atctcgacca gggtgtgaac gggagaggca gcagccatct   5460
tcatgaccgc aaccccctcc ggagcgacag atcccttttcc ccagagcaac agcccaatag   5520
aagacatcga gagggaaatt ccggaaaggt catggaacac agggtcgac tggataacag   5580
actaccaagg gaaaactgtg tggtttgttc ccagcataaa agctggaaat gacattgcaa   5640
attgttttgag aaagtcggga aagaaagtta tccagttgag taggaaaacc tttgatacag   5700
agtatccaaa aacgaaactc acggactggg actttgtggt cactacagac atatctgaaa   5760
tgggggccaa ttttagagcc gggagagtga tagaccctag aagatgcctc aagccagtta   5820
tcctaccaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac acccccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtgct ataag gtagcttctg   6180
ctggcatttc ttacaaagat cgggaatggt gcttcacagg ggaaagaaat aaccaaattt   6240
tagaagaaaa catggaggtt gaaatttgga ctagagaggg agaaaagaaa aagctaaggc   6300
caagatggtt agatgcacgt gtatacgctg acccatgc tttgaaggat ttcaaggagt   6360
ttgccagtgg aaggaagagt ataactctcg acatcctaac agagattgcc agtttgccaa   6420
cttaccttc ctctagggcc aagctcgccc ttgataacat agtcatgctc cacacaacag   6480
aaagaggagg gagggcctat caacacgccc tgaacgaact tccggagtca ctggaaacac   6540
tcatgcttgt agctttacta ggtgctatga cagcaggcat cttcctgttt ttcatgcaag   6600
ggaaaggaat agggaaattg tcaatgggtt tgataaccat tgcggtggct agtggcttga   6660
tctgggtagc agaaattcaa ccccagtgga tagcggcctc aatcatacta gagttttttc   6720
tcatggtact gttgataccg gaaccagaaa aacaaaggac cccacaagac aatcaattga   6780
tctacgtcat attgaccatt ctcaccatca ttggtctaat agcagccaac gagatggggc   6840
tgattgaaaa aacaaaaacg gattttgggt tttaccaggt aaaaacagaa accaccatcc   6900
tcgatgtgga cttgagacca gcttcagcat ggacgctcta tgcagtagcc accacaattc   6960
tgactcccat gctgagacac accatagaaa acacgtcggc caacctatct ctagcagcca   7020
ttgccaacca ggcagccgtc ctaatggggc ttggaaaagg atggccgctc cacagaatgg   7080
acctcggtgt gccgctgtta gcaatgggat gctattctca agtgaaccca ataacctga   7140
cagcatcctt agtcatgctt ttcgtgcact atgcaataat aggcccagga ttgcaggcaa   7200
aagccacaag agaggcccag aaaaggacag ctgctgggat catgaaaaat cccacagtgg   7260
acgggataac agtaatagat ctagaaccaa tatcctatga cccaaaattt gaaaagcaat   7320
tagggcaggt catgctacta gtcttgtgtg ctggacaact actcttgatg agaacaacat   7380
gggcttttct tgaagtcttg actttggcca caggaccact cctgacctttg tgggagggca   7440
acccgggaag gttttggaac acgaccatag ccgtatccac cgccaacatt tcaggggaca   7500
gttacttggc gggagctgga ctggcttttt cactcataaa gaatgcacaa accccctagga   7560
ggggaactgg gaccacagga gagacactgg gagagaagtg gaagagacag ctaaactcat   7620
tagacagaaa agagtttaaa gagtataaaa gaagtggaaat actagaagtg gacaggactg   7680
aagccaagtc tgccctgaaa gatgggtcta aaatcaagca tgcagtatca agagggtcca   7740
gtaagatcag atggattgtt gagagaggga tggtaaagcc aaaagggaaa gttgtagatc   7800
ttggctgtgg gagaggagga tggtcttatt acatggcgac actcaagaac gtgactgaag   7860
tgaaagggta tacaaaagga ggtccaggac atgaagaacc gattcccatg gctacttatg   7920
gttggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctgagaaa ctgcagagaa   8160
aacatggtgg gaaccttgtc agatgcccgc tgtccaggaa ctccacccat gagatgtatt   8220
gggtgtcagg agcgtcggga acattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgcaaatc attgggagaa   8400
ggcttcagcg attgcaagaa gagcacaaag aaaacccat ttatgatcag gaaaacccat   8460
acagaacctg ggcgtatcat ggaagctatg aagctccttc gacaggctct gcatcctcca   8520
tggtgaacgg ggtggtaaaa ctgctaacaa accctgggaa tgtgattcca atggtgactc   8580
agttagccat gacagataca acccccttttg ggaacaaaag agtgttcaaa gagaaggtgg   8640
ataccagaac accacaacca aaacccggta cacgaatggt tatgaccacg acagccaatt   8700
ggctgtgggc cctccttgga aagaagaaaa atcccagact gtgcacaagg gaagagttca   8760
tctcaaaagt tagatcaaac gcagccatag cgcagtcttt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctataa catgatggga aaacgtgaga   8940
aaaagttagg agagtttggc agagccaagg gaagccgagc aatctggtac atgtggctgg   9000
gagcgcggtt tctggaattt gaagccctgg gtttttttga taagatcctg gttttggcaa   9060
gagaaaattc atggagtgga gtggaagggg aaggtctgca cagattggga tatatcctga   9120
aggagataga caagaaggat ggagacctaa tgtatgctga tgcacagca ggctgggaca   9180
caagaatcac tgaggatgac cttcaaaatg aggaactgat cacggaacag atggctcccc   9240
accacaagat cctagccaaa gccatttttca aactaaccta tcaaaacaaa gtggtgaaag   9300
tcctcagacc cacaccgcgg ggagcggtga tggatatcat atccagagaa gaccaaagag   9360
```

-continued

```
gtagtggaca agttggaaca tatggtttga acacattcac caacatggaa gttcaactca  9420
tccgccaaat ggaagctgaa ggagtcatca cacaagatga catgcagaac ccaaaagggt  9480
tgaaagaaag agttgagaaa tggctgaaag agtgtggtgt cgacaggtta aagaggatgg  9540
caatcagtgg agacgattgc gtggtgaagc ccctagatga gaggtttggc acttccctcc  9600
tcttcttgaa cgacatggga aaggtgagga aagacattcc gcagtgggaa ccatctaagg  9660
gatggaaaaa ctggcaagag gttccttttt gctcccacca ctttcacaag atctttatga  9720
aggatggccg ctcactagtt gttccatgta gaaaccagga tgaactgata gggagagcca  9780
gaatctcgca gggagctgga tggagcttaa gagaaacagc ctgcctgggc aaagcttacg  9840
cccagatgtg gtcgcttatg tacttccaca gaagggatct gcgtttagcc tccatggcca  9900
tatgctcagc agttccaacg gaatggtttc caacaagcag aacaacatgg tcaatccacg  9960
ctcatcacca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcacacg gccataaccc aggtcaggaa cctgatcgga aaagaggaat  10200
acgtggatta catgccagta atgaaaagat acagtgctcc ttcagagagt gaaggagttc  10260
tgtaattacc aacaacaaac accaaaggct attgaagtca ggccacttgt gccacggttt  10320
gagcaaaccg tgctgcctgt agctccgcca ataatgggag gcgtaataat ccccagggag  10380
gccatgcgcc acggaagctg tacgcgtggc atattggact agcggttaga ggagacccct  10440
cccatcactg acaaaacgca gcaaaagggg gcccaagact agaggttaga ggagaccccc  10500
ccaacacaaa aacagcatat tgacgctggg aaagaccaga gatcctgctg tctctgcaac  10560
atcaatccag gcacagagcg ccgcaagatg gattggtgtt gttgatccaa caggttct    10618

SEQ ID NO: 8           moltype = RNA  length = 10645
FEATURE                Location/Qualifiers
misc_feature           1..10645
                       note = DENV3
source                 1..10645
                       mol_type = other RNA
                       organism = synthetic construct
SEQUENCE: 8
agttgttagt ctacgtggac cgacaagaac agtttcgact cggaagcttg cttaacgtag  60
tactgacagt tttttattag agagcagatc tctgatgaac aaccaacgga aaaagacggg  120
aaaaccgtct atcaatatgc tgaaacgcgt gagaaaccgt gtgtcaactg gatcacagtt  180
ggcgaagaga ttctcaagag gactgctgaa cggccaagga ccaatgaaat tggttatggc  240
gttcatagct ttcctcagat ttctagccat tccaccgaca gcaggagtct tggctagatg  300
gggaaccttt aagaagtcgg gggctattaa ggtcctgaga ggcttcaaga aggagatctc  360
aaacatgctg agcattatca acagacggaa aaagacatcg ctctgtctca tgatgatgtt  420
accagcaaca cttgctttcc acttgacttc acgagatgga gagccgcgca tgattgtggg  480
gaagaatgaa agaggaaaat ccctactttt taagacagcc tctggaatca acatgtgcac  540
actcatagcc atggatttgg gagagatgtg tgatgacacg gtcacctaca aatgcccct  600
cattactgaa gtggagcctg aagacattga ctgctggtgc aaccttacat cgacatgggt  660
gacctacgga acgtgcaatc aagctggaga gcacagacgc gacaaaagat cggtggcgtt  720
agctccccat gtcggcatgg gactggacac acgcacccaa acctggatgt cggctgaagg  780
agcttggaga caggtcgaga aggtagagac atgggccttt aggcacccag ggttcacaat  840
actagcccta tttcttgccc attacatagg cacttccttg acccagaaag tggttatttt  900
catactacta atgctggtca ccccatccat gacaatgaga tgcgtgggag taggaaacag  960
agatttgtg gaaggcctat caggagctac gtgggttgac gtggtgctcg agcacggtgg  1020
gtgtgtgact accatggcta agaacaagcc cacgctggat atagagctcc agaagaccga  1080
ggccacccaa ctggcgaccc taaggaaact atgtattgag ggaaaaatta ccaacgtaac  1140
aaccgactca aggtgcccca cccaagggga agcgatttta cctgaggagc aggaccagaa  1200
ccacgtgtgc aagcacacat acgtggacag aggctgggga aacggttgtg gtttgtttgg  1260
caagggaagc ctggtaacat gcgcgaaatt tcaatgtttg gaatcaatag agggaaaagt  1320
ggtgcagcat gagaacctca aatacaccgt catcatcaca gtgcacacag gagatcaaca  1380
ccaggtggga aatgaaacgc agggagtcac ggctgagata acaccccagg catcaaccgt  1440
tgaagccatc ttacctgaat atggaaccct tgggctagaa tgctcaccac ggacaggttt  1500
agatttcaat gaaatgattt tgttgacaat gaagaacaga gcatggatgg tacatagaca  1560
atggtttttt gacctacctt taccatggac atcaggagct acaacagaaa caccaacctg  1620
gaataagaaa gagcttcttg tgacattcaa aaacgcacat gcaaaaaagc aagaagtagt  1680
ggtccttgga tcgcaagagg gagcaatgca cacagcactg acaggagcta cagagatcca  1740
aacctcagga ggcacaagta tttttgcggg gcacttaaaa tgtagactca agatggacaa  1800
attggaactc aaggggatga gctatgcaat gtgcttgaat gcctttgtgt tgaagaaaga  1860
agtctccgaa acgcaacatg ggacaatact catcaaggtt gagtacaaag ggaaagatgc  1920
accttgcaag attcctttct ccacggagga tggacaaggg aaagcccaca atggcagact  1980
gatcacagct aacccagtgg tgaccaagaa ggaggagcct gtcaatattg aggcagaacc  2040
tccttttggg gaaagcaata tagtaattgg aattggagac aaagccttga aaattaactg  2100
gtacaagaag ggaagctcga ttgggaagat gttcgaggcc actgccagag gtgcaaggcg  2160
catggccatc ttgggagaca cagcctggga ctttggatca gtaggtggtg ttttaaattc  2220
attaggaaaa atggtgcacc aaatatttgg aagtgcttac acagccctat ttagtggagt  2280
ctcctggata atgaaaattg gaataggtgt ccttttaacc tggataggt tgaattcaaa  2340
aaacactagt atgagcttta gctgcattgt gataggaatc attacactct atctgggagc  2400
cgtggtgcaa gctgacatgg ggtgtgtcat aaactggaaa ggcaaagaac tcaaatgtgg  2460
aagtggaatt ttcgtcacta atgaggtcca cacctggaca gagcaataca aatttcaagc  2520
agactccccc aaaagactgg cgacagccat tgcaggcgct tgggagaatg gagtgtgcgg  2580
aatcaggtcg acaaccagaa tggagaacct cttgtggaag caaatagcca atgaactgaa  2640
ctacatatta tgggaaaaca acatcaaatt aacggtagtt gtgggtgata taattggggt  2700
cttagagcaa gggaaaagaa cactaacacc acaacccatg gaactaaaat attcatggaa  2760
aacatgggga aaggcgaaga tagtgacagc tgaaacacaa aattcctctt tcataataga  2820
tgggccaaac acaccagagt gtccaagtgc ctcaagagca tggaatgtgt gggaggtgga  2880
agattacggg ttcggagtct tcacaactaa catatggctg aaactccgag agatgtacac  2940
```

```
ccaactatgt gaccacaggc taatgtcggc agccgttaag gatgagaggg ccgtacacgc 3000
cgacatgggc tattggatag aaagccaaaa gaatggaagt tggaagctag aaaaggcatc 3060
cctcatagag gtaaaaacct gcacatggcc aaaatcacac actctttgga gcaatggtgt 3120
gctagagagt gacatgatca tcccaaagag tctggctggt cccatttcgc aacacaacta 3180
caggcccgga taccacaccc aaacggcagg accctgacca ttaggaaaat tggagctgga 3240
cttcaactat tgtgaaggaa caacagttgt catcacagaa aattgtggga caagaggccc 3300
atcactgaga caacaacag tgtcaggaa gttgatacac gaatggtgtt gccgctcgtg 3360
tacacttcct cccctgcgat acatgggaga agacggctgc tggtatggca tggaaattag 3420
acccattaat gagaaagaag agaacatggt aaagtcttta gtctcagcag ggagtggaaa 3480
ggtggataac ttcacaatgg gtgtcttgtg tttggcaatc ctttttgaag aggtgatgag 3540
aggaaaattt gggaaaaagc acatgattgc aggggttctc ttcacgtttg tactccttct 3600
ctcagggcaa ataacatgga gagacatggc gcacacactc ataatgattg ggtccaacgc 3660
ctctgacaga atgggaatgg gcgtcactta cctagcattg attgcaacat ttaaaattca 3720
gccatttttg gctttgggat tcttcctgag gaaactgaca tctagagaaa atttattgtt 3780
gggagttggg ttggccatgg caacaacgtt acaactgcca gaggacattg aacaaatggc 3840
gaatggaata gctttaggc tcatggctct taattaata acacaatttg aaacatacca 3900
actatgacg gcattagtct ccctaatgtg ttcaaataca atttcacgt tgactgttgc 3960
ctggagaaca gccaccctga ttttggccgg aatttctctt ttgccagtgt gccagtcttc 4020
gagcatgagg aaaacagatt ggctcccaat ggctgtggca gctatgggag ttccacccct 4080
accacttttt atttcagtt tgaaagatac gctcaaaagg agaagctggc cactgaatga 4140
gggggtgatg gctgttggac ttgtgagtat tctagctagt tctctcctta ggaatgacgt 4200
gccatggct ggaccattag tggctggggg cttgctgata gcgtgctacg tcataactgg 4260
cacgtcagca gacctcactg tagaaaaagc agcagatgtg acatgggagg aagaggctga 4320
gcaaacagga gtgtcccaca atttaatgat cacagttgat gacgatggaa caatgagaat 4380
aaaagatgat gagactgaga acatcttaac agtgcttttg aaaacagcat tactaatagt 4440
gtcaggcatt tttccatact ccatacccgc aacactgttg gtctggcaca cttggcaaaa 4500
gcaaacccaa agatccggtg tcctatggga cgttcccagc cccccagaga cacagaaagc 4560
agaactggaa aagggtttt ataggatcaa gcagcaagga atttttggga aaacccaagt 4620
ggggggttgga gtacaaaaag aaggagtttt ccacaccatg tggcacgtca aagaggagc 4680
agtgttgaca cacaatggga aaagctggga accaaactgg gctagcgtga aaaagatct 4740
gatttcatac ggaggaggat ggaaattgag tgcacaatgg caaaaggag aggaggtgca 4800
ggttattgcc gtagagcctg gaagaaccc aaagaacttt caaaccatgc caggcatttt 4860
ccagacaaca acaggggaga taggagcgat tgcactggac ttcaagcctg gaacttcagg 4920
atctccatc ataaacagag agggaaaggt actgggattg tatggcaatg gagtggtcac 4980
aaagaatggt ggctatgtca gtggaatagc acaaacaaat gcagaaccag acgaccgac 5040
accagagttg gaagaagaga tgttcaaaaa gcgaaatcta accataatgg atctccatcc 5100
cgggtcagga aagacgcgga aatatcttcc agctattgtt agagaggcaa tcaagagacg 5160
cttaaggact ctaatttttgg caccaacaag ggtagttgca gctgagatgg aagaagcatt 5220
gaaagggctc ccaataaggt atcaaacaac tgcaacaaaa tctgaacaca cagggagaga 5280
gattgttgat ctaatgtgcc acgcaacgtt cacaatgcgt ttgctgtcac cagtcagggt 5340
tccaaactac aacttgataa taatggatga ggctcatttc acagacccag ccagtatagc 5400
ggctagaggg tacatatcaa ctcgtgtagg aatgggagag cagccgcaa ttttcatgac 5460
agccacaccc cctggaacac ctgatgcctt tcctcagagc aacgctccaa ttcaagatga 5520
agaaagagac ataccagaac gctcatgaa ttcaggcaat gaatggatta ccgactttgc 5580
cgggaagacg gtgtggtttg tccctagcat caaagctgga aatgacatag caaactgctt 5640
gcggaaaaat ggaaaaaagg tcattcaact tagtaggaag acttttgaca cagaaatcca 5700
aaagactaaa ctaaatgatt gggacttgt ggtgacaaca gacatttcag aaatgggagc 5760
caatttcaaa gcagcagag tgatcgaccc aagaagatgt ctcaagccag tgattttgac 5820
agacggaccc gagcgcgtga tcctggcggg accaatgcca gtcaccgtag cgagcgctgc 5880
gcaaggagag ggagagttgg caggaaccc acaaaaagaa aatgaccaat acatattcat 5940
gggccagccc ctcaataatg atgaagacca tgctcactgg acagaagcaa aaatgctgct 6000
agacaacatc aacacaccag aagggatcat accagctctc tttgaaccag aaagggagaa 6060
gtcagccgcc atagacggcg aataccgcct gaagggtgag tccaggaaga ccttcgtgga 6120
actcatgagg agggtgacc tcccagtttg gctagcccat aaagtagcat cagaagggat 6180
caaatataca gatagaaagt ggtgttttga tggagaacgc aacaatcaaa ttttagagga 6240
gaatatggat gtggaaatct ggacaaagga aggagaaaag aaaaaattga gacctaggtg 6300
gcttgatgcc cgcacttatt cagatcccct agcgctcaag gaattcaagg actttgcggc 6360
tggtagaaag tcaattgccc ttgatcttgt gacagaaata ggaagagtgc cttcacactt 6420
agctcacaga acgagaaacg ccctggacaa tctgtgatgc ttgcacacgt cagaacatgg 6480
cgggagggcc tacaggcatg cagtggagga actaccagaa acaatggaaa cactcttact 6540
cctgggactc atgatcctgt taacaggtgg agcaatgctt ttcttgatat caggtaaagg 6600
gattggaaag acttcaatag gactcatttg tgtagctgct tccagcggta tgttatggat 6660
ggctgatgtc ccactccaat ggatcgcgtc tgccatagtc ctggagtttt ttatgatggt 6720
gttacttata ccagaaccag aaaagcagag aactccccaa gacaatcaac tcgcatatgt 6780
cgtgataggc atactcacac tggctgcaat agtagcagcc aatgaaatgg gactgttgga 6840
aaccacaaag agagatttag aatgtccaa agaaccaggt gttgtttctc caaccagcta 6900
tttggatgtg gacttgcacc cagcatcagc ctggacattg tacgctgtgg ccacaacagt 6960
aataacaccca atgttgagac ataccataga gaattccaca gcaaatgtgt ccctggcagc 7020
tatagccaac caggcagtgg tcctgatggg tttagacaaa ggatggccga tatcgaaaat 7080
ggacttaggc gtgccactat ggcactgggt tgttattca caagtgaacc cactaactct 7140
cacagcggca gttctcctgc tagccacgca ttatgctatt ataggtccag gattgcaggc 7200
aaaagccact cgtgaagctc aaaaaggac agctgctgga ataatgaaga atccaacggt 7260
ggatgggata atgacaatag acctagatcc tgtaatatac gatccaaaat ttgaaaagca 7320
actaggacag gttatgctcc tggttctgtg tgcagttcaa cttttgttaa tgagaactc 7380
atgggctttt tgtgaagctc taaccctagc cacaggacca ataacaacac tctgtgaagg 7440
atcacctgg aagttctgga acaccacgat agctgtttcc atggcgaaca tctttagagg 7500
gagctattta gcaggagctg ggcttgcttt ttctatcatg aaatcagttg gaacaggaaa 7560
gagagggaca gggtcacagg gtgaaacctt gggagaaaag tggaaaaaga attgaatca 7620
attaccccgg aaagagtttg acctttacaa gaaatccgga atcactgaag tggatagaac 7680
```

-continued

```
agaagccaaa gaagggttga aaagaggaga aataacacac catgccgtgt ccagaggcag 7740
cgcaaaactt caatggttcg tggagagaaa catggtcatc cccgaaggaa gagtcataga 7800
cttaggctgt ggaagaggag gctggtcata ttattgtgca ggactgaaaa aagttacaga 7860
agtgcgagga tacacaaaag gcggcccagg acatgaagaa ccagtaccta tgtctacata 7920
cggatcgaac atagtcaagt taatgagtgg aaaggatgtg ttttatcttc cacctgaaaa 7980
gtgtgatact ctattgtgtg acattggaga atcttcacca agcccaacag tggaagaaag 8040
cagaaccata agagtcttga agatggttga accatggcta agaaataacc agttttgcat 8100
taaagtattg aacccttaca tgccaactgt gattgagcac ctagaaagac tacaaaggaa 8160
acatggagga atgcttgtga gaaatccact ctcacgaaac tccacgcacg aaatgtactg 8220
gatatctaat ggcacaggca atatcgtttc ttcagtcaac atggtatcca gattgctact 8280
taacagattc acaatgacac ataggagacc caccatagag aaagatgtgg atttaggagc 8340
ggggacccga catgtcaatg cggaaccaga acacccaac atggatgtca ttggggaaag 8400
aatcaagaagg atcaaggagg agcatagttc aactgghcac tatgatgatg aaaatcctta 8460
taaaacgtgg gcttaccatg gatcctatga agttaaggcc acaggctcag cctcctccat 8520
gataaatgga gtcgtgaaac tcctcacgaa accatgggat gtggtgccca tggtgacaca 8580
gatggcaatg acggatacaa ccccattcgg ccagcaaagg gttttaaag agaaagtgga 8640
caccaggaca cccagaccta tgccaggaac aagaaaggtt atggagatca cagcggaatg 8700
gctttggaga accctgggaa ggaacaaaag acccagatta tgtacgagag aggagttcac 8760
aaaaaaaggtc agaaccaacg cagctatggg cgccgttttt acagaggaga accaatggga 8820
cagtgctaga gctgctgttg aggatgaaga attctggaaa ctcgtggaca gagaacgtga 8880
actccacaaa ttgggcaagt gtggaagctg cgtttacaac atgatgggca agagagagaa 8940
gaaacttgga gagtttggca aagcaaaaag cagtagagcc atatggtaca tgtggttggg 9000
agccagatac cttgagttcg aagcactcgg attcttaaat gaagaccatt ggttctcgcg 9060
tgaaaactct tacagtggag tagaaggaga aggactgcac aagctgggat acatcttaag 9120
agacatttcc aagataccg gaggagctat gtatgctgat gacacagctg ttgggacac 9180
aagaataaca gaagatgacc tgcacaatga ggaaaaaaatc acacagcaga tggaccctga 9240
acacaggcag ttagcaaacg ctatattcaa gctcacatac caaaacaaag tggtcaaagt 9300
tcaacgacca actccaaagg gcacggtaat ggacatcata tctaggaaag accaaagagg 9360
cagtggacag gtgggaactt atggtctgaa tacattcacc aacatggaag cccagttaat 9420
cagacaatg gaaggagaag gtgtgttgtc gaaggcagac ctcgagaacc ctcatctgcg 9480
agagaagaaa gttacacaat ggttggaaac aaaaggagtg gagaggttaa aagaatggc 9540
catcagcggg gatgattgcg tggtgaaacc aattgatgac aggttcgcca tgcccctgct 9600
tgccctgaat gacatgggaa aagttaggaa ggacatacct caatggcagc catcaaaggg 9660
atgggcatgat tggcaacagg tcccttctg ctcccaccac tttcatgaat tgatcatgaa 9720
agatggaaga aagttggtag ttccctgcag acctcaggat gaattaatcg gagagcgag 9780
aatctctcaa ggagcaggat ggagcttag agaaactgca tgcctagga aagcctacgc 9840
ccaaatgtgg actctcatgt actttcacag aagagatctt agactagcat ccaacgccat 9900
atgttcagca gtaccagtcc attgggtccc cacaagcaga acgacgtggt ctattcatgc 9960
tcaccatcag tggatgacta cagaagacat gcttactgtt tggaacaggg tgtggataga 10020
ggataatcca tggatggaag acaaaactcc agtcaaaacc tgggaagatg ttccatatct 10080
agggaagaga gaagaccaat ggtgcggatc actcattggt ctcacttcca gagcaacctg 10140
ggcccagaac atacttacgg caatccaaca ggtgagaagc cttataggca atgaagagtt 10200
tctggactac atgccttcga tgaagagatt caggaaggag gaggagtcag agggagccaa 10260
ttggtaaacg taggaagtga aaaagaggca aactgtcagg ccaccttaag ccacagtacg 10320
gaagaagctg tgcagcctgt gagccccgtc caaggacgtt aaaagaagaa gtcaggccca 10380
aaagccacgt tttgagcaaa ccgtgctgcc tgtggctccg tcgtggggac gtaaaacctg 10440
ggaggctgcg actagcggtt agaggagacc cctcccgtga cacaacgcag cagcgggcc 10500
caagactaga ggttagagga gaccccccgc aaataaaaac agcatattga cgctgggaga 10560
gaccagagat cctgctgtct cctcagcatc attccaggca cagaacgcca gaaaatggaa 10620
tggtgctgtt gaatcaacag gttct 10645
```

SEQ ID NO: 9         moltype = RNA  length = 10618
FEATURE             Location/Qualifiers
misc_feature      1..10618
                    note = DENV4
source            1..10618
                    mol_type = other RNA
                    organism = synthetic construct
SEQUENCE: 9

```
agttgttagt ctgtgtggac cgacaaggac agttccaaat cggaagcttg cttaacacag 60
ttctaacagt ttgtttgaat agagagcaga tctctggaaa atgaaccaa cgaaaaaagg 120
tggttagacc acctttcaat atgctgaaac gcgagagaaa ccgcgtatca accccctcaag 180
ggttggtgaa gagattctca accggacttt tttctggaaa aggacccttg cggatggtgc 240
tagcattcat cacgttttg cgagtccttt ccatcccacc acagcaggg atttctgaaga 300
gatgggaca gttgaagaaa aataaggcca tcaagatact gattggattc aggaaggaga 360
taggccgcat gctgaacatc ttgaacggga aaaaggtc aacgataaca ttgctgtgct 420
tgattcccac cgtaatggcg ttttccctca gcacaagaga tggcgaaccc tcatgatag 480
tggcaaaaca tgaaagggggg agacctctct tgtttaagac aacagagggg atcaacaaat 540
gcactctcat tgccatggac ttgggtgaaa tgtgtgagga cactgtcacg tataaatgcc 600
ccctactggt caataccgaa cctgaagaca ttgattgctg gtgcaacctc acgtctacct 660
gggtcatgta tggacatgc acccagagcg agaacggag acgagaaag cgctcagtag 720
cttaacacc acattcagga atgggattgg aaacaagagc tgagcatgg atgtcatcgg 780
aaggggctg gaagcatgct cagagagtag agagctggat actcagaaac ccaggattcg 840
cgctcttggc aggatttatg gcttatatga ttgggcaaac aggaatccag agaactgtct 900
tctttgtcct aatgatgctg gtcgccccat cctacggaat gcgatgcgta ggagtaggaa 960
acagagactt tgtggaagga gtctcaggtg gagcatgggt cgacctgtg ctagaacatg 1020
gaggatgcgt cacaaccatg gcccaggaa accaaccttt ggattttgaa ctgactaaga 1080
caacagccaa ggaagtggct ctgttaagaa cctattgcat tgaagcctca atatcaaaca 1140
taactacggc aacaagatgt ccaacgcaag gagagccttta tctgaaagag gaacaggacc 1200
```

-continued

```
aacagtacat ttgccggaga gatgtggtag acagagggtg gggcaatggc tgtggcttgt 1260
ttggaaaagg aggagttgtg acatgtgcga agttttcatg ttcggggaag ataacaggca 1320
atttggtcca aattgagaac cttgaataca cagtggttgt aacagtccac aatggagaca 1380
cccatgcagt aggaaatgac acatccaatc atggagttac agccatgata actcccaggt 1440
caccatcggt ggaagtcaaa ttgccggact atggagaact aacactcgat tgtgaaccca 1500
ggtctggaat tgactttaat gagatgattc tgatgaaaat gaaaagaaa acatggctcg 1560
tgcataagca atggttttg gatctgcctc ttccatggac agcaggagca gacacatcag 1620
aggttcactg gaattacaaa gagagaatgg tgacatttaa ggttcctcat gccaagagac 1680
aggatgtgac agtgctggga tctcaggaag gagccatgca ttctgccctc gctggagcca 1740
cagaagtgga ctccggtgat ggaaatcaca tgtttgcagg acatcttaag tgcaaagtcc 1800
gtatggagaa attgagaatc aagggaatgt catacacgat gtgttcagga aagttttcaa 1860
ttgacaaaga gatggcagaa acacagcatg ggacaacagt ggtgaaagtc aagtatgaag 1920
gtgctggagc tccgtgtaaa gtccccatag agataagaga tgtaaacaag gaaaagtgg 1980
ttgggcgtat catctcatcc accccttggg ctgagaatac caacagtgta accaacatag 2040
aattagaacc ccccctttggg gacagctaca tagtgatagg tgttggaaac agcgcattaa 2100
cactccattg gttcaggaaa gggagttcca ttggcaagat gtttgagtcc acatacagag 2160
gtgcaaaacg aatggccatt ctaggtgaaa cagcttggga ttttggttcc gttggtggac 2220
tgttcacatc attgggaaag gctgtgcacc aggtttttgg aagtgtgtat acaaccatgt 2280
ttggaggagt ctcatggatg attagaatcc taattgggtt cttagtgttg tggattggca 2340
cgaactcgag gaacacttca atggctatga cgtgcatagc tgttgaggga atcactctgt 2400
ttctgggctt cacagttcaa gcagacatgg ttgtgtggc gtcatggagt gggaaagaat 2460
tgaagtgtgg aagcggaatt tttgtggttg acaacgtgca cacttggaca gaacagtaca 2520
aatttcaacc agagtcccca gcgagactag cgtctgcaat attaaatgcc cacaaagatg 2580
gggtctgtgg aattagatca accacgaggc tggaaaatgt catgtggaag caaataaacca 2640
acgagctaaa ctatgttctc tgggaaggag acatgaccct cactgtagtg gctggggatg 2700
tgaaggggt gttgaccaaa ggcaaggaga cactcacacc cccagtgagt gatctgaaat 2760
attcatggaa gacatgggga aaagcaaaaa tcttcacccc agaagcaaga aatagcacat 2820
ttttaataga cggaccagac acctctgaat gccccaatga acgaagagca tggaactctc 2880
ttgaggtgga agactatgga tttggcatgt tcacgaccaa catatggatg aaattccgag 2940
aaggaagttc agaagtgtgt gaccacaggt taatgtcagc tgcaattaaa gatcagaaag 3000
ctgtgcatgc tgacatgggt tattggatag agagctcaaa aaaccagacc tggcagatag 3060
agaaagcatc tcttattgaa gtgaaaacat gtctgtggcc caagacccac acactgtgga 3120
gcaatggagt gctggaaagc cagatgtcca ttccaaaatc atatgcgggc ccttttcac 3180
agcacaatta ccgccagggc tatgccacgc aaaccgtggg ccatggcac ttaggcaaat 3240
tagagataga ctttggagaa tgccccggaa caacagtcac caattcaggag gattgtgacc 3300
atagaggccc atctttgagg accaccactg catctggaaa actagtcacg caatggtgct 3360
gccgctcctg cacgatgcct cccttaaggt tcttgggaga agatgggtgc tggtatggga 3420
tggagattag gcccttgagt gaaaagaag agaacatggt caaatcacag gtgacggccg 3480
gacagggcac atcagaaact ttttctatgg gtctgttgtg cctgaccttg tttgtggaag 3540
aatgcttgag gagaagagtc actaggaaac acatgatatt agttgtggtg atcactcttt 3600
gtgctatcat cctgggaggc ctcacatgga tggacttact acgagccctc atcatgttgg 3660
gggacactat gtctggtaga ataggaggac agatccacct agccatcatg gcagtgttca 3720
agatgtcacc aggatacgtg ctgggtgtgt ttttaaggaa actcacttca agagagacag 3780
cactaatggt aataggaatg gccatgacaa cggtgctttc aatccacat gaccttatgt 3840
aactcattga tggaatatca ctgggactaa ttttgctaaa aatagtaaca cagttttgaca 3900
acacccaagt gggaaccta gctctttcct tgactttcat aagatcaaca atgccattgg 3960
tcatggcttg gaggaccatt atggctgtgt tgtttgtgt cacactcatt cctttgtgca 4020
ggacaagctg tcttcaaaaa cagtctcatt gggtagaaat aacagcactc atcctaggag 4080
cccaagctct gccagtgtac ctaatgactc ttatgaaagg agcctcaaga agatcttggc 4140
ctcttaacga gggcataatg gctgtgggtt tggttagtct cttaggaagc gctcttttaa 4200
agaatgatgt ccccttagct ggcccaatgg tggcaggaga cttacttctg gcggcttaca 4260
tgatgagtgt tagctcagca gatctgtcac tagagaaggc cgccaacgtg cagtgggatg 4320
aaaatgcaga cataacaggc tcaagcccaa tcatagaagt gaagcaggat gaagatggct 4380
ctttctccat acgggacgtc gaggaaacca atatgataac ccttttggtg aaactggcac 4440
tgataacagt gtcaggtctc tacccttgg caattccagt cacaatgacc ttatggtaca 4500
tgtggcaagt gaaaacacaa agatcaggag ccctgtggga cgtcccctca cccgctgcca 4560
ctaaaaaagc cgcactgtct gaaggagtgt acaggatcat gcaaagggg ttattcggga 4620
aaactcaggt tggagtaggg atacacatgg aaggtgtatt tcacacaatg tggcatgtaa 4680
caagaggatc agtgatctgc cacgagactg ggagattgga gccatcttgg gctgacgtca 4740
ggaatgacat gatatcatac ggtgggggat ggaggcttgg agacaaatgg gacaaagaag 4800
aagacgttca ggtcctcgcc atagaaccag gaaaaaatcc taaacatgtc caaacgaaac 4860
ctggccttt caagaccccta actggagaaa ttggagcagt aacattagat ttcaaacccg 4920
gaacgtctgg ttctccccatc atcaacagga aggaaaagt catcggactc tatggaaatg 4980
gagtagttac caaatcaggt gattacgtca gtgccataac gaaagccgaa agaattggag 5040
agccagatta tgaagtggat gaggacattt tcgaaagaa aagattaact ataatggact 5100
tacaccccgg agctggaaag acaaaaagaa ttcttccatc aatagtgaga gaagccttaa 5160
aaaggaggct acgaactttg attttagctc ccacgagagt ggtggcggcc gagatggaag 5220
aggccctacg tggactgcca atccgttatc agaccccagc tgtgaaatca gaacacacag 5280
gaagagagat tgtagacctc atgtgtcatg caaccttcac aacaagactt ttgtcatcaa 5340
ccagggttcc aaaattacaac cttatagtga tggatgaagc acatttcacc gatcttccta 5400
gtgtcgcggc tagaggatac atctcgacca gggtggaaat gggagaggca gcagccatct 5460
tcatgaccgc aacccctccc ggagcgcacag atccctttcc ccagagcaac agcccaatag 5520
aagacatcga gaggaaatt ccggaaaggt catggaacac agggttcgac tggataacag 5580
actaccaagg gaaaactgtg tggtttgttc ccagcataaa agctgaaat gacattgcaa 5640
attgtttgag aaagtcggga aagaaagtta tccagttgag taggaaaacc tttgatacag 5700
agtatccaaa aacgaaactc acggactggg actttgtggt cactacagac atatctgaaa 5760
tggggggccaa ttttagagcc gggagagtga tagaccctag aagatgcctc aagccagtta 5820
tcctaccaga tgggccagag agagtcattt tagcaggtcc tattccagtg actccagcaa 5880
gcgctgctca gagaagaggg cgaataggaa ggaacccagc acaagaagac gaccaatacg 5940
```

```
ttttctccgg agacccacta aaaaatgatg aagatcatgc ccactggaca gaagcaaaga    6000
tgctgcttga caatatctac accccagaag ggatcattcc aacattgttt ggtccggaaa    6060
gggaaaaaac ccaagccatt gatggagagt ttcgcctcag aggggaacaa aggaagactt    6120
ttgtggaatt aatgaggaga ggagaccttc cggtgtggct gagctataag gtagcttctg    6180
ctggcatttc ttacaaagat cgggaatggt gcttcacagg ggaaagaaat aaccaaattt    6240
tagaagaaaa catggaggtt gaaatttgga ctagagaggg agaaaagaaa aagctaaggc    6300
caagatggtt agatgcacgt gtatacgctg accccatggc tttgaaggat ttcaaggagt    6360
ttgccagtgg aaggaagagt ataactctcg acatcctaac agagattgcc agtttgccaa    6420
cttaccttc ctctagggcc aagctcgccc ttgataacat agtcatgctc cacacaacag    6480
aaagaggagg gagggcctat caacacgccc tgaacgaact tccggagtca ctggaaacac    6540
tcatgcttgt agctttacta ggtgctatga cagcaggcat cttcctgttt ttcatgcaag    6600
ggaaaggaat agggaaattg tcaatggggtt tgataaccat tgcggtggct agtggcttgc    6660
tctgggtagc agaaattcaa ccccagtgga tagcggcctc aatcatacta gagttttttc    6720
tcatgtact gttgataccg gaaccagaaa aacaaaggac cccacaagac aatcaattga    6780
tctacgtcat attgaccatt ctcaccatca ttggtctaat agcagccaac gagatggggc    6840
tgattgaaaa aacaaaaacg gattttgggt tttaccaggt aaaaacagaa accaccatcc    6900
tcgatgtgga cttgagacca gcttcagcat ggacgctcta tgcagtagcc accacaattc    6960
tgactcccat gctgagacac accatagaaa acacgtcgagc caacctatct ctagcagcca    7020
ttgccaacca ggcagccgtc ctaatgggc ttggaaaagg atggccgctc cacagaatgg    7080
acctcggtgt gccgctgtta gcaatgggat gctattctca agtgaaccca ataaccttga    7140
cagcatcctt agtcatgctt ttcgtccatt atgcaataat aggcccagga ttgcaggcaa    7200
aagccacaag agaggcccag aaaaggacag ctgctgggat catgaaaaat cccacagtgg    7260
acgggataac agtaatagat ctagaaccaa tatcctatga cccaaaattt gaaaagcaat    7320
tagggcaggt catgctacta gtcttgtgtg ctggacaact actcttgatg agaacaacat    7380
gggctttctg tgaagtcttg actttggcca caggaccaat cttgaccttg tgggagggca    7440
acccgggaag gttttggaac acgaccatag ccgtatccgc cgccaacatt ttcaggggaa    7500
gttacttggc gggagctgga ctggcttttt cactcataaa gaatgcacaa accctaggaa    7560
ggggaactgg gaccacagga gagacactgg gagagaagtg gaagagacag ctaaactcat    7620
tagacagaaa agagtttgaa gagtataaaa gaagtggaat actagaagtg gacaggactg    7680
aagccaagtc tgccctgaaa gatgggtcta aaatcaagca tgcagtatca agagggtcca    7740
gtaagatcag atggattgtt gagagaggga tggtaaagcc aaaagggaaa gttgtgatca    7800
ttggctgtgg gagaggagga tggtcttatt acatggcgac actcaagaac gtgactgaag    7860
tgaaagggta tacaaaagga ggtccaggac atgaagaacc gattcccatg ctacttatg    7920
gttggaattt ggtcaaactc cattcagggg ttgacgtgtt ctacaaaccc acagacgaag    7980
tggacaccct gctctgtgat attggggagt catcttctaa tccaacaata gaggaaggaa    8040
gaacattaag agttttgaag atggtggagc catggctctc ttcaaaacct gaattctgca    8100
tcaaagtcct taacccctac atgccaacag tcatagaaga gctggagaaa ctgcagaaa    8160
aacatggtgg gaaccttgtc agatgccgc tgtccaggaa ctccaccat gagatgtatt    8220
gggtgtcagg agcgtcggga aacattgtga gctctgtgaa cacaacatca aagtgttgt    8280
tgaacaggtt cacaacaagg cataggagac ccacttatga gaaggacgta gatcttgggg    8340
caggaacgag aagtgtctcc actgaaacag aaaaaccaga catgacaatc attgggagaa    8400
ggcttcagcg attgcaagaa gagcacaaag aaacctggca ttatgatcag gaaaacccat    8460
acagaacctg ggcgtatcat ggaagctatg aagctccttc gacaggctct gcatcctcca    8520
tggtgaacgg ggtggtaaaa ctgctaacaa acccctggga tgtgattcca atggtgactc    8580
agttagccat gacagataca accccttttg ggcaacaaag agtgttcaaa gagaaggtgg    8640
ataccagaac accacaacca aaacccgta cacgaatggt tatgaccacg acagccaatt    8700
ggctgtgggc cctccttgga aagaagaaaa atcccagact gtgcacaagg gaagagttca    8760
tctcaaaagt tagatcaaac gcagccatag cgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctataa catgatggga aaacgtgaga    8940
aaaagttagg agagttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccatttcta aactaaccta tcaaaacaaa gtggtgaaag    9300
tcctcagacc cacaccgcgg ggagcggtga tggatatcat atccaggaaa gaccaaagag    9360
gtagtggaca agttggaaca tatggttga acacattcac caacatgaa gttcaactca    9420
tccgccaaat ggaagctgaa ggagtcatca cacaagatga catgcagaac ccaaagggt    9480
tgaaagaaag agttgagaaa tggctgaaag agtgtggtgt cgacaggtta aagaggatgg    9540
caatcagtgg agacgattgc gtggtgaagc ccctagatga gaggtttgc acttccctcc    9600
tcttcttgaa cgacatggga aaggtgagga agacattcc gcagtgggaa ccatctaagg    9660
gatggaaaaa ctggcaagag gttcctttt gctccaccca ctttcacaag atctttatga    9720
aggatggccg ctcactagtt gttccatgta gaaaccagga tgaactgata ggagagcca    9780
gaatctcgca gggagctgga tggagcttaa gagaaacagc ctgcctgggc aaagcttacg    9840
cccagatgtg gtcgcttatg tacttccaca agggatct gcgtttagcc tccatggcca    9900
tatgctcagc agttccaacg gaatggtttc caacaagcag acaacatgg tcaatccacg    9960
ctcatcacca gtggatgact actgaagata tgctcaaagt gtggaacaga gtgtggatag   10020
aagacaaccc taatatgact gacaagactc cagtccattc gtgggaagat ataccttacc   10080
tagggaaag agaggatttg tggtgtggat ccctgattgg actttcttcc agagccacct   10140
gggcgaagaa cattcacacg gccataaccc aggtcaggaa cctgatcgga aaagaggaat   10200
acgtggatta catgccagta atgaaagat acagtgctcc ttcagagagt gaaggagttc   10260
tgtaattacc aacaacaaac accaaaggct attgaagtca ggccacttgt gccacggttt   10320
gagcaaaccg tgctgcctgt agctccgcca ataatgaagt gtaataat ccaggggag   10380
gccatgcgcc acggaagctg tacgcgtggc atattggact agcggttaga ggagacccct   10440
cccatcactg acaaaacgca gcaaagggg gcccaagact agaggttaga ggagacccc   10500
ccaacacaaa aacagcatat tgacgctggg aaagaccaga gatcctgctg tctctgcaac   10560
atcaatccag gcacagagcg ccgcaagatg gattggtgtt gttgatccaa caggttct    10618
```